US006624180B2

(12) United States Patent
South et al.

(10) Patent No.: US 6,624,180 B2
(45) Date of Patent: Sep. 23, 2003

(54) SUBSTITUTED POLYCYCLIC ARYL AND HETEROARYL PYRIDINES USEFUL FOR SELECTIVE INHIBITION OF THE COAGULATION CASCADE

(75) Inventors: Michael J. South, St. Louis, MO (US); Brenda Case, St. Louis, MO (US); Danny J. Garland, Ballwin, MO (US); Michael J. Hayes, St. Louis, MO (US); Horng-Chih Huang, Chesterfield, MO (US); Wei Huang, Wildwood, MO (US); Darin E. Jones, Ballwin, MO (US); William L. Neumann, St. Louis, MO (US); John J. Parlow, Arnold, MO (US); David B. Reitz, Chesterfield, MO (US); Melvin L. Rueppel, St. Louis, MO (US); Rondald K. Webber, St. Charles, MO (US)

(73) Assignee: Pharmacia Corporation, St. Louis, MO (US)

(*) Notice: Subject to any disclaimer, the term of this patent is extended or adjusted under 35 U.S.C. 154(b) by 0 days.

(21) Appl. No.: 09/989,634

(22) Filed: Nov. 20, 2001

(65) Prior Publication Data

US 2003/0139401 A9 Jul. 24, 2003

Related U.S. Application Data

(60) Provisional application No. 60/252,158, filed on Nov. 20, 2000, and provisional application No. 60/350,069, filed on Nov. 7, 2001.

(51) Int. Cl.$^7$ .................... C07D 213/06; A61K 31/44
(52) U.S. Cl. ............ 514/352; 514/242; 514/255.06; 514/275; 546/309; 544/194; 544/316; 544/407
(58) Field of Search .............. 546/309; 514/352, 514/275, 255.06, 242; 544/194, 316, 407

(56) References Cited

U.S. PATENT DOCUMENTS

| | | | |
|---|---|---|---|
| 5,441,960 A | 8/1995 | Bernstein et al. | |
| 5,656,645 A | 8/1997 | Tamura et al. | |
| 5,658,930 A | 8/1997 | Tamura et al. | |
| 5,668,289 A | 9/1997 | Sanderson et al. | |
| 5,792,779 A | 8/1998 | Sanderson et al. | |
| 5,861,380 A | 1/1999 | Gyorkos et al. | |
| 5,866,573 A | 2/1999 | Sanderson et al. | |
| 5,869,487 A | 2/1999 | Coburn et al. | |
| 5,872,138 A | 2/1999 | Naylor-Olsen et al. | |
| 6,011,158 A | 1/2000 | Tamura et al. | |
| 6,037,356 A | 3/2000 | Lu et al. | |

FOREIGN PATENT DOCUMENTS

| | | |
|---|---|---|
| EP | 528 633 B1 | 2/1993 |
| EP | 826 671 A1 | 3/1998 |
| EP | 936 216 A1 | 8/1999 |
| EP | 940 400 A1 | 9/1999 |
| EP | 997 474 A1 | 5/2000 |
| WO | WO 93/21214 A1 | 10/1993 |
| WO | WO 96/18644 A1 | 6/1996 |
| WO | WO 96/33974 A1 | 10/1996 |
| WO | WO 96/39380 A1 | 12/1996 |
| WO | WO 96/40100 A1 | 12/1996 |
| WO | WO 97/01338 A1 | 1/1997 |
| WO | WO 97/30708 A1 | 8/1997 |
| WO | WO 97/40024 A1 | 10/1997 |
| WO | WO 97/46207 A2 | 12/1997 |
| WO | WO 98/08840 A1 | 3/1998 |
| WO | WO 98/09949 A1 | 3/1998 |
| WO | WO 98/10763 A1 | 3/1998 |
| WO | WO 98/16525 A1 | 4/1998 |
| WO | WO 98/16547 A1 | 4/1998 |
| WO | WO 98/17274 A1 | 4/1998 |
| WO | WO 98/31670 A1 | 7/1998 |
| WO | WO 98/42342 A1 | 10/1998 |
| WO | WO 98/47876 A1 | 10/1998 |
| WO | WO 98/50420 A1 | 11/1998 |
| WO | WO 99/00121 A1 | 1/1999 |
| WO | WO 99/00126 A1 | 1/1999 |
| WO | WO 99/00128 A1 | 1/1999 |
| WO | WO 99/11267 A1 | 3/1999 |
| WO | WO 99/26920 A1 | 6/1999 |
| WO | WO 99/26926 A1 | 6/1999 |
| WO | WO 99/36426 A1 | 7/1999 |
| WO | WO 99/48892 | 9/1999 |
| WO | WO 99/59591 A1 | 11/1999 |
| WO | WO 99/61442 A1 | 12/1999 |

(List continued on next page.)

OTHER PUBLICATIONS

Rauch, et al., Thrombus Formation on Atherosclerotic Plaques: Pathogenesis and Clinical Consequences, Annals of Internal Medicine, 2001, pp. 224–233, vol. 134—No. 3.

Van Aken, et al., Anticoagulation: The Present and Future, Clin. Appl. Thrombosis/Hemostasis, 2001, pp. 195–204, vol. 7—No. 3.

Majerus, et al. "Anticoagulant, Thrombolytic, and Antiplatlet Drugs." Goodman & Gilman's The Pharmacological Basis of Therapeutics, Ninth Edition, 1996, pp. 1341–1359, McGraw–Hill, New York.

Handin, R., "Bleeding and Thrombosis." Harrison's Principles of Internal Medicine, 12th Edition, 1991, pp. 348–353, McGraw–Hill, Inc., New York.

Sanderson et al., "L–373,890, An Achiral, Noncovalent, Subnamomolar Thrombin Inhibitor." Bioorganic & Medicinal Chemistry Letters, vol. 7, No. 12, pp. 1497–1500, 1997.

Patel et al., "Directed aminomethylation of 3–Hydroxy 2(1Hpyridinones and –3hydroxy–4(H)–pyridinones: Synthesis of iso–deferiprone", Tetrahedron, Elsevier Science Publishers, Amsterdam, NL vol. 52, No. 5, 1996, AP004104485.

*Primary Examiner*—Zinna Northington Davis

(57) ABSTRACT

The present invention relates to compounds, and prodrugs thereof, composition and methods useful for preventing and treating thrombotic conditions in mammals. The compounds of the present invention, and prodrugs thereof, selectively inhibit certain proteases of the coagulation cascade.

41 Claims, No Drawings

U.S. PATENT DOCUMENTS

| | | | | | | | |
|---|---|---|---|---|---|---|---|
| WO | WO 99/62538 A1 | 12/1999 | | WO | WO 00/32574 A1 | 6/2000 | |
| WO | WO 99/64446 A1 | 12/1999 | | WO | WO 00/39102 A1 | 7/2000 | |
| WO | WO 00/03743 | * 1/2000 | .......... A61K/38/00 | WO | WO 00/69826 A1 | 11/2000 | |
| WO | WO 00/18762 A1 | 4/2000 | | WO | WO 00/69832 A1 | 11/2000 | |
| WO | WO 00/26210 A1 | 5/2000 | | WO | WO 00/69833 A1 | 11/2000 | |
| WO | WO 00/26211 A1 | 5/2000 | | | | | |

* cited by examiner

SUBSTITUTED POLYCYCLIC ARYL AND HETEROARYL PYRIDINES USEFUL FOR SELECTIVE INHIBITION OF THE COAGULATION CASCADE

CROSS REFERENCE TO RELATED APPLICATIONS

This application claims priority from Provisional application Ser. No. 60/252,158, filed Nov. 20, 2000 and Provisional application Ser. No. 60/350,069 filed Nov. 7, 2001, which are both hereby incorporated by reference in their entirety.

FIELD OF THE INVENTION

This invention is in the field of anticoagulant therapy, and specifically relates to compounds, compositions and methods for preventing and treating thrombotic conditions such as coronary artery and cerebrovascular disease. More particularly, the invention relates to substituted polycyclic aryl and heteroaryl pyridine compounds, and prodrugs thereof, that inhibit serine proteases of the coagulation cascade.

BACKGROUND OF THE INVENTION

Hemorrhage, intravascular thrombosis, and embolism are common clinical manifestations of many diseases [see R. I. Handin in *Harrison's Principles of Internal Medicine* (J. D. Wilson, et al. eds., 12th ed. 1991) New York, McGraw-Hill Book Co., pp. 348–351]. The normal hemostatic system limits blood loss by precisely regulated interactions between components of the vessel wall, circulating blood platelets, and plasma proteins. However, unregulated activation of the of the hemostatic system may cause thrombosis, which can reduce blood flow to critical organs like the brain and myocardium. Physiological systems control the fluidity of blood in mammals [see P. W. Majerus, et al. in *Goodman & Gilman's The Pharmacological Basis of Therapeutics* (J. G. Hardman & L. E. Limbird, eds., 9th ed. 1996) New York, McGraw-Hill Book Co., pp. 1341–1343]. Blood must remain fluid within the vascular systems and yet quickly be able to undergo hemostasis. Hemostasis, or clotting, begins when platelets first adhere to macromolecules in subendothelian regions of injured and/or damaged blood vessels. These platelets aggregate to form the primary hemostatic plug and stimulate local activation of plasma coagulation factors leading to generation of a fibrin clot that reinforces the aggregated platelets.

Plasma coagulation factors, also referred to as protease zymogens, include factors II, V, VII, VIII, IX, X, XI, and XII. These coagulation factors or protease zymogens are activated by serine proteases leading to coagulation in a so called "coagulation cascade" or chain reaction.

Coagulation or clotting occurs in two ways through different pathways. An intrinsic or contact pathway leads from XII to XIIa to XIa to IXa and to the conversion of X to Xa. Xa with factor Va converts prothrombin (II) to thrombin (IIa) leading to conversion of fibrinogen to fibrin. Polymerization of fibrin leads to a fibrin clot. An extrinsic pathway is initiated by the conversion of coagulation factor VII to VIIa by Xa. Factor VIIa, a plasma protease, is exposed to, and combines with its essential cofactor tissue factor (TF) which resides constitutively beneath the endothelium. The resulting factor VIIa/TF complex proteolytically activates its substrates, factors IX and X, triggering a cascade of reactions that leads to the generation of thrombin and a fibrin clot as described above.

While clotting as a result of an injury to a blood vessel is a critical physiological process for mammals, clotting can also lead to disease states. A pathological process called thrombosis results when platelet aggregation and/or a fibrin clot blocks (i.e., occludes) a blood vessel. Arterial thrombosis may result in ischemic necrosis of the tissue supplied by the artery. When the thrombosis occurs in a coronary artery, a myocardial infarction or heart attack can result. A thrombosis occurring in a vein may cause tissues drained by the vein to become edematous and inflamed. Thrombosis of a deep vein may be complicated by a pulmonary embolism. Preventing or treating clots in a blood vessel may be therapeutically useful by inhibiting formation of blood platelet aggregates, inhibiting formation of fibrin, inhibiting thrombus formation, inhibiting embolus formation, and for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels.

In order to treat such conditions, researchers have sought to discover chemical compounds that efficaciously and selectively control the clotting process. In addition, such compounds may provide a better understanding of the pathways involved in the coagulation process.

Thus far, many of the compounds that have been discovered possess a polar or basic functional group which is integrally responsible for the desired biological activity. Frequently, this polar functional group is a nitrogen atom of, for example, a guandine, alkyl-amidine or aryl-amidine group. Because these functionalities are highly basic, they remain protonated at physiologically relevant pH's. The ionic nature of such protonated species hinders their permeability across lipophilic membranes, which can reduce bioavailability when the pharmaceutical agent is administered orally.

In order to circumvent such a problem, it is often advantageous to perform a derivatization or chemical modification of the polar functionality such that the pharmaceutical agent becomes neutrally charged and more lipophilic, thereby facilitating absorption of the drug. However, for the derivatization to be useful, the derivatization must be bioconvertable at the target site or sites of desired pharmacological activity and cleaved under normal physiological conditions to yield the biologically active drug. The term "prodrug" has been used to denote such a chemically modified intermediate.

There have been limited reports of non-peptidic and peptidic pyridine compounds that act as an inhibitor of a coagulation factor present in the coagulation cascade or clotting process. In PCT Patent Application WO 00/039102, Wexler et al. describe certain 3,5-unsubstituted, 3,5-dichloro, 3-fluoro-5-chloro, 3-chloro-5-fluoro, and 3,5-difluoro pyrid-2-ylacetamides that are further substituted at the 6-position by several groups including several substituted aminos and reported to be inhibitors of trysin-like serine protease enzymes, especially factor Xa and thrombin. There have been reports of non-peptidic benzene compounds that act as an inhibitor of a coagulation factor present in the coagulation cascade or clotting process. In PCT Patent Applications WO 99/00121 and WO 99/00128, Beight et al. describe benzenes that may be fully substituted by substituents that include acylamido, acyloxy, carboxamido, alkoxy, acetamide, carbonates, carbamates, ureas, and other groups and having inhibitory activity against factor Xa. In U.S. Pat. No. 5,872,138 and PCT Patent Application WO 98/10763, Naylor-Olsen et al. describe disubstituted benzenes having a group linked through an oxygen, nitrogen or sulfur heteroatom, any one of six basic heterocycles linked to the ring through linker group, and, optionally, an additional alkyl, alkenyl, alkoxy, amino, or arylmethylenesulfonamido group and claimed to inhibit human thrombin. In PCT Patent Application WO 99/26920, Semple et al. disclose 1-oxy-2,3,4,5-tetrasubstitutedphenylacetamides having an acyl function in the group substituting the amide nitrogen and having activity against thrombin. In PCT Patent Application WO 96/39380, Lu and Soll describe bis-(sulfonamido substitutedbenzoyl) derivatives of diamines claimed to have utility as inhibitors of thrombotic disorders. In PCT Patent Application WO 96/40100, Illig et al. describe sulfonamido substitutedbenzoyl and benzyl derivatives of amines directed to non-peptidic factor Xa and claimed to have utility as inhibitors of thrombotic disorders.

SUMMARY OF THE INVENTION

Among the objects of the present invention, therefore, is the provision of compounds useful for selective inhibition of certain enzymes that act upon the coagulation cascade thereby preventing and treating thrombotic conditions in mammals.

Another object of the present invention is the provision of prodrug compounds useful for selective inhibition of certain enzymes that act upon the coagulation cascade thereby preventing and treating thrombotic conditions in mammals. In general, these prodrug compounds undergo hydrolysis, oxidation, reduction or elimination at a derivatized amidine group to yield the active compound.

Briefly, therefore, the present invention is directed to the compound, per se, to the prodrug of the compound, to pharmaceutical compositions comprising the compound or prodrug and a pharmaceutically acceptable carrier, and to methods of use. The compound corresponds to Formula A:

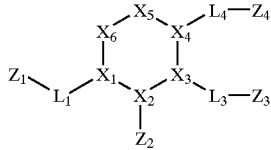

Formula A wherein $X_1$, $X_2$, $X_3$, $X_4$, $X_5$, and $X_6$ are each ring atoms defining a 6 membered heterocyclic or aromatic ring;

$X_1$, $X_2$, and $X_4$ are independently carbon or nitrogen;

$X_3$ is carbon;

$X_5$ and $X_6$ are independently carbon, nitrogen, oxygen or sulfur, provided at least one of $X_1$, $X_4$, and $X_6$ is other than carbon when $X_2$ is carbon;

$L_1$, $L_3$ and $L_4$ are linkages through which $Z_1$, $Z_3$, and $Z_4$, respectively, are covalently bonded to different ring atoms of the 6 membered heterocyclic or aromatic ring defined by $X_1$, $X_2$, $X_3$, $X_4$, $X_5$, and $X_6$, wherein $Z_1$ is covalently bonded to $X_1$, $Z_3$ is covalently bonded to $X_3$, and $Z_4$ is covalently bonded to $X_4$, each of $L_1$, $L_3$ and $L_4$ independently being a covalent bond or comprising one or more atoms through which $Z_1$, $Z_3$, and $Z_4$ are covalently bonded to $X_1$, $X_3$ and $X_4$, respectively;

$Z_3$ is a substituted hydrocarbyl, or a 5 or 6 membered substituted heterocyclic or aromatic ring, the substituents of the hydrocarbyl or ring comprising an amidine, guanidine, amino, or aminoalkyl group, the ring atoms of the 5 or 6 membered heterocyclic or aromatic ring of $Z_3$ being carbon, sulfur, nitrogen, or oxygen, wherein the 5 or 6 membered ring is optionally substituted at any position with halogen, hydroxy, or alkyl;

$Z_4$ comprises hydrocarbyl, substituted hydrocarbyl or a 5 or 6-membered heterocyclic ring, the ring atoms of the 5 or 6-membered heterocyclic ring being carbon, sulfur, nitrogen or oxygen;

$Z_1$ is hydrogen, hydrocarbyl, or substituted hydrocarbyl; and $Z_2$ is a hydrogen bond acceptor covalently or datively bonded to $X_2$.

Other objects and features of this invention will be in part apparent and in part pointed out hereafter.

DETAILED DESCRIPTION OF THE PREFERRED EMBODIMENTS

Formula I Embodiment

In one embodiment, the present invention is directed to compounds of Formula (I) (which constitute a subset of the compounds of Formula (A)):

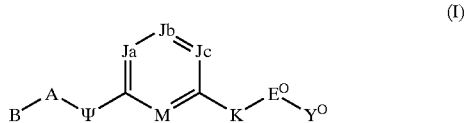

(I)

or a pharmaceutically acceptable salt thereof, wherein;

M is selected from the group consisting of N and N→O;

B is formula (V):

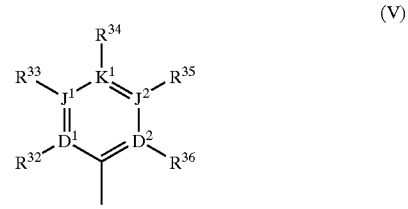

(V)

wherein $D^1$, $D^2$, $J^1$, $J^2$ and $K^1$ are independently selected from the group consisting of C, N, O, S and a bond with the provisos that no more than one can be a bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a bond when two of $D^1$, $D^2$, $J^1$, $J^2$ and $K^1$ are O and S, and no more than four of $D^1$, $D^2$, $J^1$, $J^2$ and $K^1$ are N, with the provisos that $D^1$, $D^2$, $J^1$, $J^2$ and $K^1$ are selected to maintain an aromatic ring system and that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of heterocyclylalkoxy, N-alkyl-N-arylamino, heterocyclylamino, heterocyclylalkylamino, hydrido, acetamido, haloacetamido, amidino, guanidino, dialkylsulfonium, trialkylphosphonium, dialkylsulfoniumalkyl, carboxy, heteroaralkylthio, haloalkylthio, alkanoyloxy, alkoxy, alkoxyalkyl, haloalkoxylalkyl, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{36}$ are independently optionally $Q^b$;

$R^{32}$ and $R^{33}$, $R^{33}$ and $R^{34}$, $R^{34}$ and $R^{35}$, or $R^{35}$ and $R^{36}$ is bonded together to form a ring selected from the group consisting of a cycloalkenyl ring having 5 through 8 members, a partially saturated heterocyclyl ring having 5 through 8 members, a heteroaryl ring having 5 through 6 members, and an aryl;

$R^9$ and $R^{10}$, $R^{10}$ and $R^{11}$, $R^{11}$ and $R^{12}$, or $R^{12}$ and $R^{13}$ is bonded together to form a ring selected from the group consisting of a cycloalkenyl ring having 5 through 8 members, a partially saturated heterocyclyl ring having 5 through 8 members, a heteroaryl ring having 5 through 6 members, and an aryl;

B is optionally formula (VI):

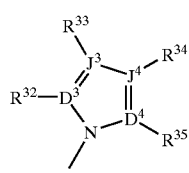

(VI)

wherein $D^3$, $D^4$, $J^3$, and $J^4$ are independently selected from the group consisting of C, N, O, and S, no more than one of $D^3$, $D^4$, $J^3$, and $J^4$ is O, no more than one of $D^3$, $D^4$, $J^3$, and $J^4$ is S, and no more than three of $D^1$, $D^2$, $J^1$, and $J^2$ are N, with the provisos that $D^3$, $D^4$, $J^3$, and $J^4$ are selected to maintain an aromatic ring system and that $R^{32}$, $R^{33}$, $R^{34}$, and $R^{35}$, and $R^{36}$ are each independently selected to maintain the tetravalent nature of carbon, trivalent nature of nitrogen, the divalent nature of sulfur, and the divalent nature of oxygen;

B is optionally selected from the group consisting of hydrido, trialkylsilyl, C2–C8 alkyl, C3–C8 alkenyl, C3–C8 alkylenyl, C3–C8 alkynyl, C2–C8 haloalkyl, and C3–C8 haloalkenyl wherein each member of group B is optionally substituted at any carbon up to and including 6 atoms from the point of attachment of B to A with one or more of the group consisting of $R_{32}$, $R_{33}$, $R_{34}$, $R_{35}$, and $R_{36}$;

B is optionally selected from the group consisting of C3–C15 cycloalkyl, C5–C10 cycloalkenyl, C4–C12 saturated heterocyclyl, and C4–C9 partially saturated heterocyclyl, wherein each ring carbon is optionally substituted with $R^{33}$ a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

A is selected from the group consisting of a bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(S), C(O)S, C(S)O, C(O)N($R^7$), C(S)N ($R^7$), ($R^7$)NC(O), ($R^7$)NC(S), S(O), S(O)$_2$, S(O)$_2$N ($R^7$), ($R^7$)NS(O)$_2$, Se(O), Se(O)$_2$, Se(O)$_2$N($R^7$), ($R^7$)NSe(O)$_2$, P(O)($R^8$), N($R^7$)P(O)($R^8$), P(O)(R)N($R^7$), C(NR$^7$)N($R^7$), ($R^7$)NC(NR$^7$), ($R^7$)NC(NR$^7$)NR$^7$ and N($R^7$) with the proviso that no more than one of the group consisting of rr and pa is 0 at the same time;

$R^7$ and $R^8$ are independently selected from the group consisting of hydrido, hydroxy, alkyl, alkenyl, aryl, aralkyl, aryloxy, alkoxy, alkenyloxy, alkylthio, alkylamino, arylthio, arylamino, acyl, aroyl, heteroaroyl, aralkoxyalkyl, heteroaralkoxyalkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, heteroaryl, heteroaryloxy, heteroarylamino, heteroaralkyl, heteroaralkyloxy, heteroaralkylamino, and heteroaryloxyalkyl;

$R^{14}$, $R^{15}$, $R^{37}$, $R^{38}$, $R^{39}$, $R^{40}$, $R^{41}$ and $R^{42}$ are independently selected from the group consisting of amidino, hydroxyamino, hydrido, hydroxy, halo, cyano, aryloxy, amino, alkylamino, dialkylamino, hydroxyalkyl, aminoalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, trialkylsilyl, dialkoxyphosphono, diaralkoxyphosphono, dialkoxyphosphonoalkyl, and diaralkoxyphosphonoalkyl, with the proviso that $R^{37}$ and $R^{38}$ are independently selected from other than formyl and 2-oxoacyl and $R^{38}$ is optionally substituted at from one through three of the ring carbons with a substituent selected from the group consisting of $R^{16}$, $R^{17}$, $R^{18}$, and $R^{19}$;

$R^{14}$ and $R^{14}$, when bonded to different carbons, are optionally bonded together to form a group selected from the group consisting of a bond, alkylene, haloalkylene, and a spacer selected to form a ring selected from the group consisting of cycloalkyl ring having from 5 through 8 members, cycloalkenyl ring having from 5 through 8 members, and a heterocyclyl having from 5 through 8 members;

$R^{14}$ and $R^{15}$, when bonded to different carbons, are optionally bonded together to form ring selected from the group consisting of a cycloalkyl ring having from 5 through 8 members, a cycloalkenyl ring having from 5 through 8 members, and a heterocyclyl having from 5 through 8 members;

$R^{15}$ and $R^{15}$, when bonded to different carbons, are optionally bonded together to form a ring selected from the group consisting of cycloalkyl ring having from 5 through 8 members, cycloalkenyl ring having from 5 through 8 members, and a heterocyclyl having from 5 through 8 members;

Ψ is selected from the group consisting of $NR^5$, O, C(O), C(S), S, S(O), S(O)$_2$, ON($R^5$), P(O)($R^8$), and $CR^{39}R^{40}$;

$R^5$ is selected from the group consisting of hydrido, hydroxy, amino, alkyl, alkenyl, alkynyl, aryl, aralkyl, aryloxy, aralkoxy, alkoxy, alkenyloxy, alkylthio, arylthio, aralkoxyalkyl, heteroaralkoxyalkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, and dialkoxyphosphonoalkyl;

$R^{39}$ and $R^{40}$, when bonded to the same carbon, are optionally bonded together to form a group selected from a group consisting of oxo, thiono, $R^5$—N, alkylene, haloalkylene, and a spacer having from 2 through 7 atoms to form a ring selected from the group consisting of a cycloalkyl ring having from 3 through 8 members, a cycloalkenyl ring having from 3 through 8 members, and a heterocyclyl ring having from 3 through 8 members;

Ja is independently selected from the group consisting of N and C—$X^o$;

Jb is independently selected from the group consisting of N and C—$R^1$;

Jc is independently selected from the group consisting of N and C—$R^2$;

$R^2$, $R^1$, and $X^o$ are independently selected from the group consisting of $Z^0$—Q, hydrido, alkyl, alkenyl, and halo;

$R^1$ and $X^o$ are independently optionally selected from the group consisting of amino, aminoalkyl, haloalkyl, haloalkoxy, haloalkylthio, amino, alkylamino, aminoalkyl, amidino, guanidino, hydroxy, hydroxyamino, alkoxy, hydroxyalkyl, alkoxyamino, thiol, alkylthio, dialkylsulfonium, trialkylphosphonium, dialkylsulfoniumalkyl, heteroarylamino, nitro, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$R^2$ is optionally selected from the group consisting of amidino, guanidino, dialkylsulfonium, trialkylphosphonium, dialkylsulfoniumalkyl, heteroarylamino, amino, nitro, alkylamino, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$X^0$ and $R^1$ are optionally selected to be —W=X—Y=Z— wherein —W=X—Y=Z— forms a ring selected from the group consisting of a heteroaryl ring having from 5 through 6 members and an aryl;

$R^1$ and $R^2$ are optionally selected to be —W=X—Y=Z— wherein —W=X—Y=Z— forms a ring selected from the group consisting of a heteroaryl ring having from 5 through 6 members and an aryl;

W, X, Y, and Z are independently selected from the group consisting of C($R^9$), C($R^{10}$), C($R^{11}$), C($R^{12}$) N, N($R^{10}$) O, S and a bond with the proviso that W, X, Y, and Z are optionally and independently selected to be a bond wherein one of W, X, Y, and Z is selected from the group consisting of N, N($R^{10}$), O, and S, with the further proviso that no more than one of W, X, Y, and Z is optionally O or S, and with the still further proviso that no more than three of W, X, Y, and Z are optionally N or N($R^{10}$);

$X^0$ and $R^1$ or $R^1$ and $R^2$ is optionally bonded together to form a ring selected from the group consisting of a cycloalkenyl ring having from 5 through 8 members and a partially saturated heterocyclyl ring having from 5 through 8 members, wherein said spacer pair is optionally substituted with one or more of the group consisting of $R^9$, $R^{10}$, $R^{11}$, $R^{12}$, and $R^{13}$;

$R^2$ and $R^{4a}$, $R^2$ and $R^{4b}$, $R^2$ and $R^{14}$ or $R^2$ and $R^{15}$ is optionally bonded together to form a heterocyclyl ring having from 5 through 8 members;

$R^2$ is optionally a spacer having from 2 through 5 atoms linked to the points of bonding of both $R^{4a}$ and $R^{4b}$ to form a heterocyclyl ring having from 5 through 8 members;

$Z^0$ is selected from the group consisting of a bond, $(CR^{41}R^{42})_q$ wherein q is an integer selected from 1 through 6, $(CH(R^{41}))_g$—$W^0$—$(CH(R^{42}))_p$ wherein g and p are integers independently selected from 0 through 3 and $W^0$ is selected from the group consisting of O, S, C(O), C(S), C(O)O, C(S)O, C(O)S, C(S)S, C(O)N($R^{41}$), ($R^{41}$)NC(O), C(S)N($R^{41}$), ($R^{41}$)NC(S), OC(O)N($R^{41}$), ($R^{41}$)NC(O)O, SC(S)N($R^{41}$), ($R^{41}$)NC(S)S, SC(O)N($R^{41}$), ($R^{41}$)NC(O)S, OC(S)N($R^{41}$), ($R^{41}$)NC(S)O, N($R^{42}$)C(O)N($R^{41}$), ($R^{41}$)NC(O)N($R^{42}$), N($R^{42}$)C(S)N($R^{41}$), ($R^{41}$)NC(S)N($R^{42}$), S(O), S(O)$_2$, S(O)$_2$N (R$^{41}$), N(R$^{41}$)S(O)$_2$, Se, Se(O), Se(O)$_2$, Se(O)$_2$N (R$^{41}$), N(R$^{41}$)Se(O)$_2$, P(O)(R$^8$), N(R$^7$)P(O)(R$^8$), P(O)(R$^8$)N(R$^7$), N(R$^{41}$), ON(R$^{41}$), and SiR$^{28}$R$^{29}$, and (CH (R$^{41}$))$_e$—W$^{22}$—(CH(R$^{42}$))$_h$ wherein e and h are integers independently selected from 0 through 2 and W$^{22}$ is selected from the group consisting of CR$^{41}$=CR$^{42}$, CR$^{41}$R$^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein W$^{22}$ is optionally substituted with one or more substituents selected from the group consisting of R$^9$, R$^{10}$, R$^{11}$, R$^2$, and R$^{13}$ and with the proviso that Z$^0$ is directly bonded to the pyridine ring;

R$^{28}$ and R$^{29}$ are independently selected from the group consisting of hydrido, hydroxyalkyl, alkyl, alkenyl, alkynyl, aryl, aralkyl, aryloxyalkyl, acyl, aroyl, aralkanoyl, heteroaroyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, arylsulfinylalkyl, arylsulfonylalkyl, aralkylsulfinyl, cycloalkylsulfinylalkyl, cycloalkylsufonylalkyl, heteroarylsulfonylalkyl, heteroarylsulfinylalkyl, aralkylsulfinylalkyl, aralkylsulfonylalkyl, carboxy, dialkoxyphosphono, diaralkoxyphosphono, dialkoxyphosphonoalkyl and diaralkoxyphosphonoalkyl;

R$^{28}$ and R$^{29}$ are optionally taken together to form a ring selected from the group consisting of a cycloalkyl ring having from 3 through 8 members, a cycloalkenyl ring having from 3 through 8 members, and a heterocyclyl ring having from 3 through 8 members;

Q is formula (II):

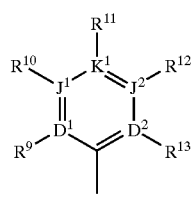

(II)

wherein D$^1$, D$^2$, J$^1$, J$^2$ and K$^1$ are independently selected from the group consisting of C, N, O, S and a bond with the provisos that no more than one can be a bond, no more than one of D$^1$, D$^2$, J$^1$, J$^2$ and K$^1$ can be O, no more than one of D$^1$, D$^2$, J$^1$, J$^2$ and K$^1$ can be S, one of D$^1$, D$^2$, J$^1$, J$^2$ and K$^1$ must be a bond when two of D$^1$, D$^2$, J$^1$, J$^2$ and K$^1$ are O and S, and no more than four of D$^1$, D$^2$, J$^1$, J$^2$ and K$^1$ can be N, with the provisos that D$^1$, D$^2$, J$^1$, J$^2$ and K$^1$ are selected to maintain an aromatic ring system and that R$^9$, R$^{10}$, R$^{11}$, R$^{12}$, and R$^{13}$ are each independently selected to maintain the tetravalent nature of carbon, trivalent nature of nitrogen, the divalent nature of sulfur, and the divalent nature of oxygen;

Q is optionally selected from formula (III):

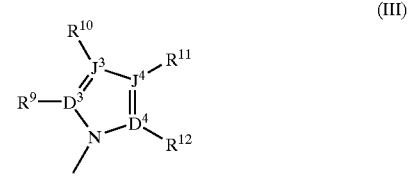

(III)

wherein D$^3$, D$^4$, J$^3$, and J$^4$ are independently selected from the group consisting of C, N, O, and S, no more than one of D$^3$, D$^4$, J$^3$, and J$^4$ is O, no more than one of D$^3$, D$^4$, J$^3$, and J$^4$ is S, and no more than three of D$^1$, D$^2$, J$^1$, and J$^2$ are N, with the provisos that D$^3$, D$^4$, J$^3$, and J$^4$ are selected to maintain an aromatic ring system and that R$^9$, R$^{10}$, R$^{11}$, and R$^{12}$ are each independently selected to maintain the tetravalent nature of carbon, trivalent nature of nitrogen, the divalent nature of sulfur, and the divalent nature of oxygen;

Q is optionally selected from the group consisting of hydrido, alkyl, alkoxy, alkylamino, alkylthio, haloalkylthio, alkenyl, alkynyl, saturated heterocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that Z$^0$ is selected from other than a bond when Q is hydrido;

K is (CR$^{4a}$R$^{4b}$)$_n$ wherein n is an integer selected from 1 through 4;

R$^{4a}$ and R$^{4b}$ are independently selected from the group consisting of halo, hydrido, hydroxy, cyano, hydroxyalkyl, alkyl, alkenyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, haloalkyl, haloalkenyl, heteroaryl, heteroarylalkyl, heteroarylthioalkyl, heteroaralkylthioalkyl, cyanoalkyl, alkylsulfinylalkyl, alkylsulfonylalkyl, haloalkylsulfinyl, arylsulfinylalkyl, arylsulfonylalkyl, heteroarylsulfonylalkyl, heteroarylsulfinylalkyl, aralkylsulfinylalkyl, and aralkylsulfonylalkyl with the proviso that halo, hydroxy, and cyano are bonded to different carbons when simultaneously present;

R$^{4a}$ and R$^{4b}$, when bonded to the same carbon, are optionally taken together to form a ring selected from the group consisting of a cycloalkyl ring having 3 through 8 members, a cycloalkenyl ring having 5 through 8 members, and a heterocyclyl ring having 5 through 8 members;

E$^0$ is E$^1$, when K is (CR$^{4a}$R$^{4b}$)$_n$, wherein E$^1$ is selected from the group consisting of a bond, O, S, C(O), C(S), C(O)O, C(S)O, C(O)S, C(S)S, C(O)N(R$^7$), (R$^7$)NC(O), C(S)N(R$^7$), (R$^7$)NC(S), OC(O)N(R$^7$), (R$^7$)NC(O)O, SC(S) N(R$^7$), (R$^7$)NC(S)S, SC(O)N(R$^7$), (R$^7$)NC(O)S, OC(S)N (R$^7$), (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N (R$^7$), N(R$^7$)S(O)$_2$, S(O)$_2$N(R$^7$)C(O), C(O)N(R$^7$)S(O)$_2$, Se, Se(O), Se(O)$_2$, Se(O)$_2$N(R$^7$), N(R$^7$)Se(O)$_2$, P(O)(R$^8$), N(R$^7$) P(O)(R$^8$), P(O)(R$^8$)N(R$^7$), N(R$^7$), ON(R$^7$), SiR$^{28}$R$^{29}$, CR$^{4a}$=CR$^{4b}$, ethynylidene (C≡C; 1,2-ethynyl), and C=CR$^{4a}$R$^{4b}$;

K is optionally selected to be $(CH(R^{14}))_j$—T wherein j is selected from a integer from 0 through 3 and T is selected from the group consisting of a bond, O, S, and $N(R^7)$ with the proviso that $(CH(R^{14}))_j$ is bonded to the pyridine ring;

$E^0$ is optionally $E^2$, when K is $(CH(R^{14}))_j$—T, wherein $E^2$ is selected from the group consisting of a bond, C(O), C(S), C(O)O, C(S)O, C(O)S, C(S)S, C(O)N(R$^7$), (R$^7$)NC(O), C(S)N(R$^7$), (R$^7$)NC(S), (R$^7$)NC(O)O, (R$^7$)NC(S)S, (R$^7$)NC(O)S, (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$S(O)$_2$N(R$^7$), N(R$^7$)S(O)$_2$, S(O)$_2$N(H)C(O), C(O)N(H)S(O)$_2$, Se(O), Se(O)$_2$, Se(O)$_2$N(R$^7$), N(R$^7$)Se(O)$_2$, P(O)(R$^8$), N(R$^7$)P(O)(R$^8$), P(O)(R$^8$)N(R$^7$), and N(R$^7$);

K is optionally selected to be G—$(CH(R^{15}))_k$ wherein k is selected from an integer from 1 through 3 and G is selected from the group consisting of O, S, and $N(R^7)$ with the proviso that $R^{15}$ is other than hydroxy, cyano, halo, amino, alkylamino, dialkylamino, and sulfhydryl when k is 1;

$E^0$ is optionally $E^3$ when K is G—$(CH(R^{15}))_k$ wherein $E^3$ is selected from the group consisting of a bond, O, S, C(O), C(S), C(O)O, C(S)O, C(O)S, C(S)S, C(O)N(R$^7$), (R$^7$)NC(O), C(S)N(R$^7$), (R$^7$)NC(S), OC(O)N(R$^7$), (R$^7$)NC(O)O, SC(S)N(R$^7$), (R$^7$)NC(S)S, SC(O)N(R$^7$), (R$^7$)NC(O)S, OC(S)N(R$^7$), (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N(R$^7$), N(R$^7$)S(O)$_2$, Se, Se(O), Se(O)$_2$, Se(O)$_2$N(R$^7$), N(R$^7$)Se(O)$_2$, P(O)(R$^8$), N(R$^7$)P(O)(R$^8$), P(O)(R$^8$)N(R$^7$), N(R$^7$), ON(R$^7$), SiR$^{28}$R$^{29}$, CR$^{4a}$=CR$^{4b}$, ethynylidene (C≡C; 1,2-ethynyl), and C=CR$^{4a}$R$^{4b}$;

$Y^0$ is formula (IV):

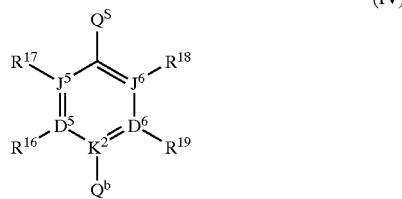

(IV)

wherein $D^5$, $D^6$, $J^5$, and $J^6$ are independently selected from the group consisting of C, N, O, S and a bond with the provisos that no more than one is a bond, $K^2$ is independently selected from the group consisting of C and $N^+$, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a bond when two of $D^5$, $D^6$, $J^5$, and $J^6$ are O and S, no more than three of $D^5$, $D^6$, $J^5$, and $J^6$ are N when $K^2$ is $N^+$, and no more than four of $D^5$, $D^6$, $J^5$, and $J^6$ are N when $K^2$ is carbon, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen and that $D^5$, $D^6$, $J^5$, and $J^6$ are selected to maintain an aromatic ring system;

$R^{16}$ and $R^{17}$ are independently optionally taken together to form a ring selected from the group consisting of a cycloalkenyl ring having from 5 through 8 members, a partially saturated heterocyclyl ring having from 5 through 8 members, a heteroaryl having from 5 through 6 members, and an aryl;

$R^{18}$ and $R^{19}$ are independently optionally taken together to form a ring selected from the group consisting of a cycloalkenyl ring having from 5 through 8 members, a partially saturated heterocyclyl ring having from 5 through 8 members, a heteroaryl having from 5 through 6 members, and an aryl;

$Q^b$ is selected from the group consisting of $NR^{20}R^{21}$, $^+NR^{20}R^{21}R^{22}$, oxy, alkyl, aminoalkyl, alkylamino, dialkylamino, dialkylsulfoniumalkyl, acylamino and hydrido, wherein $R^{20}$, $R^{21}$, and $R^{22}$ are independently selected from the group consisting of hydrido, amino, alkyl, hydroxy, alkoxy, aminoalkyl, alkylamino, dialkylamino, and hydroxyalkyl with the provisos that no more than one of $R^{20}$, $R^{21}$, and $R^{22}$ is hydroxy, alkoxy, alkylamino, amino, and dialkylamino at the same time and that $R^{20}$, $R^{21}$, and $R^{22}$ must be other than be hydroxy, alkoxy, alkylamino, amino, and dialkylamino when $K^2$ is $N^+$;

$R^{20}$ and $R^{21}$, $R^{20}$ and $R^{22}$, or $R^{21}$ and $R^{22}$ is optionally bonded together form a ring having from 4 through 7 atoms connecting the points of bonding of said spacer pair members to form a heterocyclyl ring having 5 through 8 members;

$Q^b$ is optionally selected from the group consisting of $N(R^{26})SO_2N(R^{23})(R^{24})$, $N(R^{26})C(O)OR^5$, $N(R^{26})C(O)SR^5$, $N(R^{26})C(S)OR^5$ and $N(R^{26})C(S)SR^5$ with the proviso that no more than one of $R^{23}$, $R^{24}$, and $R^{26}$ can be hydroxy, alkoxy, aminoalkyl, alkylamino, amino, or dialkylamino when two of the group consisting of $R^{23}$, $R^{24}$, and $R^{26}$ are bonded to the same atom;

$Q^b$ is optionally selected from the group consisting of dialkylsulfonium, trialkylphosphonium, $C(NR^{25})NR^{23}R^{24}$, $N(R^{26})C(NR^{25})N(R^{23})(R^{24})$, $N(R^{26})C(O)N(R^{23})(R^{24})$, $N(R^{26})C(S)N(R^{23})(R^{24})$, $C(NR^{25})OR^5$, $C(O)N(R^{26})C(NR^{25})N(R^{23})(R^{24})$, $C(S)N(R^{26})C(NR^{25})N(R^{23})(R^{24})$, $N(R^{26})N(R^{26})C(NR^{25})N(R^{23})(R^{24})$, $ON(R^{26})C(NR^{25})N(R^{23})(R^{24})$, $N(R^{26})N(R^{26})SO_2N(R^{23})(R^{24})$, $C(NR^{25})SR^5$, $C(O)NR^{23}R^{24}$, and $C(O)NR^{23}R^{24}$ with the provisos that no more than one of $R^{23}$, $R^{24}$, and $R^{26}$ can be hydroxy, alkoxy, alkylamino, amino, or dialkylamino when any two of the group consisting of $R^{23}$, $R^{24}$, and $R^{26}$ are bonded to the same atom and that said $Q^b$ group is bonded directly to a carbon atom;

$R^{23}$, $R^{24}$, $R^{25}$, and $R^{26}$ are independently selected from the group consisting of hydrido, alkyl, hydroxy, alkoxy, aminoalkyl, amino, alkylamino, dialkylamino, and hydroxyalkyl;

$R^{23}$ and $R^{24}$ are optionally bonded together to form a heterocyclyl ring having 5 through 8 members;

$R^{23}$ and $R^{25}$, $R^{24}$ and $R^{25}$, $R^{25}$ and $R^{26}$, $R^{24}$ and $R^{26}$, and $R^{23}$ and $R^{26}$ are independently optionally selected to form the group L—U—V wherein L, U, and V are independently selected from the group consisting of O, S, C(O), C(S), $C(J_H)_2S(O)$, $SO_2$, $OP(OR^{31})R^{30}$, $P(O)R^{30}$, $P(S)R^{30}$, $C(R^{30})R^{31}$, $C=C(R^{30})R^{31}$, $(O)_2POP(O)_2$, $R^{30}(O)POP(O)R^{30}$, $Si(R^{29})R^{28}$, $Si(R^{29})R^{28}Si(R^{29})R^{28}$, $Si(R^{29})R^{28}OSi(R^{29})R^{28}$, $(R^{28})R^{29}COC(R^{28})R^{29}$, $(R^{28})R^{29}CSC(R^{28})R^{29}$, $C(O)C(R^{30})=C(R^{31})$, $C(S)C(R^{30})C(R^{31})$, $S(O)C(R^{30})C(R^{31})$, $SO_2C(R^{30})=C(R^{31})$, $PR^{30}C(R^{30})=C(R^{31})$, $P(O)R^{30}C(R^{30})C(R^{31})$, $P(S)R^{30}C(R^{30})C(R^{31})$, $DC(R^{30})(R^{31})D$, $OP(OR^{31})R^{30}$, $P(O)R^{30}P(S)R^{30}$, $Si(R^{28})R^{29}$ and $N(R^{30})$, and a bond with the proviso that no more than any two of L, U and V are simultaneously covalent bonds and the heterocyclyl comprised of by L, U, and V has from 5 through 10 member;

D is selected from the group consisting of oxygen, C=O, C=S, $S(O)_m$ wherein m is an integer selected from 0 through 2;

$J_H$ is independently selected from the group consisting of $OR^{27}$, $SR^{27}$ and $N(R^{20})R^{21}$;

$R^{27}$ is selected from the group consisting of hydrido, alkyl, alkenyl, alkynyl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryloxyalkyl, heteroaryl, heteroarylalkyl, heteroarylthioalkyl, heteroaralkylthioalkyl, arylsulfinylalkyl, arylsulfonylalkyl, cycloalkylsulfinylalkyl, cycloalkylsufonylalkyl, heteroarylsulfonylalkyl, heteroarylsulfinylalkyl, aralkylsulfinylalkyl and aralkylsulfonylalkyl;

$R^{30}$ and $R^{31}$ are independently selected from the group consisting of hydrido, hydroxy, thiol, aryloxy, amino, alkylamino, dialkylamino, hydroxyalkyl, heteroaryloxyalkyl, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, haloaralkylsulfinylalkyl, aralkylsulfonylalkyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, sulfonylalkyl, alkoxysulfonylalkyl, aralkoxysulfonylalkyl, alkoxysulfonylalkoxy, aralkoxysulfonylalkoxy, sulfonylalkoxy, alkoxysulfonylalkylamino, aralkoxysulfonylalkylamino, and sulfonylalkylamino;

$R^{30}$ and $R^{31}$ are optionally taken to form a ring selected from the group consisting of a cycloalkyl ring having from 3 through 8 members, a cycloalkenyl ring having from 3 through 8 members, and a heterocyclyl ring having from 3 through 8 members;

$R^{23}$ and $R^{25}$, $R^{24}$ and $R^{25}$, $R^{25}$ and $R^{26}$, $R^{24}$ and $R^{26}$, or $R^{23}$ and $R^{26}$ is optionally bonded together to form the group L—U—V wherein L, U, and V are independently selected from the group of 1,2-disubstituted radicals consisting of a cycloalkyl radical, a cycloalkenyl radical wherein cycloalkyl and cycloalkenyl radicals are substituted with one or more groups selected from $R^{30}$ and $R^{31}$, an aryl radical, an heteroaryl radical, a saturated heterocyclic radical and a partially saturated heterocyclic radical wherein said 1,2-substitutents are independently selected from C=O, C=S, $C(R^{28})R^{32}$, S(O), S(O)$_2$, OP(OR$^{31}$)R$^{30}$, P(O)R$^{30}$, P(S)R$^{30}$ and Si(R$^{28}$)R$^{29}$;

$R^{23}$ and $R^{25}$, $R^{24}$ and $R^{25}$, $R^{25}$ and $R^{26}$, $R^{24}$ and $R^{26}$, or $R^{23}$ and $R^{26}$ is optionally bonded together to form the group L—U—V wherein L, U, and V are independently selected from the group of radicals consisting of 1,2-disubstituted alkylene radicals and 1,2-disubstituted alkenylene radical wherein said 1,2-substitutents are independently selected from C=O, C=S, $C(R^{28})R^{29}$, S(O), S(O)$_2$, OP(OR$^{31}$)R$^{30}$, P(O)R$^{30}$, P(S)R$^{30}$, and Si(R$^{28}$)R$^{29}$ and said alkylene and alkenylene radical are substituted with one or more $R^{30}$ or $R^{31}$ substituents;

$Q^s$ is selected from the group consisting of a bond, $(CR^{37}R^{38})_b$—$(W)_{az}$ wherein az is 0 or 1, b is an integer selected from 1 through 4, and $W^0$ is selected from the group consisting of O, S, C(O), C(S), C(O)O, C(S)O, C(O)S, C(S)S, C(O)N(R$^{14}$), (R$^{14}$)NC(O), C(S)N(R$^{14}$), (R$^{14}$)NC(S), OC(O)N(R$^{14}$), SC(S)N(R$^{14}$), SC(O)N(R$^{14}$), OC(S)N(R$^{14}$), OC(S)N(R$^{14}$), N(R$^{15}$)C(O)N(R$^{14}$), (R$^{14}$)NC(O)N(R$^{15}$), N(R$^{15}$)C(S)N(R$^{14}$), (R$^{14}$)NC(S)N(R$^{15}$), S(O), S(O)$_2$, S(O)$_2$N(R$^{14}$), N(R$^{14}$)S(O)$_2$, Se, Se(O), Se(O)$_2$, Se(O)$_2$N(R$^{17}$), N(R$^{14}$)Se(O)$_2$, P(O)(R$^8$), N(R$^7$)P(O)(R$^8$), P(O)(R$^8$)N(R$^7$), N(R$^{14}$), ON(R$^{14}$), and SiR$^{28}$R$^{29}$, (CH(R$^{14}$))$_c$—W$^1$—(CH(R$^{15}$))$_d$ wherein c and d are integers independently selected from 1 through 4, and W$^1$ is selected from the group consisting of O, S, C(O), C(S), C(O)O, C(S)O, C(O)S, C(S)S, C(O)N(R$^{14}$), (R$^{14}$)NC(O), C(S)N(R$^{14}$), (R$^{14}$)NC(S), OC(O)N(R$^{14}$), (R$^{14}$)NC(O)O, SC(S)N(R$^{14}$), (R$^{14}$)NC(S)S, SC(O)N(R$^{14}$), (R$^{14}$)NC(O)S, OC(S)N(R$^{14}$), (R$^{14}$)NC(S)O, N(R$^{15}$)C(O)N(R$^{14}$), (R$^{14}$)NC(O)N(R$^{15}$), N(R$^{15}$)C(S)N(R$^{14}$), (R$^{14}$)NC(S)N(R$^{15}$), S(O), S(O)$_2$, S(O)$_2$N(R$^{14}$), N(R$^{14}$)S(O)$_2$, Se, Se(O), Se(O)$_2$, Se(O)$_2$N(R$^{14}$), N(R$^{14}$)Se(O)$_2$, P(O)(R$^8$), N(R$^7$)P(O)(R$^8$), P(O)(R$^8$)N(R$^7$), N(R$^{14}$), ON(R$^{14}$), SiR$^{28}$R$^{29}$, and (CH(R$^{14}$))$_e$—W$^{22}$—(CH(R$^{15}$))$_h$ wherein e and h are integers independently selected from 0 through 2 and W$^{22}$ is selected from the group consisting of CR$^{41}$=CR$^{42}$, CR$^{41}$R$^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $(CR^{37}R^{38})_b$, $(CH(R^{14}))_c$, $(CH(R^{14}))_e$ and are bonded to E$^0$;

$R^{37}$ and $R^{37}$, when bonded to different carbons, are optionally taken together to form a ring selected from the group consisting of a cycloalkyl ring having from 3 through 8 members, a cycloalkenyl ring having from 3 through 8 members, and a heterocyclyl ring having from 3 through 8 members;

$R^{37}$ and $R^{38}$, when bonded to different carbons, are taken together to form a ring selected from the group consisting of a cycloalkyl ring having from 3 through 8 members, a cycloalkenyl ring having from 3 through 8 members, and a heterocyclyl ring having from 3 through 8 members;

$R^{38}$ and $R^{38}$, when bonded to different carbons, are taken together to form a ring selected from the group consisting of a cycloalkyl ring having from 3 through 8 members, a cycloalkenyl ring having from 3 through 8 members, and a heterocyclyl ring having from 3 through 8 members;

$R^{37}$ and $R^{38}$, when bonded to the same carbon, are taken together to form a group selected from a group consisting of oxo, thiono, alkylene, haloalkylene, and a ring selected from the group consisting of a cycloalkyl ring having from 3 through 8 members, a cycloalkenyl ring having from 3 through 8 members, and a heterocyclyl ring having from 3 through 8 members;

$Y^0$ is optionally $Y^{AT}$ wherein $Q^b$—$Q^s$;

$Y^0$ is optionally $Q^b$—$Q^{ss}$ wherein $Q^{ss}$ is selected from the group consisting of $(CR^{37}R^{38})_f$ wherein f is an integer selected from 1 through 6, $(CH(R^{14}))C$—W$^1$—(CH(R$^{15}$))$_d$ wherein c and d are integers independently selected from 1 through 4, and W$^1$ is selected from the group consisting of W$^1$ is selected from the group consisting of O, S, C(O), C(S), C(O)O, C(S)O, C(O)S, C(S)S, C(O)N(R$^{14}$), (R$^{14}$)NC(O), C(S)N(R , (R$^{14}$)NC(S), OC(O)N(R$^{14}$)(R$^{14}$)NC(O)O, SC(S)N(R$^{14}$), (R$^{14}$)NC(S)S, SC(O)N(R$^{14}$), (R$^{14}$)NC(O)S, OC(S)N(R$^{14}$), (R$^{14}$)NC(S) C, N(R$^{15}$)C(O)N(R$^{14}$), (R$^{14}$)NC (O)N(R$^{15}$), N(R$^{15}$)C(S)N(R$^{14}$), (R$^{14}$)NC(S)N(R$^{15}$), S(O), S(O)$_2$S(O)$_2$N(R$^{14}$), N(R$^{14}$)S(O)$_2$, Se, Se(O), Se(O)$_2$, Se(O)$_2$N(R$^{14}$), N(R$^{14}$)Se(O)$_2$, P(O)(R$^8$), N(R$^7$)P(O)(R$^8$), P(O)(R$^8$)N(R$^7$), N(R$^{14}$), ON(R$^{14}$), SiR$^{28}$R$^{29}$, and (CH(R$^{14}$))$_e$—W$^2$—(CH(R$^{15}$))$_h$ wherein e and h are integers independently selected from 0 through 2 and W$^2$ is selected from the group consisting of CR$^{4a}$=CR$^{4b}$, ethynylidene (C≡C; 1,2-ethynyl), and C=CR$^{4a}$R$^{4b}$ with the provisos that (CR$^{37}$R$^{38}$)$_f$(CH(R$^{15}$)), and (CH(R$^{15}$))$_e$ are bonded to E$^0$;

Y$^0$ is optionally Q$^b$—Q$^{sss}$, wherein Q$^{sss}$ is (CH(R$^{38}$))$_r$—W$^3$, r is an integer selected from 1 through 3, W$^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the W$^3$ other than the points of attachment is optionally substituted with one or more of the group consisting of R$^9$, R$^{10}$, R$^{11}$, and R$^{12}$, with the proviso that (CH(R$^3$))$_r$ is bonded to E$^0$ and Q$^b$ is bonded to lowest numbered substituent position of each W$^3$;

Y$^0$ is optionally Q$^b$—Q$^{sssr}$ wherein Q$^{sssr}$ is (CH(R$^{38}$))$_r$—W$^4$, r is an integer selected from 1 through 3, W$^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hydrido containing nitrogen member of the ring of the W$^4$ other than the points of attachment is optionally substituted with one or more of the group consisting of R$^9$, R$_{11}$, R$^{11}$, and R$^{12}$, with the provisos that (CH(R$^{38}$))$_r$ is bonded to E$^0$ and Q$^b$ is bonded to highest number substituent position of each W$^4$;

Y$^0$ is optionally Q$^b$—Q$^{ssss}$ wherein Q$^{ssss}$ is (CH(R$^{38}$))$_r$—W$^5$, r is an integer selected from 1 through 3, W$^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-imidazo(1,2-a)pyridinyl, 2,5-imidazo(1,2-a)pyridinyl, 2,6-imidazo(1,2-a)pyridinyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the W$^5$ other than the points of attachment is optionally substituted with one or more of the group consisting of R$^9$, R$^{10}$, R$^{11}$, and R$^{12}$, with the proviso that Q$^b$ is bonded to lowest number substituent position of each W$^5$ and that (CH(R$^{38}$))$_r$ is bonded to E$^0$;

Y$^0$ is optionally Q$^b$—Q$^{sssr}$ wherein Q$^{sssr}$ is (CH(R$^{38}$))$_r$—W$^6$, r is an integer selected from 1 through 3, W$^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-imidazo(1,2-a)pyridinyl, 2,5-imidazo(1,2-a)pyridinyl, 2,6-imidazo(1,2-a)pyridinyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^o$.

In an embodiment of compounds of Formula I or a pharmaceutically acceptable salt thereof, M is selected from the group consisting of N and N→O;
B is formula (V):

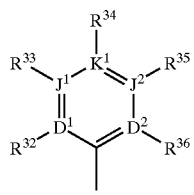

(V)

wherein $D^1$, $D^2$, $J^1$, $J^2$ and $K^1$ are independently selected from the group consisting of C, N, O, S and a bond with the provisos that no more than one is a bond, no more than one of $D^1$, $D^2$, $J^1$, $J^2$ and $K^1$ is O, no more than one of $D^1$, $D^2$, $J_1$, $J^2$ and $K^1$ is S, one of $D^1$, $D^2$, $J^1$, $J^2$ and $K^1$ must be a bond when two of $D^1$, $D$, $J^1$, $J^2$ and $K^1$ are O and S, and no more than four of $D^1$, $D^2$, $J^1$, $J^2$ and $K^1$ are N, with the provisos that $D^1$, $D^2$, $J^1$, $J^2$ and $K^1$ are selected to maintain an aromatic ring system and that $R^{32}$, $R^{33}$, $R^{34}$ $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$ $R^{35}$, and $R^{36}$ are independently selected from the group consisting of heterocyclylalkoxy, N-alkyl-N-arylamino, heterocyclylamino, heterocyclylalkylamino, hydrido, acetamido, haloacetamido, amidino, guanidino, dialkylsulfonium, trialkylphosphonium, dialkylsulfoniumalkyl, carboxy, heteroaralkylthio, haloalkylthio, alkanoyloxy, alkoxy, alkoxyalkyl, haloalkoxyalkyl, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl. haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkoxy, cycloalkylalkyl, cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$ and $R^{36}$ are independently optionally $Q^b$;

$R^{32}$ and $R^{33}$, $R^{33}$ and $R^{34}$, $R^{34}$ and $R^{35}$, or $R^{35}$ and $R^{36}$ is bonded together to form a ring selected from the group consisting of a cycloalkenyl ring having 5 through 8 members, a partially saturated heterocyclyl ring having 5 through 8 members, a heteroaryl ring having 5 through 6 members, and an aryl;

$R^9$ and $R^{10}$, $R^{10}$ and $R^{11}$, $R^{11}$ and $R^{12}$, or $R^{12}$ and $R^{13}$ is bonded together to form a ring selected from the group consisting of a cycloalkenyl ring having 5 through 8 members, a partially saturated heterocyclyl ring having 5 through 8 members, a heteroaryl ring having 5 through 6 members, and an aryl;

B is optionally selected from the group consisting of hydrido, trialkylsilyl, C2–C8 alkyl, C3–C8 alkylenyl, C3–C8 alkenyl, C3–C8 alkynyl, C2–C8 haloalkyl, and C3–C8 haloalkenyl wherein each member of group B may be optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C15 cycloalkyl, C5–C10 cycloalkenyl, C4–C12 saturated heterocyclyl, and C4–C9 partially saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

A is selected from the group consisting of a bond, $(W^7)_{rr}$—$(CH(R^{15}))_{pa}$ and $(CH(R^{15}))_{pa}$—$(W^7)_{rr}$ wherein rr is 0 or 1, pa is an integer selected from 0 through 6, and $W^7$ is selected from the group consisting of O, S, C(O), C(S), C(O)S, C(S)O, C(O)N($R^7$), C(S)N($R^7$)($R^7$)NC(O), ($R^7$)NC(S), S(O), S(O)$_2$, S(O)$_2$N($R^7$)($R^7$)NS(O)$_2$, P(O)($R^8$), N($R^7$)P(O)($R^8$), P(O)($R^8$)N($R^7$), C(N$R^7$)N($R^7$), ($R^7$)NC(N$R^7$)($R^7$)NC(N$R^7$)N$R^7$, and N($R^7$) with the proviso that no more than one of the group consisting of rr and pa is 0 at the same time;

$R^7$ and $R^8$ are independently selected from the group consisting of hydrido, hydroxy, alkyl, acyl, aroyl, heteroaroyl, and alkoxyalkyl;

$R^{14}$, $R^{15}$, $R^{37}$, and $R^{38}$ are independently selected from the group consisting of hydrido, hydroxy, halo, cyano, hydroxyalkyl, alkoxy, alkyl, alkoxyalkyl, cycloalkyl, cycloalkylalkyl, cycloalkenyl, cycloalkenylalkyl, haloalkyl, haloalkenyl, haloalkoxy, haloalkoxyalkyl, haloalkenyloxyalkyl, halocycloalkoxy, halocycloalkoxyalkyl, halocycloalkenyloxyalkyl, carboxy, carboxyalkyl, carboalkoxy, carboxamide, and carboxamidoalkyl;

$R^{14}$ and $R^{38}$ can be independently selected from the group consisting of acyl, aroyl, and heteroaroyl, wherein $R^{38}$ is optionally substituted at from one through three of the ring carbons with a substituent selected from the group consisting of $R^{16}$, $R^{17}$, $R^{18}$, and $R^{19}$;

Ψ is selected from the group consisting of N$R^5$, O, C(O), C(S), S, S(O), S(O)$_2$, ON($R^5$), P(O)($R^8$), and C$R^{39}R^{40}$;

$R^5$ is selected from the group consisting of hydrido, hydroxy, amino, alkyl, alkoxy, alkoxyalkyl, haloalkyl, acyl, aroyl, and heteroaroyl;

$R^{39}$ and $R^{40}$ are independently selected from the group consisting of hydrido, hydroxy, halo, cyano, hydroxyalkyl, acyl, aroyl, heteroaroyl, acylamido, alkoxy, alkyl, alkoxyalkyl, haloalkyl, haloalkoxy, haloalkoxyalkyl, alkylsulfonyl, haloalkylsulfonyl, carboxy, carboxyalkyl, carboalkoxy, carboxamide, and carboxamidoalkyl;

Ja is independently selected from the group consisting of N and C—X°;

Jb is independently selected from the group consisting of N and C—$R^1$;

Jc is independently selected from the group consisting of N and C—$R^2$;

$R^2$, $R^1$, and X° are independently selected from the group consisting of $Z^0$—Q, hydrido, alkyl, alkenyl, and halo;

$R^1$ and X° are independently optionally selected from the group consisting of amino, aminoalkyl, haloalkyl, haloalkoxy, haloalkylthio, amino, alkylamino, aminoalkyl, amidino, guanidino, hydroxy, hydroxyamino, alkoxy, hydroxyalkyl, alkoxyamino, thiol, alkylthio, dialkylsulfonium, trialkylphosphonium, dialkylsulfoniumalkyl, heteroarylamino, nitro, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$X^0$ and $R^1$ are optionally selected to be —W=X—Y=Z— wherein —W=X—Y=Z— forms a heteroaryl having 5 or 6 members or an aryl;

$R^1$ and $R^2$ are optionally selected to be—W=X—Y=Z— wherein —W=X—Y=Z— forms a heteroaryl ring having 5 or 6 members or an aryl;

W, X, Y, and Z are independently selected from the group consisting of C($R^9$), C($R^{10}$), C($R^{11}$), C($R^{12}$), N, N($R^{10}$) O, S and a bond with the proviso that W, X, Y, and Z are optionally and independently selected to be a bond wherein one of W, X, Y, and Z is selected from the group consisting of N, N($R^{10}$), O, and S, with the further proviso that no more than one of W, X, Y, and Z is optionally O or S, and with the still further proviso that no more than three of W, X, Y, and Z are optionally N or N($R^{10}$);

$X^0$ and $R^1$ or $R^1$ and $R^2$ is optionally bonded together to form a ring selected from the group consisting of a cycloalkenyl ring having from 5 through 8 members and a partially saturated heterocyclyl ring having from 5 through 8 members, wherein said spacer pair is optionally substituted with one or more of the group consisting of $R^9$, $R^{10}$, $R^{11}$, $R^{12}$, and $R^{13}$;

$R^2$ is $Z^0$—Q;

$Z^0$ is selected from the group consisting of a bond, $(CR^{41}R^{42})_q$ wherein q is an integer selected from 1 through 6, $(CH(R^{41}))_g$—$W^0$—$(CH(R^{42}))_p$ wherein g and p are integers independently selected from 0 through 3 and $W^0$ is selected from the group consisting of O, S, C(O), C(S), C(O)O, C(S)O, C(O)S, C(S)S, C(O)N($R^{41}$), ($R^{41}$)NC(O), C(S)N($R^{41}$), ($R^{41}$)NC(S), OC(O)N($R^{41}$), ($R^{41}$)NC(O)O, SC(S)N($R^{41}$), ($R^{41}$)NC(S)S, SC(O)N($R^{41}$), ($R^{41}$)NC(O)S, OC(S)N($R^{41}$), ($R^{41}$)NC(S)O, N($R^{42}$)C(O)N($R^{41}$), ($R^{41}$)NC(O)N($R^{42}$), N($R^{42}$)C(S)N($R^{41}$), ($R^{41}$)NC(S)N($R^{42}$), S(O), S(O)$_2$, S(O)$_2$N($R^{41}$), N($R^{41}$)S(O)$_2$Se, Se(O), Se(O)$_2$, Se(O)$_2$N($R^{41}$), N($R^{41}$)Se(O)$_2$, P(O)($R^8$), N($R^7$)P(O)($R^8$), P(O)($R^8$)N($R^7$), N($R^{41}$), ON($R^{41}$), and SiR$^{28}R^{29}$, and $(CH(R^{41}))_e$—$W^{22}$—$(CH(R^{42}))_h$ wherein e and h are integers independently selected from 0 through 2 and $W^{22}$ is selected from the group consisting of $CR^{41}$=$CR^{42}$, $CR^{41}R^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein $W^{22}$ is optionally substituted with one or more substituents selected from the group consisting of $R^9$, $R^{10}$, $R^{11}$, $R^{12}$, and $R^{13}$, and with the proviso that $Z^0$ is directly bonded to the pyridine ring;

$R^{41}$ and $R^{42}$ are independently selected from the group consisting of amidino, hydroxyamino, hydrido, hydroxy, amino, halo, cyano, aryloxy, hydroxyalkyl, acyl, aroyl, heteroaroyl, heteroaryloxyalkyl, alkoxy, alkyl, aryl, aralkyl, aryloxyalkyl, aralkoxyalkylalkoxy, alkoxyalkyl, heteroaryloxyalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroaralkyl, heteroarylthioalkyl, heteroaralkylthioalkyl, alkylsulfonyl, haloalkylsulfonyl, arylsulfonyl, arylsulfonylalkyl, aralkylsulfonyl, cycloalkylsulfonyl, cycloalkylsufonylalkyl, heteroarylsulfonylalkyl, heteroarylsulfonyl, and aralkylsulfonylal Q is formula (II):

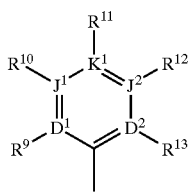

(II)

wherein $D^1$, $D^2$, $J^1$, $J^2$ and $K^1$ are independently selected from the group consisting of C, N, O, S and a bond with the provisos that no more than one is a bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a bond when two of $D^1$, $D^2$, $J^1$, $J^2$ and $K^1$ are O and S, and no more than four of $D^1$, $D^2$, $J^1$, $J^2$ and $K^1$ are N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

Q is optionally selected from formula (III):

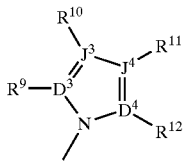

(III)

wherein $D^3$, $D^4$, $J^3$, and $J^4$ are independently selected from the group consisting of C, N, O, and S, no more than one of $D^3$, $D^4$, $J^3$, and $J^4$ is 0! no more than one of $D^3$, $D^4$, $J^3$, and $J^4$ is S, and no more than three of $D^1$, $D^2$, $J^1$, and $J^2$ are N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen and that $D^1$, $D^2$, $J^2$, $J^2$ and $K^1$ are selected to maintain an aromatic ring system;

Q is optionally selected from the group consisting of hydrido, alkyl, alkoxy, alkylamino, alkylthio, haloalkylthio, alkenyl, alkynyl, saturated heterocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that $Z^0$ is selected from other than a bond when Q is hydrido;

K is $(CR^{4a}R^{4b})_n$ wherein n is an integer selected from 1 through 2;

$R^{4a}$ and $R^{4b}$ are independently selected from the group consisting of halo, hydrido, hydroxy, cyano, hydroxyalkyl, alkyl, alkenyl, alkoxyalkyl, aralkyl, heteroaralkyl, alkylthioalkyl, haloalkyl, haloalkenyl, and cyanoalkyl;

$E^0$ is $E^1$, when K is $(CR^{4a}R^{4b})_n$, wherein $E^1$ is selected from the group consisting of a bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N($R^7$)C(O), C(O)N($R^7$)S(O)$_2$, P(O)($R^8$), N($R^7$)P(O)($R^8$), P(O)($R^8$)N($R^7$), N($R^7$), ON($R^7$), $CR^{4a}$=$CR^{4b}$, ethynylidene (C≡C; 1,2-ethynyl), and C=$CR^{4a}R^{4b}$;

K is optionally $(CH(R^{14}))_j$—T wherein j is selected from a integer from 0 through 2 and T is selected from the group consisting of a bond, O, S, and N($R^7$) with the proviso that $(CH(R^{14}))_j$ is bonded to the pyridine ring;

$E^0$ is optionally $E^2$, when K is $(CH(R^{14}))_j$—T, wherein $E^2$ is selected from the group consisting of a bond, C(O), C(S), C(O)O, C(S)O, C(O)S, C(S)S, C(O)N($R^7$), ($R^7$)NC(O), C(S)N($R^7$), ($R^7$)NC(S), ($R^7$)NC(O)O, ($R^7$)NC(S)S, ($R^7$)NC(O)S, ($R^7$)NC(S)O, N($R^8$)C(O)N($R^7$)($R^7$)NC(O)N($R^8$), N($R^8$)C(S)N($R^7$), ($R^7$)NC(S)N($R^8$), S(O), S(O)S(O)$_2$N($R^7$), N($R^7$)S(O)$_2$, S(O)$_2$N(H)C(O), C(O)N(H)S(O)$_2$, P(O)($R^8$), N($R^7$)P(O)($R^8$), P(O)($R^8$)N($R^7$) and N($R^7$);

K is optionally G—$(CH(R^{15}))_k$ wherein k is 1 or 2 and G is selected from the group consisting of O, S, and N(R);

$E^0$ is optionally $E^3$ when K is G—$(CH(R^{15}))_k$, wherein $E^3$ is selected from the group consisting of a bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N ($R^8$), N($R^8$)C(S)N($R^7$), ($R^7$)NC(S)N($R^8$), S(O), S(O)$_2$, S(O)$_2$ N($R^7$), N($R^7$)S(O)$_2$, P(O)($R^8$)N($R^7$)P(O)($R^8$), P(O) ($R^8$)N($R^7$), N($R^7$)ON($R^7$), $CR^{4a}$=$CR^{4b}$, ethynylidene (C°C; 1,2-ethynyl), and C=$CR^{4a}R^{4b}$;

$Y^0$ is formula (IV):

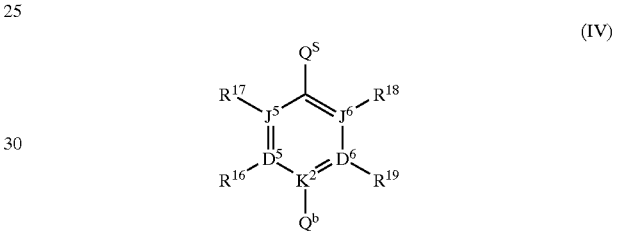

(IV)

wherein $D^5$, $D^6$, $J^5$, and $J^6$ are independently selected from the group consisting of C, N, O, S and a bond with the provisos that no more than one is a bond, $K^2$ is independently selected from the group consisting of C and $N^+$, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a bond when two of $D^5$, $D^6$, $J^5$, and $J^6$ are O and S, no more than three of $D^5$, $D^6$, $J^5$, and $J^6$ is N when $K^2$ is $N^+$, and no more than four of $D^5$, $D^6$, $J^5$, and $J^6$ are N when $K^2$ is carbon, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen and that $D^5$, $D^6$, $J^5$, and $J^6$ are selected to maintain an aromatic ring system;

$R^{16}$ and $R^{17}$ are optionally independently taken together to form a ring selected from the group consisting of a cycloalkenyl ring having from 5 through 8 members, a partially saturated heterocyclyl ring having from 5 through 8 members, a heteroaryl having from 5 through 6 members, and an aryl;

$Q^b$ is selected from the group consisting of $NR^{20}R^{21}$, $^+NR^{20}$, $R^{21}$, $R^{22}$, oxy, alkyl, aminoalkyl, alkylamino, dialkylamino, dialkylsulfoniumalkyl, acylamino. and hydrido, wherein $R^{20}$, $R^{21}$, and $R^{22}$ are independently selected from the group consisting of hydrido, amino, alkyl, hydroxy, alkoxy, aminoalkyl, alkylamino, dialkylamino, and hydroxyalkyl with the provisos that no more than one of $R^{20}$, $R^{21}$, and $R^{22}$ is hydroxy, alkoxy, alkylamino, amino, and dialkylamino at the same time and that $R^{20}$, $R^{21}$, and $R^{22}$ must be other than be hydroxy, alkoxy, alkylamino, amino, and dialkylamino when $K^2$ is $N^+$;

$R^{20}$ and $R^{21}$, $R^{20}$ and $R^{22}$, or $R^{21}$ and $R^{22}$ are optionally bonded together to form a heterocyclyl ring having 5 through 8 members;

$Q^b$ is optionally selected from the group consisting of $N(R^{26})SO_2N(R^{23})(R^{24})$, $N(R^{26})C(O)OR^5$, $N(R^{26})C(O)SR^5$, $N(R^{26})C(S)OR^5$ and $N(R^{26})C(S)SR^5$ with the proviso that no more than one of $R^{23}$, $R^{24}$, and $R^{26}$ is hydroxy, alkoxy, alkylamino, amino, and dialkylamino when two of the group consisting of $R^{23}$, $R^{24}$, and $R^{26}$ are bonded to the same atom;

$Q^b$ is optionally selected from the group consisting of dialkylsulfonium, trialkylphosphonium, $C(NR^{25})NR^{23}R^{24}$, $N(R^{26})C(NR^{25})N(R^{23})(R^{24})$, $N(R^{26})C(O)N(R^{23})(R^{24})$, $N(R^{26})C(S)N(R^{23})(R^{24})$, $C(NR^{25})OR^5$, $C(O)N(R^{26})C(NR^{25})N(R^{23})(R^{24})$, $C(S)N(R^{26})C(NR^{25})N(R^{23})(R^{24})$, $N(R^{26})N(R^{26})C(NR^{25})N(R^{23})(R^{24})$, $ON(R^{26})C(NR^{25})N(R^{23})(R^{24})$, $N(R^{26})N(R^{26})SO_2N(R^{23})(R^{24})$, $C(NR^{25})SR^5$, $C(O)NR^{23}R^{24}$, and $C(O)NR^{23}R^{24}$ with the provisos that no more than one of $R^{23}$, $R^{24}$, and $R^{26}$ can be hydroxy, alkoxy, alkylaminol, amino, or dialkylamino when two of the group consisting of $R^{23}$, $R^{24}$, and $R^{26}$ are bonded to the same atom and that said $Q^b$ group is bonded directly to a carbon atom;

$R^{23}$, $R^{24}$, $R^{25}$, and $R^{26}$ are independently selected from the group consisting of hydrido, alkyl, hydroxy, alkoxy, aminoalkyl, alkylamino, dialkylamino, amino, and hydroxyalkyl;

$R^{23}$ and $R^{24}$ are optionally taken together to form a linear spacer moiety having from 4 through 7 atoms connecting the points of bonding to form a heterocyclyl ring having 5 through 8 members;

$Q^s$ is selected from the group consisting of a bond, $(CR^{37}R^{38})_b$—$(W^0)_{az}$ wherein az is an integer selected from 0 through 1, b is an integer selected from 1 through 4, and $W^0$ is selected from the group consisting of O, S, C(O), C(S), C(O)O, C(S)O, C(O)S, C(S)S, C(O)N(R^{14}), (R^{14})NC(O), C(S)N(R^{14}), (R^{14})NC(S), OC(O)N(R^{14}), SC(S)N(R^{14}), SC(O)N(R^{14}), OC(S)N(R^{14}), N(R^{15})C(O)N(R^{14}), (R^{14})NC(O)N(R^{15}), N(R^{15})C(S)N(R^{14}), (R^{14})NC(S)N(R^{15}), S(O), S(O)_2, S(O)_2N(R^{14}), N(R^{14})S(O)_2, P(O)(R^8)N(R^7)P(O)(R^8), P(O)(R^8)N(R^7), N(R^{14}), ON(R^{14}), (CH(R^{14}))_c$—$W^1$—$(CH(R^{15}))_d$ wherein c and d are integers independently selected from 1 through 4, and $W^1$ is selected from the group consisting of O, S, C(O), C(S), C(O)O, C(S)O, C(O)S, C(S)S, C(O)N(R^{14}), (R^{14})NC(O), C(S)N(R^{14}), (R^{14})NC(S), OC(O)N(R^{14}), (R^{14})NC(O)O, SC(S)N(R^{14}), (R^{14})NC(S)S, SC(O)N(R^{14})(R^{14})NC(O)S, OC(S)N(R^{14}), (R^{14})NC(S)O, N(R^{15})C(O)N(R^{14}), (R^{14})NC(O)N(R^{15}), N(R^{15})C(S)N(R^{14}), (R^{14})NC(S)N(R^{15}), S(O), S(O)_2, S(O)_2N(R^{14}), N(R^{14})S(O), P(O)(R^8)N(R^7)P(O)(R^8), P(O)(R^8)N(R^7), N(R^{14}), ON(R^{14})$, and $(CH(R^{14}))_e$—$W^{22}$—$(CH(R^{15}))$ h wherein e and h are integers independently selected from 0 through 2 and $W^{22}$ is selected from the group consisting of $CR^{41}$=$CR^{42}{}_1$ $CR^{41}R^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $(CR^{37}R^{38})_b$, $(CH(R^{14}))_c$, and $(CH(R^{14}))_e$ are bonded to $E^0$;

$Y^0$ is optionally $Y^{AT}$ wherein $Y^{AT}$ is $Q^b$—$Q^s$;

$Y^0$ is optionally $Q^b$—$Q^{ss}$ wherein $Q^{ss}$ is selected from the group consisting of $(CR^{37}R^{38})_f$ wherein f is an integer selected from 1 through 6, $(CH(R^{14}))_c$—$W^1$—$(CH(R^{15}))_d$ wherein c and d are integers independently selected from 1 through 4, and $W^1$ is selected from the group consisting of $W^1$ is selected from the group consisting of O, S, C(O), C(S), C(O)O, C(S)O, C(O)S, C(S)S, C(O)N(R^{14}), (R^{14})NC(O), C(S)N(R^{14}), (R^{14})NC(S), OC(O)N(R^{14}), (R^{14})NC(O)O, SC(S)N(R^{14}), (R^{14})NC(S)S, SC(O)N(R^{14}), (R^{14})NC(O)S, OC(S)N(R^{14}), (R^{14})NC(S)O, N(R^{15})C(O)N(R^{14}), (R^{14})NC(O)N(R^{15}), N(R^{15})C(S)N(R^{14}), (R^{14})NC(S)N(R^{15}), S(O), S(O)_2, S(O)_2N(R^{14}), N(R^{14})S(O)_2, P(O)(R^8), N(R^7)P(O)(R^8), P(O)(R)N(R^7), N(R^{14}), ON(R^{14})$, and $(CH(R^{14}))_e$—$W^2$—$(CH(R^{15}))_h$ wherein e and h are integers independently selected from 0 through 2 and $W^2$ is selected from the group consisting of $CR^{4a}$=$CR^{4b}$, ethynylidene (C≡C; 1,2-ethynyl), and C=$CR^{4a}R^{4b}$ with the provisos that $(CR^{37}R^{38})_f$, $(CH(R^{14}))_c$, and $(CH(R^{14}))_e$ are bonded to $E^0$;

$Y^0$ is optionally $Q^b$—$Q^{sss}$ wherein $Q^{sss}$ is $(CH(R^{38}))_r$—$W^3$, r is an integer selected from 1 through 3, $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 2H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^3$ other than the points of attachment is optionally substituted with one or more of the group consisting of $R^9$, $R^{10}$, $R^{11}$, and $R^{12}$, with the proviso that $(CH(R^{38}))_r$ is bonded to $E^0$ and $Q^b$ is bonded to lowest numbered substituent position of each $W^3$;

$Y^0$ is optionally $Q^b$—$Q^{sssr}$ wherein $Q^{sssr}$ is $(CH(R^{38}))_r$—$W^4$, r is an integer selected from 1 through 3, $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,34-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hydrido containing nitrogen member of the ring of the $W^4$ other than the points of attachment is optionally substituted with one or more of the group consisting of $R^9$, $R^{10}$, $R^{11}$, and $R^{12}$, with the provisos that $(CH(R^{38}))_r$ is bonded to $E^0$ and $Q^b$ is bonded to highest number substituent position of each $W^4$;

$Y^0$ is optionally $Q^b$—$Q^{ssss}$ wherein $Q^{ssss}$ is $(CH(R^{38}))_r$—$W^5$, r is an integer selected from 1 through 3, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^5$ other than the points of attachment is optionally substituted with one or more of the group consisting of $R^9$, $R^{10}$, $R^{11}$, and $R^{12}$, with the provisos that $Q^b$ is bonded to lowest number substituent position of each $W^1$ and that $(CH(R^{38}))_r$ is bonded to $E^0$;

$Y^0$ is optionally $Q^b$—$Q^{sssssr}$ wherein $Q^{sssssr}$ is $(CH(R^{38}))_r$—$W^6$, r is an integer selected from 1 through 3, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^6$ other than the points of attachment is optionally substituted with one or more of the group consisting of $R^9$, $R^{10}$, $R^{11}$, and $R^{12}$, with the provisos that $Q^b$ is bonded to highest number substituent position of each $W^6$ and that $(CH(R^{38}))_r$ is bonded to $E^0$.

In another embodiment of compounds of Formula I or a pharmaceutically acceptable salt thereof, M is selected from the group consisting of N and N→O;

B is formula (V):

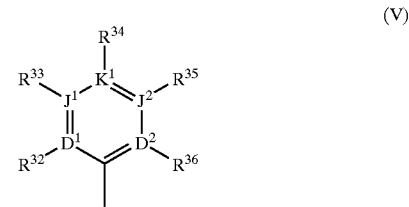

(V)

wherein $D^1$, $D^2$, $J^1$, $J^2$ and $K^1$ are independently selected from the group consisting of C, N, O, S and a bond with the provisos that no more than one is a bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a bond when two of $D^1$, $D^2$, $J^1$, $J^2$ and $K^1$ are O and S, and no more than four of $D^1$, $D^2$, $J^1$, $J^2$ and $K^1$ are N, with the provisos that $D^1$, $D^2$, $J^1$, $J^2$ and $K^1$ are selected to maintain an aromatic ring system and that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of heterocyclylalkoxy, N-alkyl-N-arylamino, heterocyclylamino, heterocyclylalkylamino, hydrido, acetamido, haloacetamido, amidino, guanidino, dialkylsulfonium, trialkylphosphonium, dialkylsulfoniumalkyl, carboxy, heteroaralkylthio, haloalkylthio, alkanoyloxy, alkoxy, alkoxyalkyl, haloalkoxyalkyl, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{36}$ are independently optionally $Q^b$;

B is optionally selected from the group consisting of hydrido, trialkylsilyl, C2–C8 alkyl, C3–C8 alkylenyl, C3–C8 alkenyl, C3–C8 alkynyl, C2–C8 haloalkyl, and C3–C8 haloalkenyl wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C12 cycloalkyl, C5–C10 cycloalkenyl, and C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

A is selected from the group consisting of a bond, $(W^7)_{rr}$—$(CH(R^{15}))_{pa}$ and $(CH(R^{15}))_{pa}$—$(W^7)_{rr}$ wherein rr is 0 or 1, pa is an integer selected from 0 through 6, and $W^7$ is selected from the group consisting of O, S, C(O), C(O)N($R^7$), C(S)N($R^7$), ($R^7$)NC(O), ($R^7$)NC(S), and N($R^7$) with the proviso that no more than one of the group consisting of rr and pa can be 0 at the same time;

$R^7$ and $R^8$ are independently selected from the group consisting of hydrido, hydroxy, alkyl, and alkoxyalkyl;

$R^{14}$, $R^{15}$, $R^{37}$, and $R^{38}$ are independently selected from the group consisting of hydrido, hydroxy, halo, alkyl, alkoxyalkyl, haloalkyl, haloalkoxy, and haloalkoxyalkyl;

$R^{14}$ and $R^{38}$ are optionally and independently selected from the group consisting of aroyl and heteroaroyl heteroaroyl, wherein $R^{38}$ is optionally substituted at from one through three of the ring carbons with a substituent selected from the group consisting of $R^{11}$, $R^{17}$, $R^{18}$, and $R^{19}$;

Ψ is selected from the group consisting of $NR^5$, C(O), and $S(O)_2$;

$R^5$ is selected from the group consisting of hydrido, hydroxy, alkyl, and alkoxy;

$R^{19}$ and $R^{40}$ are independently selected from the group consisting of hydrido, hydroxy, halo, hydroxyalkyl, alkyl, alkoxyalkyl, haloalkyl, haloalkoxy, and haloalkoxyalkyl;

Ja is independently selected from the group consisting of N and C—$X^o$;

Jb is independently selected from the group consisting of N and C—$R^1$;

Jc is independently selected from the group consisting of N and C—$R^2$;

$X^o$ and $R^1$ are independently selected from the group consisting of hydrido, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;

$X^o$ and $R^1$ or $R^1$ and $R^2$ is optionally —W=X—Y=Z— wherein —W=X—Y=Z— forms an aryl or C5–C6 heteroaryl;

W, X, Y, and Z are independently selected from the group consisting of $C(R^9)$, $C(R^{10})$, $C(R^{11})$, $C(R^{12})$N, $N(R^{10})$, O, S, and a bond with the proviso that one of W, X, Y, and Z is independently selected to be a bond when one of W, X, Y, and Z is O or S, with the further proviso that no more than one of W, X, Y, and Z is optionally O or S, and with the additional proviso that no more than three of W, X, Y, and Z are optionally N or $N(R^{10})$;

$X^o$ and $R^1$ or $R^1$ and $R^2$ is optionally bonded together to form C5–C8 cycloalkenyl ring or a partially saturated C5–C8 heterocyclyl ring, wherein said cycloalkenyl ring or heterocyclyl ring is optionally substituted with one or more of the group consisting of $R^9$, $R^{10}$, $R^{11}$, $R^{12}$, and $R^{13}$;

$R^2$ is $Z^0$—Q;

$Z^0$ is selected from the group consisting of a bond, $(CR^{41}R^{42})_q$ wherein q is an integer selected from 1 through 3, $(CH(R^{41}))_g$—$W^0$—$(CH(R^{42}))_p$ wherein g and p are integers independently selected from 0 through 3 and $W^0$ is selected from the group consisting of O, S, C(O), S(O), $S(O)_2$, $N(R^{41})$, and $ON(R^{41})$, and $(CH(R^{41}))_e$—$W^{22}$—$(CH(R^{42}))_h$ wherein e and h are integers independently selected from 0 through 2 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,4-tetrahydrofuranyl, 2,4-tetrahydrofuranyl, 2,5-tetrahydrofuranyl, and 3,4-tetrahydrofuranyl, wherein $W^{22}$ is optionally substituted with one or more substituents selected from the group consisting of $R^9$, $R^{10}$ $R^{11}$, $R^{12}$, and $R_{13}$, and with the proviso that $Z^0$ is directly bonded to the pyridine ring;

$R^{41}$ and $R^{42}$ are independently selected from the group consisting of amidino, hydroxyamino, hydrido, hydroxy, amino, and alkyl;

Q is selected from the group consisting of hydrido, with the proviso that $Z^0$ is other than a covalent single bond, the formula (II):

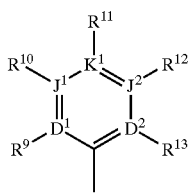

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ is N, with the provisos that $D^1$, $D^2$, $J^1$, $J^2$ and $K^1$ are selected to maintain an aromatic ring system and that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

K is $(CR^{4a}R^{4b})_n$ wherein n is 1 or 2;

$R^{4a}$ and $R^{4b}$ are independently selected from the group consisting of halo, hydrido, hydroxyalkyl, alkyl, alkoxyalkyl, alkylthioalkyl, and haloalkyl;

$E^0$ is selected from the group consisting of a bond, C(O), C(S), C(O)N($R^7$), ($R^7$)NC(O), S(O)$_2$, ($R^7$)NS(O)$_2$, and S(O)$_2$ N($R^7$);

$Y^0$ is formula (IV):

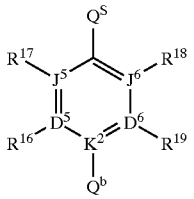

(IV)

wherein $D^5$, $D^6$, $J^5$, and $J^6$ are independently selected from the group consisting of C, N, O, S and a bond with the provisos that no more than one is a bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a bond when two of $D^5$, $D^6$, $J^5$, and $J^6$ are Q and S, and no more than four of $D^5$, $D^6$, $J^5$, and $J^6$ are N when $K^2$ is carbon, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen and that $D^5$, $D^6$, $J^5$, and $J^6$ are selected to maintain an aromatic ring system;

$Q^b$ is selected from the group consisting of NR$^{20}$R$^{21}$, $^+$NR$^{20}$R$^{21}$R$^{22}$, aminoalkyl, and hydrido, wherein $R^{20}$, $R^{21}$, and $R^{22}$ are independently selected from the group consisting of hydrido, alkyl, hydroxy, amino, aminoalkyl, dialkylamino, alkylamino, and hydroxyalkyl with the proviso that no more than one of $R^{20}$ and $R^{21}$ is selected from the group consisting of hydroxy, amino, alkylamino, and dialkylamino at the same time;

$Q^b$ is optionally selected from the group consisting of C(NR$^2$)NR$^{23}$R$^{24}$, N(R$^{26}$)C(NR$^{25}$)N(R$^{23}$)(R$^{24}$), and C(O)N(R$^{26}$)C(NR$^{25}$)N(R$^{23}$)(R$^{24}$), N(R$^{26}$)N(R$^{26}$)C(NR$^{25}$)N(R$^{23}$)(R$^{24}$), and ON(R$^{26}$)C(NR$^{25}$)N(R$^{23}$)(R$^{24}$) with the provisos that no more than one of $R^{23}$, $R^{24}$, and $R^{26}$ is selected from the group consisting of hydroxy, amino, alkylamino, and dialkylamino when two of the group consisting of $R^{23}$, $R^{24}$, and $R^{26}$ are bonded to the same atom;

$R^{23}$, $R^{24}$, $R^{25}$, and $R^{26}$ are independently selected from the group consisting of hydrido, alkyl, hydroxy, amino, aminoalkyl, dialkylamino, alkylamino, and hydroxyalkyl;

$Q^s$ is selected from the group consisting of a bond, $(CR^{37}R^{38})_b$—$(W^0)_{az}$ wherein az is 0 or 1, b is an integer selected from 1 through 5, and $W^0$ is selected from the group consisting of O, C(O), S(O), S(O)$_2$, S(O)$_2$N(R$^{14}$), N(R$^{14}$)S(O)$_2$, and N(R$^{14}$), (CH(R$^{14}$))$_c$—W$^1$—(CH(R$^{15}$))$_d$ wherein c and d are integers independently selected from 1 through 4 and $W^1$ is selected from the group consisting of O, S, C(O), C(S), C(O)O, C(S)O, C(O)S, C(S)S, C(O)N(R$^{14}$), (R$^{14}$)NC(O), C(S)N(R$^{14}$), (R$^{14}$)NC(S), OC(O)N(R$^{14}$), (R$^{14}$)NC(O)O, SC(S)N(R$^{14}$)(R$^{14}$)NC(S)S, SC(O)N(R$^{14}$), (R$^{14}$)NC(O)S, OC(S)N(R$^{14}$), (R$^{14}$)NC(S)O, N(R$^{15}$)C(O)N(R$^{14}$), (R$^{14}$)NC(O)N(R$^{15}$), N(R$^{15}$)C(S)N(R$^{14}$), (R$^{14}$)NC(S)N(R$^{15}$), S(O), S(O)$_2$S(O)$_2$N(R$^{14}$), N(R$^{14}$)S(O)$_2$, P(O)(R$^8$)N(R$^7$)P(O)(R$^8$), P(O)(R$^8$)N(R$^7$), N(R$^{14}$), ON(R$^{14}$), and (CH(R$^{14}$))$_e$—W$^{22}$—(CH(R$^{15}$))$_h$ wherein e and h are integers independently selected from 0 through 2 and $W^{22}$ is selected from the group consisting of CR$^{41}$=CR$^{42}$, CR$^{41}$R$^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $(CR^{37}R^{38})_b$, (CH(R$^{14}$))$_c$, and (CH(R$^{14}$))$_e$ are bonded to $E^0$;

$Y^0$ is optionally $Y^{AT}$ wherein $Y^{AT}$ is $Q^b$—$Q^s$;

$Y^0$ is optionally $Q^b$—$Q^{ss}$ wherein $Q^{ss}$ is selected from the group consisting of $(CR^{37}R^{38})_f$ wherein f is an integer selected from 1 through 4, (CH(R$^{14}$))$_c$—W$^1$—(CH(R$^{15}$))$_d$ wherein c and d are integers independently selected from 1 through 2, and $W^1$ is selected from the group consisting of $W^1$ is selected from the group consisting of O, S, C(O), C(O)N(R$^{14}$), (R$^{14}$)NC(O), N(R$^{15}$)C(O)N(R$^{14}$), (R$^{14}$)NC(O)N(R$^{15}$), N(R$^{14}$), ON(R$^{14}$), and (CH(R$^{14}$))$_e$—W$^2$—(CH(R$^{15}$))$_h$ wherein e and h are integers independently selected from 0 through 2 and $W^2$ is selected from the group consisting of CR$^{4a}$=CR$^{4b}$, ethynylidene (C≡C; 1,2-ethynyl), and C=CR$^{4a}$R$^{4b}$ with the provisos that $(CR^{37}R^{38})_f$, (CH(R$^{14}$))$_c$, and (CH(R$^{14}$))$_e$ are bonded to $E^0$;

$Y^0$ is optionally $Q^b$—$Q^{sss}$ wherein $Q^{sss}$ is $(CH(R^3))_r$—$W^3$, r is an integer selected from 1 through 2, $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^3$ other than the points of attachment is optionally substituted with one or more of the group consisting of $R^9$, $R^{10}$, $R^{11}$, and $R^2$, with the proviso that $(CH(R^33))_r$ is bonded to $E^0$ and $Q^b$ is bonded to lowest numbered substituent position of each $W^3$;

$Y^0$ is optionally $Q^b$—$Q^{ssss}$ wherein $Q^{ssss}$ is $(CH(R^{38}))$—$W^4$, r is an integer selected from 1 through 2, $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^4$ other than the points of attachment is optionally substituted with one or more of the group consisting of $R^9$, $R^{10}$, $R^{11}$, and $R^{12}$, with the provisos that $(CH(R^{38}))_r$ is bonded to $E^0$ and $Q^b$ is bonded to highest number substituent position of each $W^4$;

$Y^0$ is optionally $Q^b$—$Q^{ssss}$ wherein $Q^{ss}$ SS is $(CH(R^{38}))_r$—$W^5$, r is an integer selected from 1 through 2, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^0$;

$Y^0$ is optionally $Q^b$—$Q^{ssssr}$ wherein $Q^{ssssr}$ is $(CH(R^{38}))_r$—$W^6$, r is an integer selected from 1 through 2, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In a preferred embodiment of a compound of Formula I, said compound is the Formula:

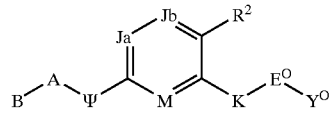

or a pharmaceutically acceptable salt thereof, wherein;

M is N or N→O;

B is phenyl or a heteroaryl of 5 or 6 ring members, wherein a nitrogen with a removable hydrogen or a carbon adjacent to the carbon at the point of attachment of said phenyl or heteroaryl ring to A is optionally substituted by $R^{32}$, a nitrogen with a removable hydrogen or a carbon at the other position adjacent to the point of attachment is optionally substituted by $R^{36}$, a nitrogen with a removable hydrogen or a carbon adjacent to $R^{32}$ and two atoms from the point of attachment is optionally substituted by $R^{33}$, a nitrogen with a removable hydrogen or a carbon adjacent to $R^{36}$ and two atoms from the point of attachment is optionally substituted by $R^{35}$, and a nitrogen with a removable hydrogen or a carbon adjacent to both $R^{33}$ and $R^{35}$ is optionally substituted by $R^{34}$;

$R^9$, $R^{10}$, $R^{11}$, $R^{12}$, $R^{13}$, $R^{32}$, $R^{33}$, $R^{34}$, $R^{35}$, and $R^3$ are independently selected from the group consisting of hydrido, acetamido, haloacetamido, amidino, guanidino, alkylenedioxy, haloalkylthio, alkanoyloxy, alkoxy, cycloalkoxy, cycloalkylalkoxy, aralkoxy, aryloxy, heteroaryloxy, heteroaralkoxy,heterocyclyloxy, heterocyclylalkoxy, alkoxyalkyl, haloalkoxyalkyl, hydroxy, amino, alkoxyamino, nitro, alkylamino, N-alkyl-N-arylamino, arylamino, aralkylamino, heteroarylamino, heteroaralkylamino, heterocyclylamino, heterocyclylalkylamino, alkylthio, alkylthioalkyl, alkylsulfinyl, arylsulfinyl, aralkylsulfinyl, cycloalkylsulfinyl, heteroarylsulfinyl, alkylsulfonyl, arylsulfonyl, aralkylsulfonyl, cycloalkylsulfonyl, heteroarylsulfonyl, alkylsulfonylalkyl, aryl, aralkyl, cycloalkyl, cycloalkylalkyl, heteroaryl, heterocyclyl, alkylsulfonamido, amidosulfonyl, alkanoyl, haloalkanoyl, alkyl, alkenyl, halo, haloalkyl, haloalkenyl, haloalkoxy, hydroxyhaloalkyl, hydroxyalkyl, aminoalkyl, haloalkoxyalkyl, carboxyalkyl, carboalkoxy, carboxy, carboxamido, carboxamidoalkyl, and cyano;

$R^{32}$, $R^{33}$, $R^{34}$, $R^{35}$, and $R^{36}$ are independently optionally $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C12 cycloalkyl or C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen atom adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

A is selected from the group consisting of a bond, $(W^7)_{rr}$—$(CH(R^{15}))_{pa}$, and $(CH(R^{15}))_{pa}$—$(W^7)_{rr}$ wherein rr is 0 or 1, pa is an integer selected from 0 through 6, and $W^7$ is selected from the group consisting of O, S, C(O), $(R^7)$NC(O), $(R^7)$NC(S), and $N(R^7)$ with the proviso that no more than one of the group consisting of rr and pa is 0 at the same time;

$R^7$ is selected from the group consisting of hydrido, hydroxy, and alkyl;

$R^{15}$ is selected from the group consisting of hydrido, hydroxy, halo, alkyl, and haloalkyl;

$\Psi$ is NH or NOH;

Ja is N or C—$X^0$;

Jb is N or C—$R^1$;

$X^0$ and $R^1$ are independently selected from the group consisting of hydrido, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;

$X^0$ and $R^1$ or $R^1$ and $R^2$ is optionally —W=X—Y=Z— wherein —W=X—Y=Z— forms an aryl or C5–C6 heteroaryl;

W, X, Y, and Z are independently selected from the group consisting of $C(R^9)$, $C(R^{10})$, $C(R^{11})C(R^{12})$, N, $N(R^{10})$, O, S, and a bond with the proviso that one of W, X, Y, and Z is independently selected to be a bond when one of W, X, Y, and Z is O or S, with the further proviso that no more than one of W, X, Y, and Z is optionally O or S, and with the additional proviso that no more than three of W, X, Y, and Z are optionally N or $N(R^{10})$;

$X^0$ and $R^1$ or $R^1$ and $R^2$ is optionally bonded together to form C5–C8 cycloalkenyl ring or a partially saturated C5–C8 heterocyclyl ring, wherein said cycloalkenyl ring or heterocyclyl ring is optionally substituted with one or more of the group consisting of $R^9$, $R^{10}$, $R^{11}$, $R^{12}$, and $R^{13}$;

$R^2$ is $Z^0$—Q;

$Z^0$ is selected from the group consisting of a bond, $(CR^{41}R^{42})_q$ wherein q is an integer selected from 1 through 3, and $(CH(R^{41}))_g$—$W^0$—$(CH(R^{42}))_p$ wherein g and p are integers independently selected from 0 through 3 and $W^1$ is selected from the group consisting of O, S, C(O), S(O), $N(R^{41})$, and $ON(R^{41})$;

$Z^0$ is optionally $(CH(R^{41}))_e$—$W^{22}$—$(CH(R^{42}))_h$ wherein e and h are independently 0 or 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein $Z^0$ is directly bonded to the pyridine ring and $W^{22}$ is optionally substituted with one or more substituents selected from the group consisting of $R^9$, $R^{10}$, $R^{11}$, $R^{12}$, and $R^{13}$;

$R^{41}$ and $R^{42}$ are independently selected from the group consisting of amidino, hydroxyamino, hydrido, hydroxy, amino, and alkyl;

Q is phenyl or a heteroaryl of 5 or 6 ring members, wherein a nitrogen with a removable hydrogen or a carbon adjacent to the carbon at the point of attachment of said phenyl or heteroaryl ring to $Z^0$ is optionally substituted by $R^9$, a nitrogen with a removable hydrogen or a carbon at the other position adjacent to the point of attachment is optionally substituted by $R^{13}$, a nitrogen with a removable hydrogen or a carbon adjacent to $R^9$ and two atoms from the point of attachment is optionally substituted by $R^{10}$, a nitrogen with a removable hydrogen or a carbon adjacent to $R^{13}$ and two atoms from the point of attachment is optionally substituted by $R^{12}$, and a nitrogen with a removable hydrogen or a carbon adjacent to both $R^{10}$ and $R^{12}$ is optionally substituted by $R^{11}$;

Q is optionally hydrido with the proviso that $Z^o$ is selected from other than a bond;

K is $CR^{4a}R^{4b}$;

$R^{4a}$ and $R^{4b}$ are independently selected from the group consisting of halo, hydrido, hydroxyalkyl, alkyl, alkoxyalkyl, alkylthioalkyl, and haloalkyl;

$E^o$, with the proviso that K is $CR^{4a}R^{4b}$, is $E^1$ wherein $E^1$ is selected from the group consisting of a covalent single bond, C(O)N(H), (H)NC(O), C(S)N(H), (H)NC(S), S(O)$_2$N(H), N(H)S(O)$_2$, S(O)$_2$N(H)C(O), and C(O)N(H)S(O)$_2$;

K is optionally $(CH(R^{14}))_j$—T wherein j is 0 or 1 and T is a bond or $N(R^7)$ with the proviso that $(CH(R^{14}))_j$ is bonded to the phenyl ring;

$R^{14}$ is selected from the group consisting of hydrido, halo, alkyl, and haloalkyl;

$E^o$, with the proviso that K is $(CH(R^{14}))_j$—T, is $E^2$ wherein $E^2$ is selected from the group consisting of C(O)N(H), (H)NC(O), C(S)N(H), (H)NC(S), S(O)$_2$N(H), N(H)S(O)$_2$, S(O)$_2$N(H)C(O), and C(O)N(H)S(O)$_2$;

$Y^o$ is phenyl or a heteroaryl of 5 or 6 ring members, wherein one carbon of said phenyl or said heteroaryl is substituted by $Q^s$, a carbon two or three contiguous atoms from the point of attachment of $Q^s$ to said phenyl or said heteroaryl to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, nitro, alkoxyamino, alkylamino, alkylthio, alkylsulfinyl, alkylsulfonyl, alkanoyl, haloalkanoyl, alkyl, alkenyl, halo, haloalkyl, haloalkoxy, hydroxyalkyl, aminoalkyl, haloalkoxyalkyl, carboalkoxy, and cyano;

$R^{16}$ or $R^{19}$ is optionally selected from the group consisting of $NR^{20}R^{21}$, $N(R^{26})C(NR^{25})N(R^{22})(R^{24})$, and $C(NR^{25})NR^{23}R^{24}$, with the proviso that $R^{16}$, $R^{19}$, and $Q^b$ are not simultaneously hydride;

$Q^b$ is selected from the group consisting of $NR^{20}R^{21}$, aminoalkyl, hydride, $N(R^{26})C(NR^{25})N(R^{24})$, and $C(NR^{25})NR^{23}R^{24}$, with the proviso that no more than one of $R^{20}$ and $R^{21}$ is selected from the group consisting of hydroxy, amino, alkylamino, and dialkylamino at the same time, with the further proviso that no more than one of $R^{23}$ and $R^{24}$ is selected from the group consisting of hydroxy, amino, alkylamino, and dialkylamino at the same time;

$R^{20}$, $R^{21}$, $R^{23}$, $R^{24}$, $R^{25}$ and $R^{26}$ are independently selected from the group consisting of hydrido, alkyl, hydroxy, aminoalkyl, amino, dialkylamino, alkylamino, and hydroxyalkyl;

$Q^s$ is selected from the group consisting of a bond, $(CR^{37}R^{38})_b$ wherein b is an integer selected from 1 through 4, and $(CH(R^{14})_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, S(O), S(O)$_2$, S(O)$_2$N(R$^{14}$), N(R$^{14}$)S(O)$_2$, and N(R$^{14}$), with the proviso that $R^{14}$ is selected from other than halo when directly bonded to N, and with the additional proviso that $(CR^{37}R^{38})_b$ and $(CH(R^{14}))_c$ are bonded to $E^o$;

$R^{37}$ and $R^{38}$ are independently selected from the group consisting of hydride, alkyl, and haloalkyl;

$R^{38}$ is optionally aroyl or heteroaroyl, wherein $R^{38}$ is optionally substituted with one or more substituents selected from the group consisting of $R^{16}$, $R^{17}$, $R^{18}$, and $R^{19}$;

$Y^o$ is optionally $Y^{AT}$ wherein $Y^{AT}$ is $Q^b$—$Q^s$;

$Y^o$ is optionally $Q^b$ $Q^{ss}$ wherein $Q^{ss}$ is $(CH(R^{14}))_e$—$W^2$—$(CH(R^{15}))_h$ wherein e and h are independently 1 or 2 and $W^2$ is $CR^{4a}$=$CR^{4b}$, with the proviso that $(CH(R^{14}))_e$ is bonded to $E^o$.

In a more preferred embodiment of a compound of Formula I, said compound is the Formula:

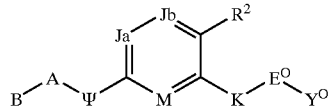

or a pharmaceutically acceptable salt thereof, wherein;

M is N or N→O;

B is phenyl or a heteroaryl of 5 or 6 ring members, wherein a carbon adjacent to the carbon at the point of attachment of said phenyl or heteroaryl ring to A is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, haloalkanoyl, nitro, alkylamino, alkylthio, aryl, aralkyl, cycloalkyl, cycloalkylalkyl, heteroaryl, heterocyclyl, alkylsulfonamido, amidosulfonyl, alkyl, alkenyl, halo, haloalkyl, haloalkenyl, haloalkoxy, hydroxyalkyl, hydroxyhaloalkyl, aminoalkyl, carboalkoxy, carboxy, carboxamido, cyano, and $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^3$;

B is optionally a C3–C12 cycloalkyl or a C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

$R^9$, $R_{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkylamino, N-alkyl-ON-arylamino, arylamino, aralkylamino, heteroarylamino, heteroaralkylamino, heterocyclylamino, heterocyclylalkylamino, alkylthio, alkylsulfinyl, arylsulfinyl, aralkylsulfinyl, cycloalkylsulfinyl, heteroarylsulfinyl, alkylsulfamido, alkylsulfonyl, arylsulfonyl, aralkylsulfonyl, cycloalkylsulfonyl, heteroarylsulfonyl, amidosulfonyl, alkyl, aryl, aralkyl, cycloalkyl, cycloalkylalkyl, heteroaryl, heterocyclyl, halo, haloalkyl, haloalkoxy, hydroxyalkyl, hydroxyhaloalkyl, aminoalkyl, carboalkoxy, carboxy, carboxyalkyl, carboxamido, and cyano;

A is a bond or $(CH(R^{15}))_{pa}$—$(W^7)_{rr}$ wherein rr is 0 or 1, pa is an integer selected from 0 through 3, and $W^7$ is selected from the group consisting of O, S, C(O), $(R^7)NC(O)$, $(R^7)NC(S)$, and $N(R^7)$, with the proviso that $W^7$ is bonded to the N(H) on the pyridine ring;

$R^7$ is selected from the group consisting of hydrido, hydroxy and alkyl;

$R^{15}$ is selected from the group consisting of hydrido, hydroxy, halo, alkyl, and haloalkyl;

Ja is N or C—$X^0$;

Jb is N or C—$R^1$;

$R^1$ and $X^0$ are independently selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$X^0$ and $R^1$ or $R^1$ and $R^2$ is optionally —W=X—Y=Z— wherein —W=X—Y=Z— forms an aryl or heteroaryl of 5 or 6 ring-members;

W, X, Y, and Z are independently selected from the group consisting of $C(R^9)$, $C(R^{10})$, $C(R^{11})$, $C(R^{12})$, N, $N(R^{10})$, O, S and a bond with the proviso that one of W, X, Y, and Z is independently selected to be a bond when one of W, X, Y, and Z is O or S, with the further proviso that no more than one of W, X, Y, and Z is optionally selected from the group consisting of O and S, and with the additional proviso that no more than three of W, X, Y, and Z are optionally N or $N(R^{10})$;

$X^0$ and $R^1$ or $R^1$ and $R^2$ is optionally bonded together to form C5–C8 cycloalkenyl ring or a partially saturated C5–C8 heterocyclyl ring, wherein said cycloalkenyl ring or heterocyclyl ring is optionally substituted with one or more of the group consisting of $R^9$, $R_{10}$, $R^{11}$, $R^{12}$, and $R^{13}$; $R^2$ is $Z^0$—Q;

$Z^0$ is selected from the group consisting of a bond, $(CR^{41}R^{42})_q$ wherein q is 1 or 2, and $(CH(R^{41}))_g$—$W^0$—$(CH(R^{42}))_p$ wherein g and p are integers independently selected from 0 through 3 and $W^0$ is selected from the group consisting of O, S, C(O), S(O), $N(R^{41})$, and $ON(R^{41})$;

$Z^0$ is optionally $(CH(R^{41}))_e$—$W^{22}$—$(CH(R^{42}))_h$ wherein e and h are independently 0 or 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein $Z^0$ is directly bonded to the pyridine ring and $W^{22}$ is optionally substituted with one or more substituents selected from the group consisting of $R^9$, $R^{10}$, $R^{11}$, $R^{12}$, and $R^{13}$;

$R^{41}$ and $R^{42}$ are independently selected from the group consisting of hydrido, hydroxy, alkyl, and amino;

Q is phenyl or a heteroaryl of 5 or 6 ring members, wherein a carbon adjacent to the carbon at the point of attachment of said phenyl or heteroaryl ring to $Z^0$ is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to R13 and two atoms from the carbon at the point of attachment is optionally substituted by $R^{12}$, and any carbon adjacent to both $R^{10}$ and $R^{12}$ is optionally substituted by $R^{11}$;

Q is optionally hydrido with the proviso that $Z^0$ is other than a bond;

K is $CR^{4a}R^{4b}$;

$R^{4a}$ and $R^{4b}$ are independently selected from the group consisting of hydrido, hydroxyalkyl, alkyl, alkoxyalkyl, alkylthioalkyl, and haloalkyl;

$E^0$, with the proviso that K is $CR^{4a}R^{4b}$, is $E^1$ wherein $E^1$ is selected from the group consisting of a covalent single bond, C(O)N(H), (H)NC(O), $S(O)_2N(H)$, and $N(H)S(O)_2$;

K is optionally $(CH(R^{14}))_j$—T wherein j is 0 or 1 and T is a bond or $N(R^7)$ with the proviso that $(CH(R^{14}))_j$ is bonded to the phenyl ring;

$R^{14}$ is hydrido or halo;

$E^0$, with the proviso that K is $(CH(R^{14}))_j$—T, is $E^2$ wherein $E^2$ is selected from the group consisting of C(O)N(H), (H)NC(O), C(S)N(H), (H)NC(S), $S(O)_2N(H)$, $N(H)S(O)_2$, $S(O)_2N(H)C(O)$, and $C(O)N(H)S(O)_2$;

$Y^0$ is phenyl or a heteroaryl of 5 or 6 ring members, wherein one carbon of said phenyl or said heteroaryl is substituted by $Q^s$, a carbon two or three atoms from the point of attachment of $Q^s$ to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkoxyamino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$), with the proviso that $R^{16}$, $R^{19}$, and $Q^b$ are not simultaneously hydrido;

$Q^b$ is selected from the group consisting of $NR^{20}R^{21}$, hydrido, $N(R^{26})C(NR^{25})N(R^{23})(R^{24})$, and $C(NR^{25})NR^{23}R^{24}$, with the proviso that no more than one of $R^{20}$ and $R^{21}$ is selected from the group consisting of hydroxy, amino, alkylamino, and dialkylamino at the same time, with the further proviso that no more than one of $R^{23}$ and $R^{24}$ is selected from the group consisting of hydroxy, amino, alkylamino, and dialkylamino at the same time;

$R^{20}$, $R^{21}$, $R^{23}$, $R^{24}$, $R^{25}$, and $R^{26}$ are independently selected from the group consisting of hydrido, alkyl, hydroxy, amino, alkylamino and dialkylamino;

$Q^s$ is selected from the group consisting of a bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, $S(O)$, $S(O)_2$, $S(O)_2N(R^{14})$, $N(R^{14})S(O)_2$, and $N(R^{14})$, with the proviso that $R^{14}$ is selected from other than halo when directly bonded to N, and with the additional proviso that $(CR^{37}R^{38})_b$, and $(CR^{37}R^{38})_b$, and $(CH(R^{14}))_c$ are bonded to $E^0$;

$R^{37}$ and $R^{38}$ are independently selected from the group consisting of hydrido, alkyl, and haloalkyl;

$R^{38}$ is optionally aroyl or heteroaroyl, wherein $R^{38}$ is optionally substituted with one or more substituents selected from the group consisting of $R^{16}$, $R^{17}$, $R^{18}$, and $R^{19}$;

$Y^0$ is optionally $Y^{AT}$ wherein $Y^{AT}$ is $Q^b$—$Q^s$;

$Y^0$ is optionally $Q^b$—$Q^{ss}$ wherein $Q^{ss}$ is $(CH(R^4))_e$—$W^2$—$(CH(R^{15}))_h$, wherein e and h are independently 1 or 2 and $W^2$ is $CR^{4a}$=$CR^{4b}$ with the proviso that $(CH(R^{14}))_e$ is bonded to $E^0$ In an even more preferred embodiment of a compound of Formula I, said compound is the Formula:

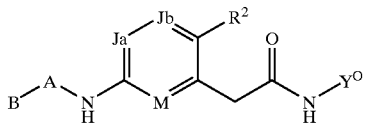

or a pharmaceutically acceptable salt thereof, wherein;

M is N or N→O;

B is phenyl or a heteroaryl of 5 or 6 ring members, wherein a carbon adjacent to the carbon at the point of attachment of said phenyl or heteroaryl ring to A is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, cyano, and $Q^b$;

A is a bond or $(CH(R^{15}))_{pa}$—$(W^7)$ rr wherein rr is 0 or 1, pa is an integer selected from 0 through 3, and $W^7$ is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

Ja is N or C—$X^0$;

Jb is N or C—$R^1$;

$R^1$ and $X^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is selected from the group consisting of a bond, $CH_2$, $CH_2CH_2W^0$—$(CH(R^{42}))_p$ wherein p is 0 or 1 and $W^1$ is selected from the group consisting of O, S, and $N(R^{41})$;

$R^{41}$ and $R^{42}$ are independently hydrido or alkyl;

Q is phenyl or a heteroaryl of 5 or 6 ring members, wherein a carbon adjacent to the carbon at the point of attachment of said phenyl or heteroaryl ring to $Z^0$ is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

$Y^0$ is phenyl or a heteroaryl of 5 or 6 ring members, wherein one carbon of said phenyl or said heteroaryl is substituted by $Q^s$, a carbon two or three atoms from the point of attachment of $Q^s$ to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^5)NR^{23}F^{24}$, with the proviso that no more than one of $R^{20}$ and $R^{21}$ is hydroxy at the same time and with the further proviso that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a bond, $CH_2$, and $CH_2CH_2$.

In another even more preferred embodiment of a compound of Formula I, said compound is the Formula:

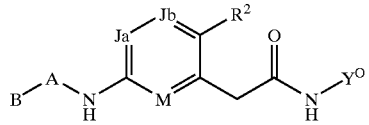

or a pharmaceutically acceptable salt thereof, wherein;

M is N or N→O;

B is selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$ $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, cyano, and $Q^b$;

A is a bond or $(CH(R^{15}))_{pa}$—$(W^7)_{rr}$ wherein rr is 0 or 1, pa is an integer selected from 0 through 3, and $W^7$ is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

Ja is N or C—$X^0$;

Jb is N or C—$R^1$;

$R^1$ and $X^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is selected from the group consisting of a bond, $CH_2$, $CH_2CH_2$, $W^0$—$(CH(R^{42}))_p$ wherein p is 0 or 1 and $W^0$ is selected from the group consisting of O, S, and $N(R^{41})$;

$R^{41}$ and $R^{42}$ are independently hydrido or alkyl;

Q is phenyl or a heteroaryl of 5 or 6 ring members, wherein a carbon adjacent to the carbon at the point of attachment of said phenyl or heteroaryl ring to $Z^0$ is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxamido, carboxamido, halo, haloalkyl, and cyano;

$Y^0$ is phenyl or a heteroaryl of 5 or 6 ring members, wherein one carbon of said phenyl or said heteroaryl is substituted by $Q^s$, a carbon two or three atoms from the point of attachment of $Q^s$ to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the proviso that no more than one of $R^{20}$ and $R^{21}$ is hydroxy at the same time and with the further proviso that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, alkyl, and hydroxy;

$Q^s$ is selected from the group consisting of a bond, $CH_2$, and $CH_2CH_2$.

In still another even more preferred embodiment of a compound of Formula I, said compound is the Formula:

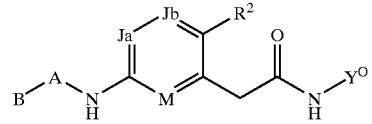

or a pharmaceutically acceptable salt thereof, wherein;

M is N or N→O;

B is a C3–C7 cycloalkyl or a C4–C6 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy,heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

$R^{33}$ and $R^{34}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, and cyano;

$R^{33}$ is optionally $Q^b$;

A is a bond or $(CH(R^{15}))_{pa}—(W^7)_{rr}$ wherein rr is 0 or 1, pa is an integer selected from 0 through 3, and $W^7$ is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

Ja is N or C—$X^0$;
Jb is N or C—$R^1$;

$R^1$ and $X^0$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is selected from the group consisting of a bond, $CH_2$, $CH_2CH_2$, $W^0$—$(CH(R^{42}))_p$ wherein p is 0 or 1 and $W^0$ is selected from the group consisting of O, S, and $N(R^{41})$;

$R^{41}$ and $R^{42}$ are independently hydrido or alkyl;

Q is phenyl or a heteroaryl of 5 or 6 ring members, wherein a carbon adjacent to the carbon at the point of attachment of said phenyl or heteroaryl ring to $Z^0$ is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{13}$ and $R^{12}$ is optionally substituted by $R^{11}$;

$Y^0$ is phenyl or a heteroaryl of 5 or 6 ring members, wherein one carbon of said phenyl or said heteroaryl is substituted by $Q^s$, a carbon two or three atoms from the point of attachment of $Q^s$ to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$, with the proviso that no more than one of $R^{20}$ and $R^{21}$ is hydroxy at the same time and with the further proviso that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a bond, $CH_2$, and $CH_2CH_2$.

In an additional even more preferred embodiment of a compound of Formula I, said compound is the Formula:

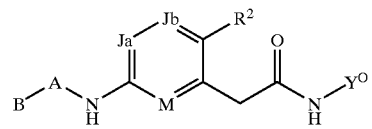

or a pharmaceutically acceptable salt thereof, wherein;

M is N or N→O;

B is selected from the group consisting of hydrido, trialkylsilyl, C2–C4 alkyl, C3–C5 alkylenyl, C3–C4 alkenyl, C3–C4 alkynyl, and C2–C4 haloalkyl, wherein each member of group B is optionally substituted at any carbon up to and including 3 atoms from the point of attachment of B to A with one or more of the group consisting of $R^{32}$, $R^{33}$, and $R^{34}$;

$R^{32}$, $R^{33}$, and $R^{34}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, and cyano;

A is $(CH(R^{15}))_{pa}—N(R^7)$ wherein pa is an integer selected from 0 through 2 and $R^7$ is hydrido or alkyl;

$R^{15}$ is selected from the group consisting of hydrido, halo, alkyl, and haloalkyl;

Ja is N or C—$X^0$;
Jb is N or C—$R^1$;

$R^1$ and $X^0$ are independently selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is a bond or $CH_2$;

Q is phenyl or a heteroaryl of 5 or 6 ring members, wherein a carbon adjacent to the carbon at the point of attachment of said phenyl or heteroaryl ring to $Z^0$ is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to R13 and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

$Y^0$ is phenyl or a heteroaryl of 5 or 6 ring members, wherein one carbon of said phenyl or said heteroaryl is substituted by $Q^s$, a carbon two or three atoms from the point of attachment of $Q^s$ to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the proviso that no more than one of $R^{20}$ and $R^{21}$ is hydroxy at the same time and with the further proviso that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, alkyl, and hydroxy;

$Q^s$ is selected from the group consisting of a bond, $CH_2$, and $CH_2CH_2$.

In a fifth even more preferred embodiment of a compound of Formula I, said compound is the Formula:

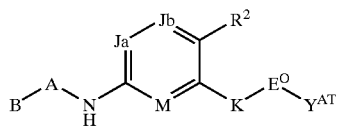

or a pharmaceutically acceptable salt thereof, wherein;

M is N or N→O;

B is phenyl or a heteroaryl of 5 or 6 ring members, wherein a carbon adjacent to the carbon at the point of attachment of said phenyl or heteroaryl ring to A is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, haloalkanoyl, nitro, alkylamino, alkylthio, aryl, aralkyl, cycloalkyl, cycloalkylalkyl, heteroaryl, heterocyclyl, alkylsulfonamido, amidosulfonyl, alkyl, alkenyl, halo, haloalkyl, haloalkenyl, haloalkoxy, hydroxyalkyl, alkylamino, carboalkoxy, carboxy, carboxamido, cyano, and $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C12 cycloalkyl or a C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^{12}$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^9$, $R^{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, cycloalkoxy, cycloalkylalkoxy, aralkoxy, aryloxy, heteroaryloxy, heteroaralkoxy,heterocyclyloxy, heterocyclylalkoxy, hydroxy, amino, alkylamino, N-alkyl-N-arylamino, arylamino, aralkylamino, heteroarylamino, heteroaralkylamino, heterocyclylamino, heterocyclylalkylamino, alkylthio, alkylsulfinyl, arylsulfinyl, aralkylsulfinyl, cycloalkylsulfinyl, heteroarylsulfinyl, alkylsulfamido, alkylsulfonyl, arylsulfonyl, aralkylsulfonyl, cycloalkylsulfonyl, heteroarylsulfonyl, amidosulfonyl, alkyl, aryl, aralkyl, cycloalkyl, cycloalkylalkyl, heteroaryl, heterocyclyl, halo, haloalkyl, haloalkoxy, hydroxyalkyl, hydroxyhaloalkyl, aminoalkyl, carboalkoxy, carboxy, carboxyalkyl, carboxamido, and cyano;

A is a bond or $(CH(R^{15}))_{pa}$—$(W^7)_{rr}$ wherein rr is 0 or 1, pa is an integer selected from 0 through 3, and $W^7$ is selected from the group consisting of O, S, C(O), $(R^7)NC(O)$, $(R^7)NC(S)$, and $N(R^7)$;

$R^7$ is selected from the group consisting of hydrido, hydroxy and alkyl;

$R^{15}$ is selected from the group consisting of hydrido, hydroxy, halo, alkyl, and haloalkyl;

Ja is N or C—$X^0$;

Jb is N or C—$R^1$;

$R^1$ and $X^0$ are independently selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

47

R² is Z⁰—Q;

Z⁰ is selected from the group consisting of a bond, $(CR^{41}R^{42})_q$ wherein q is 1 or 2, and $(CH(R^{41}))_g$—W⁰—$(CH(R^{42}))_p$ wherein g and p are integers independently selected from 0 through 3 and W⁰ is selected from the group consisting of O, S, C(O), S(O), N(R⁴¹), and ON(R⁴¹);

Z⁰ is optionally $(CH(R^{41}))_e$—W²²—$(CH(R^{42}))_h$ wherein e and h are independently 0 or 1 and W²² is selected from the group consisting of CR⁴¹=CR⁴², 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl,1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein Z⁰ is directly bonded to the pyridine ring and W²² is optionally substituted with one or more substituents selected from the group consisting of R⁹, R¹⁰, R¹¹, R12, and R¹³;

R⁴¹ and R⁴² are independently selected from the group consisting of hydrido, hydroxy, alkyl, and amino;

Q is phenyl or a heteroaryl of 5 or 6 ring members, wherein a carbon adjacent to the carbon at the point of attachment of said phenyl or heteroaryl ring to Z⁰ is optionally substituted by R⁹, the other carbon adjacent to the carbon at the point of attachment is optionally substituted by R¹³, a carbon adjacent to R⁹ and two atoms from the carbon at the point of attachment is optionally substituted by R¹⁰, a carbon adjacent to R¹³ and two atoms from the carbon at the point of attachment is optionally substituted by R¹², and any carbon adjacent to both R¹⁰ and R¹² is optionally substituted by R¹¹, with the proviso that Q is other than a phenyl when Z⁰ is a bond;

Q is optionally hydrido with the proviso that Z⁰ is selected from other than a bond;

K is CHR⁴ᵃ wherein R⁴ᵈ is selected from the group consisting of hydrido, hydroxyalkyl, alkyl, alkoxyalkyl, alkylthioalkyl, and haloalkyl;

E⁰ is selected from the group consisting of a bond, C(O)N(H), (H)NC(O), (R⁷)NS(O)₂, and S(O)₂N(R⁷);

Y^{AT} is $Q^b$—$Q^s$;

$Q^s$ is $(CR^{37}R^{38})_b$ wherein b is an integer selected from 1 through 4, R³⁷ is selected from the group consisting of hydrido, alkyl, and haloalkyl, and R³ is selected from the group consisting of hydrido, alkyl, haloalkyl, aroyl, and heteroaroyl with the proviso that there is at least one aroyl or heteroaroyl substituent, with the further proviso that no more than one aroyl or heteroaroyl is bonded to $(CR^{37}R^{38})_b$ at the same time, with the still further proviso that said aroyl and said heteroaroyl are optionally substituted with one or more substituents selected from the group consisting of R¹⁶, R¹⁷, R¹⁸, and R¹⁹, with another further proviso that said aroyl and said heteroaroyl are bonded to the CR³⁷R³⁸ that is directly bonded to E⁰, with still another further proviso that no more than one alkyl or one haloalkyl is bonded to a CR³⁷R³⁸ at the same time, and with the additional proviso that said alkyl and haloalkyl are bonded to a carbon other than the one bonding said aroyl or said heteroaroyl;

R¹⁶, R¹⁷, R¹⁸, and R¹⁹ are independently selected from the group consisting of hydrido, amidino, guanidino, carboxy, haloalkylthio, alkoxy, hydroxy, amino, alkoxyamino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

48

R¹⁶ or R¹⁹ is optionally selected from the group consisting of NR²⁰R²¹, N(R²⁶)C(NR²⁵)N(R²³)(R²⁴), and C(NR²⁵)NR²³R²⁴, with the proviso that R¹⁶, R¹⁹, and Q^b are not simultaneously hydrido;

Q^b is selected from the group consisting of NR²⁰R²¹, hydrido, N(R²⁶)C(NR²⁵)N(R²³)(R²⁴), and C(NR²⁵)NR²³R²⁴, with the proviso that no more than one of R²⁰ and R²¹ is selected from the group consisting of hydroxy, amino, alkylamino, and dialkylamino at the same time and with the further proviso that no more than one of R²³ and R²⁴ is selected from the group consisting of hydroxy, amino, alkylamino, and dialkylamino at the same time;

R²⁰, R²¹, R²³, R²⁴, R²⁵, and R²⁶ are independently selected from the group consisting of hydrido, alkyl, hydroxy, amino, alkylamino and dialkylamino.

In a most preferred embodiment of compounds of Formula I, said compound is the formula:

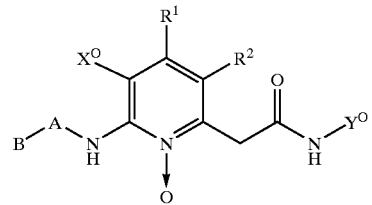

or a pharmaceutically acceptable salt thereof, wherein;

B is phenyl or a heteroaryl of 5 or 6 ring members, wherein a carbon adjacent to the carbon at the point of attachment of said phenyl or heteroaryl ring to A is optionally substituted by R³², the other carbon adjacent to the carbon at the point of attachment is optionally substituted by R³⁶, a carbon adjacent to R³² and two atoms from the carbon at the point of attachment is optionally substituted by R³³, a carbon adjacent to R³⁶ and two atoms from the carbon at the point of attachment is optionally substituted by R³⁵, and any carbon adjacent to both R³³ and R³⁵ is optionally substituted by R³⁴;

R³², R³³, R³⁴, R³⁵, and R³⁶ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, cyano, and Q^b;

A is a bond or $(CH(R^{15}))_{pa}$—$(W^7)_{rr}$ wherein rr is 0 or 1, pa is an integer selected from 0 through 3, and W⁷ is N(R⁷);

R⁷ is hydrido or alkyl;

R¹⁵ is selected from the group consisting of hydrido, halo, alkyl, and haloalkyl;

R¹ and X° are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

R² is Z⁰—Q;

Z⁰ is a bond;

Q is phenyl or a heteroaryl of 5 or 6 ring members, wherein a carbon adjacent to the carbon at the point of attachment of said phenyl or heteroaryl ring to Z⁰ is optionally substituted by R⁹, the other carbon adjacent to the carbon at the point of attachment is optionally substituted by R¹³, a carbon adjacent to R⁹ and two atoms from the carbon at the point of attachment is optionally substituted by R¹⁰, a carbon adjacent to R¹³ and two atoms from the carbon at the point of attachment is optionally substituted by R¹², and any carbon adjacent to both R¹⁰ and R¹² is optionally substituted by R¹¹;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

$Y^o$ is phenyl or a heteroaryl of 5 or 6 ring members, wherein one carbon of said phenyl or said heteroaryl is substituted by $Q^s$, a carbon two or three atoms from the point of attachment of $Q^s$ to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$;

$R^{20}$, $R^{21}$, $R^{23}$, $R^{24}$, and $R^{25}$ are independently hydrido or alkyl;

$Q^s$ is $CH_2$.

In a further most preferred embodiment of compounds of Formula I, said compound is the formula:

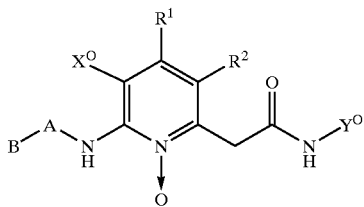

or a pharmaceutically acceptable salt thereof, wherein;

B is selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$ and $R^{36}$ $R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, cyano, and $Q^b$;

A is a bond or $(CH(R^{15}))_{pa}$—$(W^7)_{rr}$ wherein rr is 0 or 1, pa is an integer selected from 0 through 3, and $W^7$ is $N(R^7)$;

$R^7$ is hydrido or alkyl;

$R^{15}$ is selected from the group consisting of hydrido, halo, alkyl, and haloalkyl;

$R^1$ and $X^o$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^o$—Q;

$Z^o$ is a bond;

Q is phenyl or a heteroaryl of 5 or 6 ring members, wherein a carbon adjacent to the carbon at the point of attachment of said phenyl or heteroaryl ring to $Z^o$ is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

$Y^o$ is phenyl or a heteroaryl of 5 or 6 ring members, wherein one carbon of said phenyl or said heteroaryl is substituted by $Q^s$, a carbon two or three atoms from the point of attachment of $Q^s$ to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $N(R^{26})C(NR^{25})N(R^{23})(R^{24})$, and $C(NR^{25})NR^{23}R^{24}$;

$R^{20}$, $R^{21}$, $R^{23}$, $R^{24}$, $R^{25}$, and $R^{26}$ are independently hydrido or alkyl;

$Q^s$ is $CH_2$.

In a still further most preferred embodiment of compounds of Formula I, said compound is the formula:

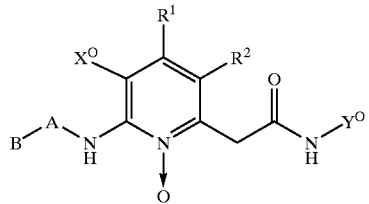

or a pharmaceutically acceptable salt thereof, wherein;

B is a C3–C7 cycloalkyl or a C4–C6 saturated heterocyclyl, wherein each ring carbon is optionally Substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$, and $R^{33}$ positions is optionally substituted with $R^{34}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

$R^{33}$ and $R^{34}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, and cyano;

$R^{33}$ is optionally $Q^b$;

A is a bond or $(CH(R^{15}))_{pa}—(W^7)_{rr}$ wherein rr is 0 or 1, pa is an integer selected from 0 through 3, and $W^7$ is $N(R^7)$;

$R^7$ is hydrido or alkyl;

$R^{15}$ is selected from the group consisting of hydrido, halo, alkyl, and haloalkyl;

$R^1$ and $X^o$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^o$—Q;

$Z^o$ is a bond;

Q is phenyl or a heteroaryl of 5 or 6 ring members, wherein a carbon adjacent to the carbon at the point of attachment of said phenyl or heteroaryl ring to $Z^0$ is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$Y^o$ is phenyl or a heteroaryl of 5 or 6 ring members, wherein one carbon of said phenyl or said heteroaryl is substituted by $Q^s$, a carbon two or three atoms from the point of attachment of $Q^s$ to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$;

$R^{20}$, $R^{21}$, $R^{23}$, $R^{24}$, and $R^{25}$ are independently hydrido or alkyl;

$Q^s$ is $CH_2$.

In a preferred specific embodiment of Formula I, compounds have the formula:

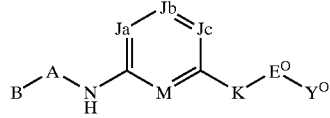

or a pharmaceutically acceptable salt thereof, wherein;

M is N or N→O;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, 1,2,3-triazin-4-yl, and 1,2,3-triazin-5-yl, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, carboxy, methyl, ethyl, isopropyl, propyl, methoxy, ethoxy, isopropoxy, propoxy, hydroxy, amino, methoxyamino, ethoxyamino, acetamido, trifluoroacetamido, nitro, aminomethyl, 1-aminoethyl, 2-aminoethyl, N-methylamino, dimethylamino, N-ethylamino, methylthio, ethylthio, isopropylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, cyano, and $Q^b$;

B is selected from the group consisting of hydrido, trimethylsilyl, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 1-octyl, 2-octenyl, 3-octenyl, 4-octenyl, 5-octenyl, 6-octenyl, 7-octenyl, 2-octynyl, 3-octynyl, 4-octynyl, 5-octynyl,6-octynyl, 2-octyl, 1-methyl-2-heptenyl, 1-methyl-3-heptenyl, 1-methyl-4-heptenyl, 1-methyl-5-heptenyl, 1-methyl-6-heptenyl, 1-methyl-2-heptynyl, 1-methyl-3-heptynyl, 1-methyl-4-heptenyl, 1-methyl-5-heptenyl, 1-methyl-6-heptenyl, 1-methyl-2-heptenyl, 1-methyl-3-heptynyl, 1-methyl-4-heptynyl, 1-methyl-5-heptynyl, 3-octyl, 1-ethyl-2-hexenyl, 1-ethyl-3-hexenyl, 1-ethyl-4-hexenyl, 1-ethyl-2-hexynyl, 1-ethyl-3-hexynyl, 1-ethyl-4-hexynyl, 1-ethyl-5-hexenyl, 1-pentyl-2-propenyl, 4-octyl, 1-propyl-2-pentenyl, 1-propyl-3-pentenyl, 1-propyl-4-pentenyl, 1-butyl-2-butenyl, 1-propyl-2-pentynyl, 1-propyl-3-pentynyl, 1-butyl-2-butynyl, 1-butyl-3-butenyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted :at any carbon up to and including 5 atoms from the point of attachment of B to A with one or more of the group consisting of $R^{32}$, $R^{33}$ $R^{34}$, $R^{35}$, and $R^{36}$;

B is optionally selected from the group consisting of cyclopropyl, cyclobutyl, oxetan-2-yl, oxetan-3-yl, azetidin-1-yl, azetidin-2-yl, azetidin-3-yl, thiaetan-2-yl, thiaetan-3-yl, cyclopentyl, cyclohexyl, adamantyl, norbornyl, 3-trifluoromethylnorbornyl, 7-oxabicyclo[2.2.1]heptan-2-yl, bicyclo[3.1.0]hexan-6-yl, cycloheptyl, cyclooctyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 4H-2-pyranyl, 4H-3-pyranyl, 4H-4-pyranyl, 4H-pyran-4-one-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, a ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, and a ring carbon or nitrogen atom adjacent to the $R^{13}$ position and two atoms from the point of attachment is optionally substituted with $R^{12}$;

$R^9$, $R^{10}$, $R^{11}$, $R^{12}$, and $R^{13}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl)amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, fluoro, chloro, bromo, cyano, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy;

A is selected from the group consisting of a bond, O, S, NH, N(CH$_3$), N(OH), C(O), CH$_2$, CH$_3$CH, CF$_3$CH, NHC(O), N(CH$_3$)C(O), C(O)NH, C(O)N(CH$_3$), CF$_3$CC(O), C(O)CCH$_3$, C(O)CCF$_3$, CH$_2$C(O), (O)CCH$_2$, CH$_2$CH$_2$, CH$_2$CH$_2$CH$_2$, CH$_3$CHCH$_2$, CF$_3$CHCH$_2$, CH$_3$CC(O)CH$_2$, CF₃CC(O)CH₂, CH2C(O)CCH₃, CH₂C(O)CCF₃, CH₂CH₂C(O), and CH₂(O)CCH₂;

A is optionally selected from the group consisting of CH₂N(CH₃), CH₂N(CH₂CH₃), CH₂CH₂N(CH₃), and CH₂CH₂N(CH₂CH₃) with the proviso that B is hydrido;

Ja is independently selected from the group consisting of N and C—X°;

Jb is independently selected from the group consisting of N and C—R¹;

Jc is independently selected from the group consisting of N and C—R², with the proviso that at least one of Ja, Jb, and Jc are not a nitrogen (N).

R¹ and X° are independently selected from the group consisting of hydrido, hydroxy, amino, thiol, amidino, hydroxyamino, aminomethyl, 1-aminoethyl, 2-aminoethyl, methylamino, dimethylamino, cyano, methyl, ethyl, isopropyl, propyl, trifluoromethyl, pentafluoroethyl, 2,2,2-trifluoroethyl, 2,2,3,3,3-pentafluoropropyl, methoxy, ethoxy, propoxy, hydroxymethyl, 1-hydroxyethyl, 2-hydroxyethyl, methoxyamino, ethoxyamino, methylthio, ethylthio, trifluoromethoxy, 1,1,2,2-tetrafluoroethoxy, fluoro, chloro, and bromo;

R² is Z°—Q;

Z° is selected from the group consisting of a bond, CH₂, CH₂CH₂, O, S, NH, N(CH₃), CH(OH), OCH₂, SCH₂, N(H)CH₂, CH₂O, CH₂S, CH₂N(H), CH(NH₂), CH₂CH(OH), CH₂CHNH₂, CH(OH)CH₂, and CH(NH₂)CH₂;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, 1,2,3-triazin-4-yl, and 1,2,3-triazin-5-yl, wherein a carbon adjacent to the carbon at the point of attachment is optionally substituted by R⁹, the other carbon adjacent to the carbon at the point of attachment is optionally substituted by R¹³, a carbon adjacent to R⁹ and two atoms from the carbon at the point of attachment is optionally substituted by R¹⁰, a carbon adjacent to R¹³ and two atoms from the carbon at the point of attachment is optionally substituted by R¹², and any carbon adjacent to both R¹⁰ and R¹² is optionally substituted by R¹¹;

K is CR⁴ᵃR⁴ᵇ wherein R⁴ᵃ and R⁴ᵇ are independently selected from the group consisting of methyl, ethyl, propyl, isopropyl, fluoro, chloro, hydroxy, hydroxymethyl, 1-hydroxyethyl, methoxymethyl, trifluoromethyl, pentafluoroethyl, 2,2,2-trifluoromethyl, methylthiomethyl, and hydrido;

E° is a bond, C(O)N(H), (H)NC(O), and S(O)₂N(H);

Y° is selected from the group of formulas consisting of:

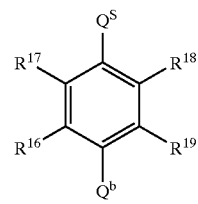

1-Qᵇ-4-Qˢ-2-R¹⁶-3-R¹⁷-5-R¹⁸-6-R¹⁹benzene

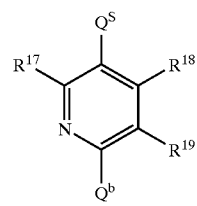

2-Qᵇ-5-Qˢ-6-R¹⁷-4-R¹⁸-3-R¹⁹pyridine,

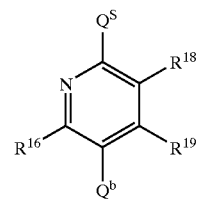

3-Qᵇ-6-Qˢ-2-R¹⁶-5-R¹⁸-4-R¹⁹pyridine,

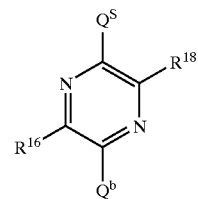

2-Qᵇ-5-Qˢ-3-R¹⁶-6-R¹⁸pyrazine,

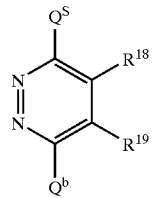

3-Qᵇ-6-Qˢ-2-R¹⁸-5-R¹⁸-4-R¹⁹pyridazine,

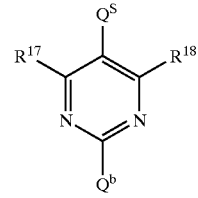

2-Qᵇ-5-Qˢ-4-R¹⁷-6-R¹⁸pyrimidine,

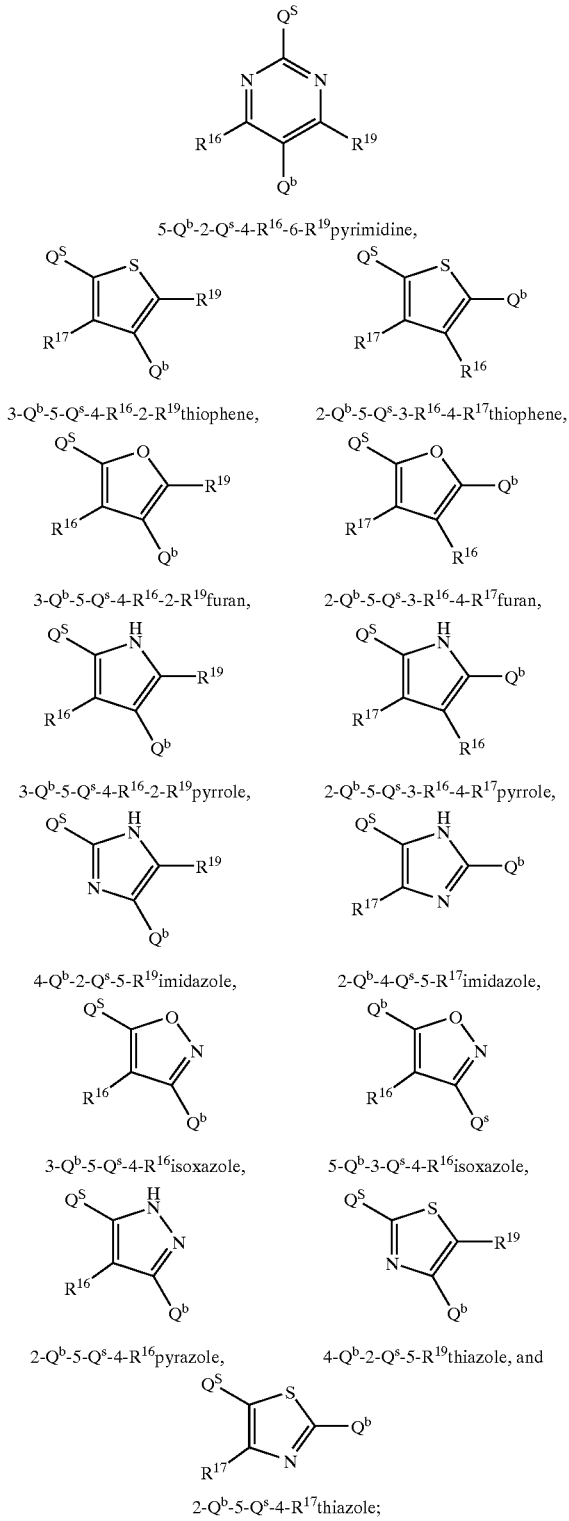

5-Q^b-2-Q^s-4-R^16-6-R^19pyrimidine,

3-Q^b-5-Q^s-4-R^16-2-R^19thiophene,    2-Q^b-5-Q^s-3-R^16-4-R^17thiophene,

3-Q^b-5-Q^s-4-R^16-2-R^19furan,    2-Q^b-5-Q^s-3-R^16-4-R^17furan,

3-Q^b-5-Q^s-4-R^16-2-R^19pyrrole,    2-Q^b-5-Q^s-3-R^16-4-R^17pyrrole,

4-Q^b-2-Q^s-5-R^19imidazole,    2-Q^b-4-Q^s-5-R^17imidazole,

3-Q^b-5-Q^s-4-R^16isoxazole,    5-Q^b-3-Q^s-4-R^16isoxazole,

2-Q^b-5-Q^s-4-R^16pyrazole,    4-Q^b-2-Q^s-5-R^19thiazole, and

2-Q^b-5-Q^s-4-R^17thiazole;

$R^{16}$, $R^{17}$, $R^{18}$, and $R^{19}$ are independently selected from the group consisting of hydrido, methyl, ethyl, isopropyl, propyl, amidino, guanidino, carboxy, methoxy, ethoxy, isopropoxy, propoxy, hydroxy, amino, methoxyamino, ethoxyamino, aminomethyl, 1-aminoethyl, 2-aminoethyl, N-N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, and cyano;

$Q^b$ is selected from the group consisting of $NR^{20}R^{21}$, hydrido, $C(NR^{25})NR^{23}R^{24}$ and $N(R^{26})C(NR^{25})N(R^{23})(R^{24})$, with the proviso that no more than one of $R^{20}$ and $R^{21}$ is hydroxy, N-methylamino, and N,N-dimethylamino at the same time and that no more than one of $R^{23}$ and $R^{24}$ is hydroxy, N-methylamino, and N,N-dimethylamino at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, hydroxy, 2-aminoethyl, 2-(N-methylamino)ethyl, and 2-(N,N-dimethylamino)ethyl;

$Q^s$ is selected from the group consisting of a bond, $CH_2$, $CH_2CH_2$, $CH_3CH$, $CF_3CH$, $CH_3CHCH_2$, $CF_3CHCH_2$, $CH_2(CH_3)CH$, $CH=CH$, $CF=CH$, $C(CH_3)=CH$, $CH=CHCH_2$, $CF=CHCH_2$, $C(CH_3)=CHCH_2$, $CH_2CH=CH$, $CH_2CF=CH$, $CH_2C(CH_3)=CH$, $CH_2CH=CHCH_2$, $CH_2CF=CHCH_2$, $CH_2C(CH_3)=CHCH_2$, $CH2CH=CHCH_2CH_2$, $CH_2CF=CHCH_2CH_2$, and $CH_2C(CH_3)=CHCH_2CH_2$.

In a more preferred specific embodiment of Formula I, compounds have the formula:

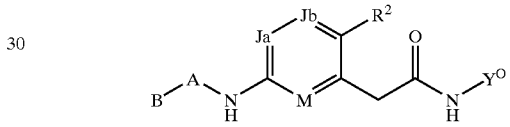

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment of said phenyl or heteroaryl ring to A is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of a bond, NH, $N(CH_3)$, $N(OH)$, $CH_2$, $CH_3CH$, $CF_3CH$, NHC(O), $N(CH_3)$ C(O), C(O)NH, C(O)N(CH₃), CH₂CH₂, CH₂CH₂CH₂, CH₃CHCH₂, and CF₃CHCH₂;

$R^{16}$, $R^{17}$, $R^{18}$, and $R^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano;

$R^{16}$ or $R^{19}$ is optionally C(NR²⁵)NR²³R²⁴ with the proviso that $R^{16}$, $R^{19}$, and $Q^b$ are not simultaneously hydrido;

$Q^b$ is C(NR²⁵)NR²³R²⁴ or hydrido, with the proviso that no more than one of $R^{23}$ and $R^{24}$ is hydroxy at the same time;

$R^{23}$, $R^{24}$, and $R^{25}$ are independently selected from the group consisting of hydrido, methyl, ethyl, and hydroxy.

In another more preferred specific embodiment of Formula I, compounds have the formula:

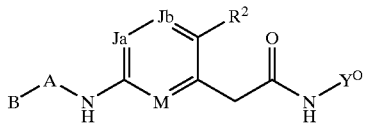

or a pharmaceutically acceptable salt thereof, wherein;

B is selected from the group consisting of hydrido, ethyl, 2-propynyl, 2-propenyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$ $R^{34}$ $R^{35}$ and $R^{36}$;

$R^{32}$, $R^{33}$, $R^{34}$, $R^{35}$ and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of bond, NH, N(CH₃), N(OH), CH₂, CH₃CH, CF₃CH, NHC(O), N(CH₃)C(O), C(O)NH, C(O)N(CH₃), CH₂CH₂, CH₂CH₂CH₂, CH₃CHCH₂, and CF₃CHCH₂;

$R^{16}$, $R^{17}$, $R^{18}$, and $R^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano;

$R^{16}$ or $R^{19}$ is optionally selected from the group consisting of NR²⁰R²¹, C(NR²⁵)NR²³R²⁴, and N(R²⁶)C(NR²⁵)N(R²³)(R²⁴), with the proviso that $R^{16}$, $R^{19}$, and $Q^b$ are not simultaneously hydrido;

$Q^b$ is selected from the group consisting of NR²⁰R²¹, hydrido, C(NR²⁵)NR²³R²⁴, and N(R²⁶)C(NR²⁵)N(R²³)(R²⁴), with the proviso that no more than one of $R^{20}$ and $R^{21}$ is hydroxy at the same time and with the further proviso that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, and hydroxy.

In still another more preferred specific embodiment of Formula I, compounds have the formula:

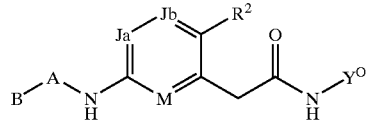

or a pharmaceutically acceptable salt thereof, wherein;

B is selected from the group consisting of cyclopropyl, cyclobutyl, oxetan-3-yl, azetidin-1-yl, azetidin-2-yl, azetidin-3-yl, thiaetan-3-yl, cyclopentyl, cyclohexyl, norbornyl, 7-oxabicyclo[2.2.1]heptan-2-yl, bicyclo[3.1.0]hexan-6-yl, cycloheptyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 4H-2-pyranyl, 4H-3-pyranyl, 4H-4-pyranyl, 4H-pyran-4-one-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, and a ring carbon or nitrogen adjacent to the $R^{13}$ position and two atoms from the point of attachment is optionally substituted with $R^{12}$;

$R^{33}$ is selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of a bond, NH, $N(CH_3)$, $N(OH)$, $CH_2$, $CH_3CH$, $CF_3CH$, $NHC(O)$, $N(CH_3)C(O)$, $C(O)NH$, $C(O)N(CH_3)$, $CH_2CH_2$, $CH_2CH_2CH_2$, $CH_3CHCH_2$, and $CF_3CHCH_2$;

$R^{16}$, $R^{17}$, $R^{18}$, and $R^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano;

$R^{16}$ or $R^{19}$ is optionally $C(NR^{25})NR^{23}R^{24}$ with the proviso that $R^{16}$, $R^{19}$, and $Q^b$ are not simultaneously hydrido;

$Q^b$ is $C(NR^{25})NR^{23}R^{24}$ or hydrido, with the proviso that no more than one of $R^{23}$ and $R^{24}$ is hydroxy at the same time;

$R^{23}$, $R^{24}$, and $R^{25}$ are independently selected from the group consisting of hydrido, methyl, ethyl, and hydroxy.

The more preferred specific embodiment compounds of Formula I having the formula:

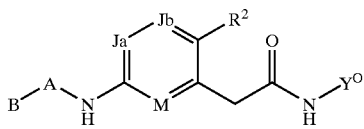

or a pharmaceutically acceptable salt thereof, have common structural units, wherein;

M is N or N→O;

Ja is N or C—$X^o$;

Jb is N or C—$R^1$;

$R^1$ and $X^o$ are independently selected from the group consisting of hydrido, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;

$R^2$ is $Z^o$—Q;

$Z^o$ is selected from the group consisting of a bond, $CH_2$, $CH_2CH_2$, O, S, NH, $N(CH_3)$, $OCH_2$, $SCH_2$, $N(H)CH_2$, and $N(CH_3)CH_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment of said phenyl or heteroaryl ring to $Z^o$ is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{13}$ is optionally substituted by $R^{11}$;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl)amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, fluoro, chloro, bromo, cyano, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2- trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy;

$Y^o$ is selected from the group of formulas consisting of:

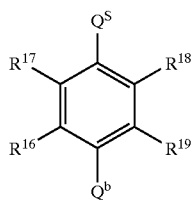

1-$Q^b$-4-$Q^s$-2-$R^{16}$-3-$R^{17}$-5-$R^{18}$-6-$R^{19}$benzene

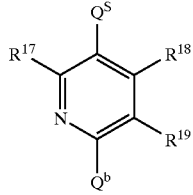

2-$Q^b$-5-$Q^s$-6-$R^{17}$-4-$R^{18}$-3-$R^{19}$pyridine,

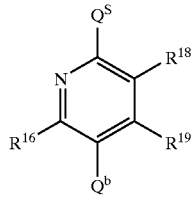

3-$Q^b$-6-$Q^s$-2-$R^{16}$-5-$R^{18}$-4-$R^{19}$pyridine,

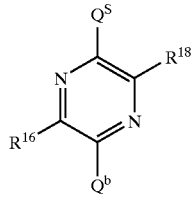

2-$Q^b$-5-$Q^s$-3-$R^{16}$-6-$R^{18}$pyrazine,

-continued

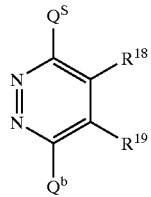

3-$Q^b$-6-$Q^s$-2-$R^{18}$-5-$R^{18}$-4-$R^{19}$pyridazine,

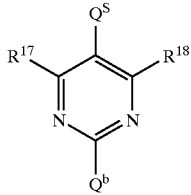

2-$Q^b$-5-$Q^s$-4-$R^{17}$-6-$R^{18}$pyrimidine,

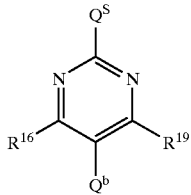

5-$Q^b$-2-$Q^s$-4-$R^{16}$-6-$R^{19}$pyrimidine,

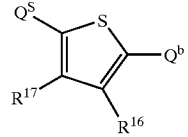

3-$Q^b$-5-$Q^s$-4-$R^{16}$-2-$R^{19}$thiophene,    2-$Q^b$-5-$Q^s$-3-$R^{16}$-4-$R^{17}$thiophene,

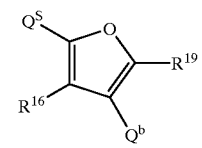 

3-$Q^b$-5-$Q^s$-4-$R^{16}$-2-$R^{19}$furan,    2-$Q^b$-5-$Q^s$-3-$R^{16}$-4-$R^{17}$furan,

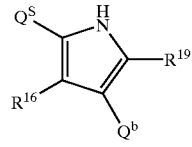 

3-$Q^b$-5-$Q^s$-4-$R^{16}$-2-$R^{19}$pyrrole,    2-$Q^b$-5-$Q^s$-3-$R^{16}$-4-$R^{17}$pyrrole,

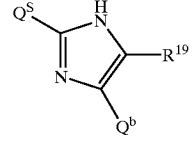 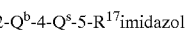

4-$Q^b$-2-$Q^s$-5-$R^{19}$imidazole,    2-$Q^b$-4-$Q^s$-5-$R^{17}$imidazole,

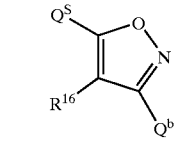 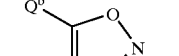

3-$Q^b$-5-$Q^s$-4-$R^{16}$isoxazole,    5-$Q^b$-3-$Q^s$-4-$R^{16}$isoxazole,

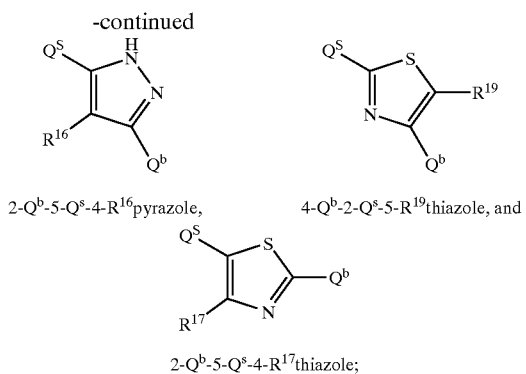

2-$Q^b$-5-$Q^s$-4-$R^{16}$pyrazole,   4-$Q^b$-2-$Q^s$-5-$R^{19}$thiazole, and

2-$Q^b$-5-$Q^s$-4-$R^{17}$thiazole;

$Q^s$ is selected from the group consisting of a bond, $CH_2$ and $CH_2CH_2$.

In a most preferred specific embodiment of Formula I, compounds have the formula:

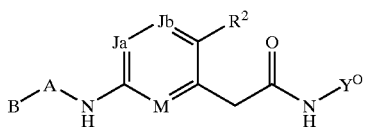

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, and 5-isoxazolyl,carbon at the point of attachment of said phenyl or heteroaryl ring to A is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of a bond, NH, N($CH_3$), $CH_2$, $CH_3CH$, and $CH_2CH_2$;

$Q^b$ is $NR^{20}R^{21}$ or C($NR^{25}$)$NR^{23}R^{24}$;

$R^{20}$, $R^{21}$, $R^{23}$, $R^{24}$, and $R^{25}$ are independently selected from the group consisting of hydrido, methyl, and ethyl.

In another most preferred specific embodiment of Formula I, compounds have the formula:

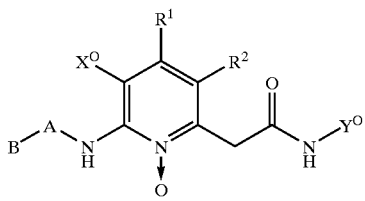

or a pharmaceutically acceptable salt thereof, wherein;

B is selected from the group consisting of hydrido, ethyl, 2-propenyl, 2-propynyl, propyl, isopropyl, butyl, 2-butenyl, 2-butynyl, sec-butyl, tert-butyl, isobutyl, 2-methylpropenyl, 1-pentyl, 2-pentenyl, 3-pentenyl, 2-pentynyl, 3-pentynyl, 2-pentyl, 3-pentyl, 2-methylbutyl, 2-methyl-2-butenyl, 3-methylbutyl, 3-methyl-2-butenyl, 1-hexyl, 2-hexenyl, 3-hexenyl, 4-hexenyl, 2-hexynyl, 3-hexynyl, 4-hexynyl, 2-hexyl, 1-methyl-2-pentenyl, 1-methyl-3-pentenyl, 1-methyl-2-pentynyl, 1-methyl-3-pentynyl, 3-hexyl, 1-ethyl-2-butenyl, 1-heptyl, 2-heptenyl, 3-heptenyl, 4-heptenyl, 5-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$ $R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl carboxy, cyano, and $Q^b$;

A is selected from the group consisting of a bond, NH, N($CH_3$), $CH_2$, $CH_3CH$, and $CH_2CH_2$;

A is optionally selected from the group consisting of $CH_2N(CH_3)$, $CH_2N(CH_2CH_3)$, $CH_2CH_2N(CH_3)$, and $CH_2CH_2N(CH_2CH_3)$ with the proviso that B is hydrido;

$Q^b$ is selected from the group consisting of $NR^{20}R^{21}$, C($NR^{25}$)$NR^{23}R^{24}$, and N($R^{26}$)C($NR^{25}$)N($R^{23}$)($R^{24}$), $R^{20}$, $R^{21}$ $R^{23}$, $R^{24}$, $R^{25}$, and $R^{26}$ are independently selected from the group consisting of hydrido, methyl, and ethyl.

In still another most preferred specific embodiment of Formula I, compounds have the formula:

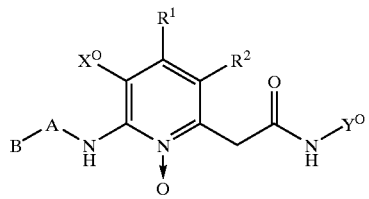

or a pharmaceutically acceptable salt thereof, wherein;

B is selected from the group consisting of cyclopropyl, cyclobutyl, cyclopentyl, cyclohexyl, cycloheptyl, oxalan-2-yl, 2-(2R)-bicyclo[2.2.1]-heptyl, oxetan-3-yl, azetidin-1-yl, azetidin-2-yl, azetidin-3-yl, bicyclo[3.1.0]hexan-6-yl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment are optionally substituted with $R^{10}$, and a ring carbon or nitrogen atom adjacent to the $R^{13}$ position and two atoms from the point of attachment is optionally substituted with $R^{12}$;

$R^{33}$ is selected from the group consisting of hydrido, amidino, guanidino, methyl, ethyl, methoxy, ethoxy, hydroxy, carboxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, cyano, and $Q^b$;

A is selected from the group consisting of a bond, NH, $N(CH_3)$, $CH_2$, $CH_3CH$, $CH_2CH_2$, and $CH_2CH_2CH_2$;

$Q^b$ is $NR^{20}R^{21}$ or $C(NR^{25})NR^{23}R^{24}$;

$R^{20}$, $R^{21}$, $R^{23}$, $R^{24}$, and $R^{25}$ are independently selected from the group consisting of hydrido, methyl, and ethyl.

The most preferred specific embodiment compounds of Formula I said compounds having the formula:

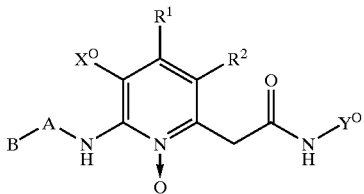

or a pharmaceutically acceptable salt thereof, have common structural units, wherein;

$X^o$ is selected from the group consisting of hydrido, hydroxy, amino, amidino, aminomethyl, cyano, methyl, trifluoromethyl, hydroxymethyl, chloro, and fluoro;

$R^1$ is selected from the group consisting of hydrido, hydroxy, hydroxymethyl, amino, aminomethyl, methylamino, cyano, methyl, trifluoromethyl, methoxy, methylthio, trifluoromethoxy, fluoro, and chloro;

$R^2$ is selected from the group consisting of phenyl, 2-thienyl, 2-furyl, 2-pyrrolyl, 2-imidazolyl, 2-thiazolyl, 3-isoxazolyl, 2-pyridyl, and 3-pyridyl, wherein a carbon adjacent to the carbon at the point of attachment of said phenyl or heteroaryl ring to the pyridine ring is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrido, amidino, amidocarbonyl, N-methylamidocarbonyl, N-benzylamidocarbonyl, N-(2-chlorobenzyl)amidocarbonyl, N-(3-fluorobenzyl)amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, methoxyamino, amidosulfonyl, N-methylamidosulfonyl, N,N-dimethylamidosulfonyl, methanesulfonamido, methoxycarbonyl, fluoro, chloro, bromo, and cyano;

$Y^o$ is selected from the group of formulas consisting of:

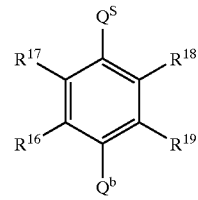

1-$Q^b$-4-$Q^s$-2-$R^{16}$-3-$R^{17}$-5-$R^{18}$-6-$R^{19}$benzene

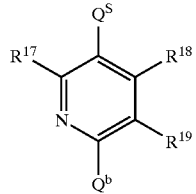

2-$Q^b$-5-$Q^s$-6-$R^{17}$-4-$R^{18}$-3-$R^{19}$pyridine,

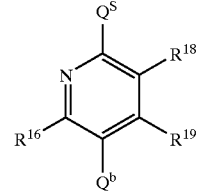

3-$Q^b$-6-$Q^s$-2-$R^{16}$-5-$R^{18}$-4-$R^{19}$pyridine,

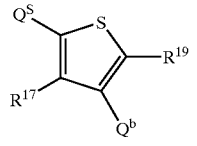

3-$Q^b$-5-$Q^s$-4-$R^{16}$-2-$R^{19}$thiophene,  2-$Q^b$-5-$Q^s$-3-$R^{16}$-4-$R^{17}$thiophene,

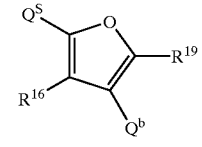

3-$Q^b$-5-$Q^s$-4-$R^{16}$-2-$R^{19}$furan,  2-$Q^b$-5-$Q^s$-3-$R^{16}$-4-$R^{17}$furan,

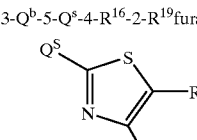

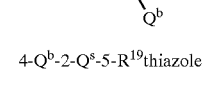

4-$Q^b$-2-$Q^s$-5-$R^{19}$thiazole, and  2-$Q^b$-5-$Q^s$-4-$R^{17}$thiazole;

$R^{16}$, $R^{17}$, $R^{18}$, and $R^{19}$ are independently selected from the group consisting of hydrido, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, hydroxymethyl, carboxy, and cyano;

$Q^s$ is $CH_2$.

The compounds of this invention can be used in anticoagulant therapy for the treatment and prevention of a variety of thrombotic conditions including coronary artery and cerebrovascular disease. The compounds of this invention can be used to inhibit serine protease associated with the coagulation cascade and factors II, VII, VIII, IX, X, XI, or XII. The compounds of the invention can inhibit the formation of blood platelet aggregates, inhibit the formation of fibrin, inhibit thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The compounds can also be used in prophylactic treatment of subjects who are at risk of developing such disorders. The compounds can be used to lower the risk of atherosclerosis. The compounds of Formula (I) would also be useful in prevention of cerebral vascular accident (CVA) or stroke.

Besides being useful for human treatment, these compounds are also useful for veterinary treatment of companion animals, exotic animals and farm animals, including mammals, rodents, and the like. More preferred animals include horses, dogs, and cats.

In yet another embodiment of the present invention, the novel compounds are selected from the compounds set forth in Examples 1 through 14.

The use of generic terms in the description of the compounds are herein defined for clarity.

The generic terms described below are applicable solely for compounds based upon Formula I. Therefore, these generic terms, unless otherwise indicated or generally known in the art, should not be utilized to construe the meaning of compounds based upon Formula A.

Standard single letter elemental symbols are used to represent specific types of atoms unless otherwise defined. The symbol "C" represents a carbon atom. The symbol "O" represents an oxygen atom. The symbol "N" represents a nitrogen atom. The symbol "P" represents a phosphorus atom. The symbol "S" represents a sulfur atom. The symbol "H" represents a hydrido atom. Double letter elemental symbols are used as defined for the elements of the periodical table (i.e., Cl represents chlorine, Se represents selenium, etc.).

As utilized herein, the term "alkyl", either alone or within other terms such as "haloalkyl", and "alkylthio", means an acyclic alkyl radical containing from 1 to about 10, preferably from 3 to about 8 carbon atoms and more preferably 3 to about 6 carbon atoms. Said alkyl radicals may be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical in so much as it contains at least one double bond. Such alkenyl radicals contain from about 2 to about 10 carbon atoms, preferably from about 3 to about 8 carbon atoms and more preferably 3 to about 6 carbon atoms. Said alkenyl radicals may be optionally substituted with groups as defined below. Examples of suitable alkenyl radicals include propenyl, 2-chloropropenyl, buten-1-yl, isobutenyl, penten-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, preferably having from about 3 to about 8 carbon atoms and more preferably having 3 to about 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "hydrido" denotes a single hydrogen atom (H). This hydrido radical may be attached, for example, to an oxygen atom to form a "hydroxyl" radical, one hydrido radical may be attached to a carbon atom to form a "methine" radical —CH=, or two hydrido radicals may be attached to a carbon atom to form a "methylene" (—CH$_2$—) radical.

The term "carbon" radical denotes a carbon atom without any covalent bonds and capable of forming four covalent bonds.

The term "cyano" radical denotes a carbon radical having three of four covalent bonds shared by a nitrogen atom.

The term "hydroxyalkyl" embraces radicals wherein any one or more of the alkyl carbon atoms is substituted with a hydroxyl as defined above. Specifically embraced are monohydroxyalkyl, dihydroxyalkyl and polyhydroxyalkyl radicals.

The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl.

The term "alkylene" radical denotes linear or branched radicals having from 1 to about 10 carbon atoms and having attachment points for two or more covalent bonds. Examples of such radicals are methylene, ethylene, methylethylene, and isopropylidene.

The term "alkenylene" radical denotes linear or branched radicals having from 2 to about 10 carbon atoms, at least one double bond, and having attachment points for two or more covalent bonds. Examples of such radicals are 1,1-vinylidene (CH$_2$=C), 1,2-vinylidene (—CH=CH—), and 1,4-butadienyl (—CH=CH—CH=CH—).

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "haloalkyl" radicals having one to about six carbon atoms. Examples of such haloalkyl radicals include fluoromethyl, difluoromethyl, trifluoromethyl, chloromethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl and dichloropropyl.

The term "hydroxyhaloalkyl" embraces radicals wherein any one or more of the haloalkyl carbon atoms is substituted with hydroxy as defined above. Examples of "hydroxyhaloalkyl" radicals include hexafluorohydroxypropyl.

The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred haloalkylene radicals are "haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The terms "alkoxyl" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "alkoxy" radicals having one to six carbon atoms. Examples of such radicals include methoxy, ethoxy, propoxy, butoxy, isopropoxy and tert-butoxy alkyls. The "alkoxyl" radicals may be further substituted with one or more halo atoms, such as fluoro, chloro or bromo, to provide "haloalkoxyl" and "haloalkoxyalkyl" radicals. Examples of such haloalkoxy radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy. Examples of such haloalkoxyalkyl radicals include fluoromethoxymethyl, chloromethoxyethyl, trifluoromethoxymethyl, difluoromethoxyethyl, and trifluoroethoxymethyl.

The terms "alkenyloxy" and "alkenyloxyalkyl" embrace linear or branched oxy-containing radicals each having alkenyl portions of two to about ten carbon atoms, such as ethenyloxy or propenyloxy radical. The term "alkenyloxyalkyl" also embraces alkenyl radicals having one or more alkenyloxy radicals attached to the alkyl radical, that is, to form monoalkenyloxyalkyl and dialkenyloxyalkyl radicals. More preferred alkenyloxy radicals are "alkenyloxy" radicals having two to six carbon atoms. Examples of such radicals include ethenyloxy, propenyloxy, butenyloxy, and isopropenyloxy alkyls. The "alkenyloxy" radicals may be further substituted with one or more halo atoms, such as fluoro, chloro or bromo, to provide "haloalkenyloxy" radicals. Examples of such radicals include trifluoroethenyloxy, fluoroethenyloxy, difluoroethenyhloxy, and fluoropropenyloxy.

The term "haloalkoxyalkyl" also embraces alkyl radicals having one or more haloalkoxy radicals attached to the alkyl radical, that is, to form monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals.

The term "alkylenedioxy" radicals denotes alkylene radicals having at least two oxygens bonded to a single alkylene group. Examples of "alkylenedioxy" radicals include methylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoroethylenedioxy, tetrachloroethylenedioxy, alkylsubstituted monofluoromethylenedioxy, and arylsubstituted monofluoromethylenedioxy.

The term "aryl", alone or in combination, means a carbocyclic aromatic system containing one, two or three rings wherein such rings may be attached together in a pendant manner or may be fused. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indane and biphenyl.

The term "perhaloaryl" embraces aromatic radicals such as phenyl, naphthyl, tetrahydronaphthyl, indane and biphenyl wherein the aryl radical is substituted with 3 or more halo radicals as defined below.

The term "heterocyclyl" embraces saturated and partially saturated heteroatom-containing ring-shaped radicals having from 4 through 15 ring members, herein referred to as "C4–C15 heterocyclyl", selected from carbon, nitrogen, sulfur and oxygen, wherein at least one ring atom is a heteroatom. Heterocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclyl radicals include dihydrothiophene, dihydropyran, dihydrofuran and dihydrothiazole. Non-limiting examples of heterocyclic radicals include 2-pyrrolinyl, 3-pyrrolinyl, pyrrolindinyl, 1,3-dioxolanyl, 2H-pyranyl, 4H-pyranyl, piperidinyl, 1,4-dioxanyl, morpholinyl, 1,4-dithianyl, thiomorpholinyl, and the like. Said "heterocycly", group may be substituted as defined herein. Preferred heterocyclic radicals include five to twelve membered fused or unfused radicals.

The term "heteroaryl" embraces fully unsaturated heteroatom-containing ring-shaped aromatic radicals having from 4 through 15 ring members selected from carbon, nitrogen, sulfur and oxygen, wherein at least one ring atom is a heteroatom. Heteroaryl radicals may contain one, two or three rings wherein such rings may be attached in a pendant manner or may be fused. Examples of "heteroaryl" radicals, include the unsaturated heteromonocyclyl group of 5 to 6 contiguous members containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heteroaryl" group may be substituted as defined herein. Preferred heteroaryl radicals include five and six membered unfused radicals. Non-limiting examples of heteroaryl radicals include 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, 1,2,3-triazin-4-yl, and 1,2,3-triazin-5-yl, and the like.

The term "sulfonyl", whether used alone or linked to other terms such as alkylsulfonyl, denotes respectively divalent radicals —SO$_2$—. "Alkylsulfonyl", embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals attached to a sulfonyl radical, where haloalkyl is defined as above. "Haloalkylsulfonylalkyl", embraces haloalkylsulfonyl radicals attached to an alkyl radical, where alkyl is defined as above.

The term "amidosulfonyl" embraces amino, monoalkylamino, dialkylamino, monocycloalkylamino, alkyl cycloalkylamino, dicycloalkylamino, N-alkyl-N-arylamino, arylamino, aralkylamino, nitrogen containing heterocyclyl, heterocyclylamino, N-alkyl-N-heterocyclylamino, heteroarylamino, and heteroaralkylamino radicals, attached to one of two unshared bonds in a sulfonyl radical.

The term "sulfinyl", whether used alone or linked to other terms such as alkylsulfinyl, denotes respectively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfinylalkyl", embraces haloalkylsulfinyl radicals attached to an alkyl radical, where alkyl is defined as above.

The term "aralkyl" embraces aryl-substituted alkyl radicals. Preferable aralkyl radicals are "aralkyl" radicals having aryl radicals attached to alkyl radicals having one to six carbon atoms. Examples of such radicals include benzyl, diphenylmethyl, triphenylmethyl, phenylethyl and diphenylethyl. The terms benzyl and phenylmethyl are interchangeable.

The term "heteroaralkyl" embraces heteroaryl-substituted alkyl radicals wherein the heteroaralkyl radical may be additionally substituted with three or more substituents as defined above for aralkyl radicals. The term "perhaloaralkyl" embraces aryl-substituted alkyl radicals wherein the aralkyl radical is substituted with three or more halo radicals as defined above.

The term "aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above.

The term "aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above.

The term "cycloalkyl" embraces radicals having three to 15 carbon atoms. More preferred cycloalkyl radicals are "cycloalkyl" radicals having three to seven carbon atoms. Examples include radicals such as cyclopropyl, cyclobutyl, cyclopentyl, cyclohexyl and cycloheptyl. The term cycloalkyl embraces radicals having seven to 15 carbon atoms and having two to four rings. Examples include radicals such as norbornyl (i.e., bicyclo[2.2.1]heptyl) and adamantyl. The term "cycloalkylalkyl" embraces cycloalkyl-substituted alkyl radicals. Preferable cycloalkylalkyl radicals are "cycloalkylalkyl" radicals having cycloalkyl radicals attached to alkyl radicals having one to six carbon atoms. Examples of such radicals include cyclohexylhexyl. The term "cycloalkenyl" embraces radicals having three to ten carbon atoms and one or more carbon-carbon double bonds. Preferred cycloalkenyl radicals are "cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. More preferred halocycloalkyl radicals are "halocycloalkyl" radicals having three to about eight carbon atoms. Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals.

The term "cycloalkoxy" embraces cycloalkyl radicals attached to an oxy radical. Examples of such radicals includes cyclohexoxy and cyclopentoxy. The term "cycloalkoxyalkyl" also embraces alkyl radicals having one or more cycloalkoxy radicals attached to the alkyl radical, that is, to form monocycloalkoxyalkyl and dicycloalkoxyalkyl radicals. Examples of such radicals include cyclohexoxyethyl. The "cycloalkoxy" radicals may be further substituted with one or more halo atoms, such as fluoro, chloro or bromo, to provide "halocycloalkoxy" and "halocycloalkoxyalkyl" radicals.

The term "cycloalkylalkoxyl" embraces cycloalkyl radicals attached to an alkoxy radical. Examples of such radicals includes cyclohexylmethoxy and cyclopentylmethoxy.

The term "cycloalkenyloxy" embraces cycloalkenyl radicals attached to an oxy radical. Examples of such radicals includes cyclohexenyloxy and cyclopentenyloxy. The term "cycloalkenyloxyalkyl" also embraces alkyl radicals having one or more cycloalkenyloxy radicals attached to the alkyl radical, that is, to form monocycloalkenyloxyalkyl and dicycloalkenyloxyalkyl radicals. Examples of such radicals include cyclohexenyloxyethyl. The "cycloalkenyloxy" radicals may be further substituted with one or more halo atoms, such as fluoro, chloro or bromo, to provide "halocycloalkenyloxyl" and "halocycloalkenyloxyalkyl" radicals.

The term "cycloalkylenedioxy" radicals denotes cycloalkylene radicals having at least two oxygens bonded to a single cycloalkylene group. Examples of "alkylenedioxy" radicals include 1,2-dioxycyclohexylene.

The term "cycloalkylsulfinyl", embraces cycloalkyl radicals attached to a sulfinyl radical, where cycloalkyl is defined as above. "Cycloalkylsulfinylalkyl", embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalkylsulfonyl radicals attached to an alkyl radical, where alkyl is defined as above.

The term "cycloalkylalkanoyl" embraces radicals wherein one or more of the cycloalkyl carbon atoms are substituted with one or more carbonyl radicals as defined below. Specifically embraced are monocarbonylcycloalkyl and dicarbonylcycloalkyl radicals. Examples of monocarbonylcycloalkyl radicals include cyclohexylcarbonyl, cyclohexylacetyl, and cyclopentylcarbonyl. Examples of dicarbonylcycloalkyl radicals include 1,2-dicarbonylcyclohexane.

The term "alkylthiol" embraces radicals containing a linear or branched alkyl radical, of one to ten carbon atoms, attached to a divalent sulfur atom. More preferred alkylthio radicals are "alkylthio" radicals having one to six carbon atoms. An example of "alkylthiol" is methylthio ($CH_3$—S—). The "alkylthio" radicals may be further substituted with one or more halo atoms, such as fluoro, chloro or bromo, to provide "haloalkylthiol" radicals. Examples of such radicals include fluoromethylthio, chloromethylthio, trifluoromethylthio, difluoromethylthio, trifluoroethylthio, fluoroethylthio, tetrafluoroethylthio, pentafluoroethylthio, and fluoropropylthio.

The term "alkyl aryl amino" embraces radicals containing a linear or branched alkyl radical, of one to ten carbon atoms, and one aryl radical both attached to an amino radical. Examples include N-methyl-4-methoxyaniline, N-ethyl-4-methoxyaniline, and N-methyl-4-trifluoromethoxyaniline.

The term alkylamino denotes "monoalkylamino" and "dialkylamino" containing one or two alkyl radicals, respectively, attached to an amino radical. One or two alkyl radicals of the alkylamino may be optionally substituted with hydrogen bonding substitutents selected from the group consisting of hydroxy, amino, monoalkylamino, dialkylamino, amidino, guanidino, thiol, and alkoxy provided the alkyl radicals comprises two or more carbons.

The terms arylamino denotes "monoarylamino" and "diarylamino" containing one or two aryl radicals, respectively, attached to an amino radical. Examples of such radicals include N-phenylamino and N-naphthylamino.

The term "aralkylamino", embraces aralkyl radicals attached to an amino radical, where aralkyl is defined as above. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "arylsulfinyl" embraces radicals containing an aryl radical, as defined above, attached to a divalent S(O) atom. The term "arylsulfinylalkyl" denotes arylsulfinyl radicals attached to a linear or branched alkyl radical, of one to ten carbon atoms.

The term "arylsulfonyl", embraces aryl radicals attached to a sulfonyl radical, where aryl is defined as above. "arylsulfonylalkyl", embraces arylsulfonyl radicals attached to an alkyl radical, where alkyl is defined as above. The term "heteroarylsulfinyl" embraces radicals containing an heteroaryl radical, as defined above, attached to a divalent S(O) atom. The term "heteroarylsulfinylalkyl" denotes heteroarylsulfinyl radicals attached to a linear or branched alkyl radical, of one to ten carbon atoms. The term "Heteroarylsulfonyl", embraces heteroaryl radicals attached to a sulfonyl radical, where heteroaryl is defined as above. "Heteroarylsulfonylalkyl", embraces heteroarylsulfonyl radicals attached to an alkyl radical, where alkyl is defined as above.

The term "aryloxy" embraces aryl radicals, as defined above, attached to an oxygen atom. Examples of such radicals include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 3-pentafluoroethylphenoxy, 3-(1,1,2,2-tetrafluoroethoxy)-phenoxy, and 4-tert-butylphenoxy.

The term "aroyl" embraces aryl radicals, as defined above, attached to an carbonyl radical as defined above. Examples of such radicals include benzoyl and toluoyl.

The term "aralkanoyl" embraces aralkyl radicals, as defined herein, attached to an carbonyl radical as defined above. Examples of such radicals include, for example, phenylacetyl.

The term "aralkoxy" embraces oxy-containing aralkyl radicals attached through an oxygen atom to other radicals. More preferred aralkoxy radicals are "aralkoxyl" radicals having phenyl radicals attached to alkoxy radical as described above. Examples of such radicals include benzyloxy, 1-phenylethoxy, 3-trifluoromethoxybenzyloxy, 3-trifluoromethylbenzyloxy, 3,5-difluorobenzyloxy, 3-bromobenzyloxy, 4-propylbenzyloxy, 2-fluoro-3-trifluoromethylbenzyloxy, and 2-phenylethoxy.

The term "aryloxyalkyl" embraces aryloxy radicals, as defined above, attached to an alkyl group. Examples of such radicals include phenoxymethyl.

The term "haloaryloxyalkyl" embraces aryloxyalkyl radicals, as defined above, wherein one to five halo radicals are attached to an aryloxy group.

The term "heteroaroyl" embraces heteroaryl radicals, as defined above, attached to an carbonyl radical as defined above. Examples of such radicals include furoyl and nicotinyl.

The term "heteroaralkanoyl" embraces heteroaralkyl radicals, as defined herein, attached to an carbonyl radical as defined above. Examples of such radicals include, for example, pyridylacetyl and furylbutyryl.

The term "heteroaralkoxy" embraces oxy-containing heteroaralkyl radicals attached through an oxygen atom to other radicals. More preferred heteroaralkoxy radicals are "heteroaralkoxy" radicals having heteroaryl radicals attached to alkoxy radical as described above. The term "heterocyclylalkoxy" embraces oxy-containing heterocyclylalkyl radicals attached through an oxygen atom to other radicals.

The term "haloheteroaryloxyalkyl" embraces heteroaryloxyalkyl radicals, as defined above, wherein one to four halo radicals are attached to an heteroaryloxy group.

The term "heteroarylamino" embraces heteroaryl radicals, as defined above, attached to an amino group. Examples of such radicals include pyridylamino. The term "heterocyclylamino" embraces heterocyclyl radicals, as defined above, attached to an amino group.

The term "heteroaralkylamino" embraces heteroaralkyl radicals, as defined above, attached to an amino group. Examples of such radicals include pyridylmethylamino. The term "heterocyclylalkylamino" embraces heterocyclylalkyl radicals, as defined above, attached to an amino group.

The term "heteroaryloxy" embraces heteroaryl radicals, as defined above, attached to an oxy group. Examples of such radicals include 2-thiophenyloxy, 2-pyrimidyloxy, 2-pyridyloxy, 3-pyridyloxy, and 4-pyridyloxy. The term "heterocyclyloxy" embraces heterocyclyl radicals, as defined above, attached to an oxy group.

The term "heteroaryloxyalkyl" embraces heteroaryloxy radicals, as defined above, attached to an alkyl group. Examples of such radicals include 2-pyridyloxymethyl, 3-pyridyloxyethyl, and 4-pyridyloxymethyl. The term "heterocyclyloxyalkyl" embraces heterocyclyloxy radicals, as defined above, attached to an alkyl group.

The term "arylthio" embraces aryl radicals, as defined above, attached to an sulfur atom. Examples of such radicals include phenylthio.

The term "arylthioalkyl" embraces arylthio radicals, as defined above, attached to an alkyl group. Examples of such radicals include phenylthiomethyl.

The term "alkylthioalkyl" embraces alkylthio radicals, as defined above, attached to an alkyl group. Examples of such radicals include methylthiomethyl. The term "alkoxyalkyl" embraces alkoxy radicals, as defined above, attached to an alkyl group. Examples of such radicals include methoxymethyl.

The term "carbonyl" denotes a carbon radical having two of the four covalent bonds shared with an oxygen atom. The term "carboxy" embraces a hydroxyl radical, as defined above, attached to one of two unshared bonds in a carbonyl group. The term "carboxamido" embraces amino, monoalkylamino, dialkylamino, monocycloalkylamino, alkylcycloalkylamino, dicycloalkylamino, N-alkyl-N-arylamino, arylamino, aralkylamino, nitrogen containing heterocyclyl, heterocyclylamino, N-alkyl-N-heterocyclylamino, heteroarylamino, and heteroaralkylamino radicals, attached to one of two unshared bonds in a carbonyl group. The term "carboxamidoalkyl" embraces carboxamido radicals, as defined above, attached to an alkyl group. The term "carboxyalkyl" embraces a carboxy radical, as defined above, attached to an alkyl group. The term "carboalkoxy" embraces alkoxy radicals, as defined above, attached to one of two unshared bonds in a carbonyl group. The term "carboaralkoxy" embraces aralkoxy radicals, as defined above, attached to one of two unshared bonds in a carbonyl group. The term "monocarboalkoxyalkyl" embraces one carboalkoxy radical, as defined above, attached to an alkyl group. The term "dicarboalkoxyalkyl" embraces two carboalkoxy radicals, as defined above, attached to an alkylene group. The term "monocyanoalkyl" embraces one cyano radical, as defined above, attached to an alkyl group. The term "dicyanoalkylene" embraces two cyano radicals, as defined above, attached to an alkyl group. The term "carboalkoxycyanoalkyl" embraces one cyano radical, as defined above, attached to an carboalkoxyalkyl group.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like. The term "haloalkanoyl" embraces one or more halo radicals, as defined herein, attached to an alkanoyl radical as defined above. Examples of such radicals include, for example, chloroacetyl, trifluoroacetyl, bromopropanoyl, and heptafluorobutanoyl.

The term "phosphono" embraces a pentavalent phosphorus attached with two covalent bonds to an oxygen radical. The term "dialkoxyphosphono" denotes two alkoxy radicals, as defined above, attached to a phosphono radical with two covalent bonds. The term "diaralkoxyphosphono" denotes two aralkoxy radicals, as defined above, attached to a phosphono radical with two covalent bonds. The term "dialkoxyphosphonoalkyl" denotes dialkoxyphosphono radicals, as defined above, attached to an alkyl radical. The term "diaralkoxyphosphonoalkyl" denotes diaralkoxyphosphono radicals, as defined above, attached to an alkyl radical.

The term "amino" denotes a nitrogen atom containing two substituents such as hydrido, hydroxy or alkyl and having one covalent bond available for bonding to a single atom such as carbon. Examples of such amino radicals include, for example, —NH$_2$, —NHCH$_3$, —NHOH, and —NHOCH$_3$. The term "imino" denotes a nitrogen atom containing one substituent such as hydrido, hydroxy or alkyl and having two covalent bonds available for bonding to a single atom such as carbon. Examples of such imino radicals include, for example, =NH, =NCH$_3$, =NOH, and =NOCH$_3$. The term "imino carbonyl" denotes a carbon radical having two of the four covalent bond sites shared with an imino group. Examples of such imino carbonyl radicals include, for example, C=NH, C=NCH$_3$, C=NOH, and C=NOCH$_3$. The term "amidino" embraces a substituted or unsubstituted amino group bonded to one of two available bonds of an iminocarbonyl radical. Examples of such amidino radicals include, for example, NH$_2$—C=NH, NH$_2$—C=NCH$_3$, NH$_2$—C=NOCH$_3$, and CH$_3$NH—C=NOH. The term "guanidino" denotes an amidino group bonded to an amino group as defined above where said amino group can be bonded to a third group. Examples of such guanidino radicals include, for example, NH$_2$—C(NH)—NH—, NH$_2$—C(NCH$_3$)—NH—, NH$_2$—C(NOCH$_3$)—NH—, and CH$_3$NH—C(NOH)—NH—.

The term "sulfonium" denotes a positively charged trivalent sulfur atom where said sulfur is substituted with three carbon based groups such as alkyl, alkenyl, aralkyl, or aryl. The term "dialkyl sulfonium" denotes a sulfonium group where said sulfur is substituted with two alkyl groups. Examples of such dialkylsulfonium radicals include, for example, $(CH_3)_2S^+$—. The term "dialkyl sulfonium alkyl" denotes a dialkyl sulfonium group where said group is bonded to one bond of an alkylene group as defined above. Examples of such dialkylsulfoniumalkyl radicals include $(CH_3)_2S^+$—$CH_2CH_2$—.

The term "phosphonium" denotes a positively charged tetravalent phosphorus atom where said phosphorus is substituted with four carbon based groups such as alkyl, alkenyl, aralkyl, or aryl. The term "trialkyl phosphonium" denotes a phosphonium group where said phosphorus is substituted with three alkyl groups. Examples of such trialkylphosphonium radicals include, for example, $(CH_3)_3P+$—.

Said "alkyl", "alkenyl", "alkynyl", "alkanoyl", "alkylene", "alkenylene", "hydroxyalkyl", "haloalkyl", "haloalkylene", "haloalkenyl", "alkoxy-", "alkenyloxyl", "alkenyloxyalkyl", "alkoxyalkyl", "aryl", "perhaloaryl", "haloalkoxy", "haloalkoxyalkyl", "haloalkenyloxy", "haloalkenyloxyalkyl", "alkylenedioxy", "haloalkylenedioxy", "heterocyclyl", "heteroaryl", "hydroxyhaloalkyl", "alkylsulfonyl", "haloalkylsulfonyl", "alkylsulfonylalkyl", "haloalkylsulfonylalkyl", "alkylsulfinyl", "alkylsulfinylalkyl", "haloalkylsulfinylalkyl", "aralkyl", "heteroaralkyl", "perhaloaralkyl", "aralkylsulfonyl", "aralkylsulfonylalkyl", "aralkylsulfinyl", "aralkylsulfinylalkyl", "cycloalkyl", "cycloalkylalkanoyl", "cycloalkylalkyl", "cycloalkenyl", "halocycloalkyl", "halocycloalkenyl", "cycloalkylsulfinyl", "cycloalkylsulfinylalkyl", "cycloalkylsulfonyl", "cycloalkylsulfonylalkyl", "cycloalkoxyl", "cycloalkoxyalkyl", "cycloalkylalkoxy", "cycloalkenyloxy", "cycloalkenyloxyalkyl", "cycloalkylenedioxy", "halocycloalkoxyl", "halocycloalkoxyalkyl", "halocycloalkenyloxy", "halocycloalkenyloxyalkyl", "alkylthio", "haloalkylthiol", "alkylsulfinyl", "amino", "oxy", "thio", "alkylamino", "arylamino", "aralkylamino", "arylsulfinyl", "arylsulfinylalkyl", "arylsulfonyl", "arylsulfonylalkyl", "heteroarylsulfinyl", "heteroarylsulfinylalkyl", "heteroarylsulfonyl", "heteroarylsulfonylalkyl", "heteroarylamino", "heteroaralkylamino", "heteroaryloxy", "heteroaryloxylalkyl", "aryloxy", "aroyl", "aralkanoyl", "aralkoxy", "aryloxyalkyl", "haloaryloxyalkyl", "heteroaroyl", "heteroaralkanoyl", "heteroaralkoxy", "heteroaralkoxyalkyl", "arylthio", "arylthioalkyl", "alkoxyalkyl", "acyl", "amidino", "guanidino", "dialkylsulfonium", "trialkylphosphonium", and "dialkylsulfoniumalkyl" groups defined above may optionally have 1 or more non-hydrido substituents such as amidino, guanidino, dialkylsulfonium, trialkylphosphonium, dialkylsulfoniumalkyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, heteroaryloxy, heteroaryloxylalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroaralkyl, arylalkenyl, heteroarylalkenyl, carboxyalkyl, carboalkoxy, alkoxycarbonyl, carboaralkoxy, carboxamido, carboxamidoalkyl, cyano, carbohaloalkoxy, phosphono, phosphonoalkyl, diaralkoxyphosphono, and diaralkoxyphosphonoalkyl.

The term "spacer" can include a covalent bond and a linear moiety having a backbone of 1 to 7 contiguous atoms. The spacer may have 1 to 7 atoms of a univalent or multi-valent chain. Univalent chains may be constituted by a radical selected from $=C(H)$—, $=C(R^{2a})$—, O—, —S—, —S(O)—, —S(O)$_2$—, —NH—, —N(R$^{2a}$)—, —N=, —CH(OH)—, $=C(OH)$—, —CH(OR$^{2a}$)—, $=C(OR^{2a})$—, and —C(O)— wherein R$^2$, is selected from alkyl, alkenyl, alkynyl, aryl, heteroaryl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl. Multi-valent chains may consist of a straight chain of 1 or 2 or 3 or 4 or 5 or 6 or 7 atoms or a straight chain of 1 or 2 or 3 or 4 or 5 or 6 atoms with a side chain. The chain may be constituted of one or more radicals selected from: alkylene, alkenyl, —O—, —O—CH$_2$—, —S—CH$_2$—, —CH$_2$CH$_2$—, ethenyl, —CH=CH(OH)—, —OCH$_2$O—, —O(CH$_2$)$_2$O—, —NHCH$_2$—, —OCH(R$^{2a}$)O—, —O(CH$_2$CHR$^{2a}$)O—, —OCF$_2$O—, —O(CF$_2$)$_2$O—, —S—, S(O)—, —S(O)$_2$—, —N(H)—, —N(H)O—, —N(R$^{2a}$)O—, —N(R$^{2a}$)—, —C(O)—, —C(O)NH—, —C(O)NR$^{2a}$—, —N=, —OCH$_2$—, —SCH$_2$—, S(O)CH$_2$—, —CH$_2$C(O)—, —CH(OH)—, $=C(OH)$—, —CH(OR$^{2a}$)—, $=C(OR^{2a})$—, S(O)$_2$CH$_2$—, and —NR$^{2a}$CH$_2$— and many other radicals defined above or generally known or ascertained by one of skill-in-the art. Side chains may include substituents such as 1 or more non-hydrido substituents such as amidino, guanidino, dialkylsulfonium, trialkylphosphonium, dialkylsulfoniumalkyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, heteroaryloxy, heteroaryloxylalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, carboaralkoxy, carboxamido, carboxamidoalkyl, cyano, carbohaloalkoxy, phosphono, phosphonoalkyl, diaralkoxyphosphono, and diaralkoxyphosphonoalkyl.

Formula A Embodiment

In addition to those compounds falling within the scope of Formula I, in another embodiment, the present invention is directed to compounds falling within Formula A. In general, the compounds of formula I are a subset of compounds falling within Formula I. In this embodiment of the invention, the symbols employed to depict the chemical groups for Formula A correspond to the symbols employed to depict the chemical groups for Formula I as follows:

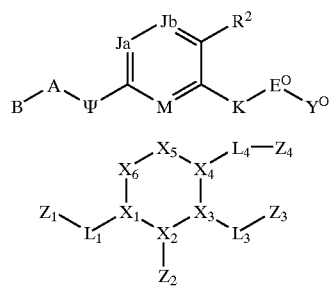

Formula I

Formula A wherein
$X_1$ corresponds to the ring atom adjacent to M and Ja;
$X_2$ corresponds to M;
$X_3$ corresponds to the ring atom that is the point of attachment for K;
$X_4$ corresponds to the ring atom that is the point of attachment for $R^2$;
$X_5$ corresponds to Jb;
$X_6$ corresponds to Ja;
$L_1$ corresponds to —A—Ψ—;
$Z_1$ corresponds to B;
$L_3$ corresponds to —K—$E^O$—;

$Z_3$ corresponds to $Y^O$;
$L_4$ and $Z_4$ corresponds to $R^2$.

In one embodiment of the present invention, the compounds correspond to Formula A:

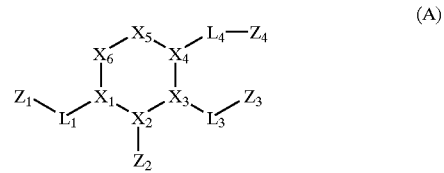

(A)

wherein:
$X_1$, $X_2$, $X_3$, $X_4$, $X_5$, and $X_6$ are each ring atoms defining a 6 membered heterocyclic or aromatic ring;
$X_1$, $X_2$, and $X_4$ are independently carbon or nitrogen;
$X_3$ is carbon;
$X_5$ and $X_6$ are independently carbon, nitrogen, oxygen or sulfur, provided at least one of $X_1$, $X_4$, and $X_6$ is other than carbon when $X_2$ is carbon;
$L_1$, $L_3$ and $L_4$ are linkages through which $Z_1$, $Z_3$, and $Z_4$, respectively, are covalently bonded to different ring atoms of the 6 membered heterocyclic or aromatic ring defined by $X_1$, $X_2$, $X_3$, $X_4$, $X_5$, and $X_6$, wherein $Z_1$ is covalently bonded to $X_1$, $Z_3$ is covalently bonded to $X_3$, and $Z_4$ is covalently bonded to $X_4$, each of $L_1$, $L_3$ and $L_4$ independently being a covalent bond or comprising one or more atoms through which $Z_1$, $Z_3$, and $Z_4$ are covalently bonded to $X_1$, $X_3$ and $X_4$, respectively;

$Z_3$ is a substituted hydrocarbyl, or a 5 or 6 membered substituted heterocyclic or aromatic ring, the substituents of the hydrocarbyl or ring comprising an amidine, guanidine, amino, or aminoalkyl group, the ring atoms of the 5 or 6 membered heterocyclic or aromatic ring of $Z_3$ being carbon, sulfur, nitrogen, or oxygen, wherein the 5 or 6 membered ring is optionally substituted at any position with halogen, hydroxy, or alkyl;

$Z_4$ comprises hydrocarbyl, substituted hydrocarbyl or a 5 or 6-membered heterocyclic ring, the ring atoms of the 5 or 6-membered heterocyclic ring being carbon, sulfur, nitrogen or oxygen;

$Z_1$ is hydrogen, hydrocarbyl, or substituted hydrocarbyl; and $Z_2$ is a hydrogen bond acceptor covalently or datively bonded to $X_2$.

In yet another embodiment the compounds correspond to Formula A wherein:
$X_1$, $X_2$, $X_3$, $X_4$, $X_5$, and $X_6$ are each ring atoms defining a 6 membered heterocyclic or aromatic ring;
$X_1$, $X_2$, and $X_4$ are independently carbon or nitrogen;
$X_3$ is carbon;
$X_5$ and $X_6$ are independently carbon, nitrogen, oxygen or sulfur, provided at least one of $X_1$, $X_4$, and $X_6$ is other than carbon when $X_2$ is carbon;
$L_1$, $L_3$ and $L_4$ are linkages through which $Z_1$, $Z_3$, and $Z_4$, respectively, are covalently bonded to different ring atoms of the 6 membered heterocyclic or aromatic ring defined by $X_1$, $X_2$, $X_3$, $X_4$, $X_5$, and $X_6$, wherein Z, is covalently bonded to $X_1$, $Z_3$ is covalently bonded to $X_3$, and $Z_4$ is covalently bonded to $X_4$, each of $L_1$, $L_3$ and $L_4$ independently being a covalent bond or comprising one or more atoms through which $Z_1$, $Z_3$, and $Z_4$ are covalently bonded to $X_1$, $X_3$ and $X_4$, respectively;

$Z_3$ comprises a 5 or 6 membered heterocyclic or aromatic ring substituted with an amidine group, the ring atoms of the 5 or 6 membered heterocyclic or aromatic ring of $Z_3$ being carbon, sulfur, nitrogen, or oxygen, wherein the 5 or 6 membered ring is optionally substituted at any position with halogen, hydroxy, or alkyl;

$Z_4$ comprises a 5 or 6 membered heterocyclic or carboxylic ring, the ring atoms of the 5 or 6 membered heterocyclic or carboxylic ring of $Z_4$ being carbon, nitrogen, oxygen, or sulfur;

$Z_1$ is hydrocarbyl or substituted hydrocarbyl; and $Z_2$ is a hydrogen bond acceptor covalently or datively bonded to $X_2$.

In one preferred embodiment, when $X_2$ is carbon $Z_2$ is hydrogen, fluorine, oxygen, or sulfur. A further embodiment provides compounds that when $X_2$ is nitrogen $Z_2$ is hydrogen, an electron pair, or a hydrogen bond acceptor. In yet another embodiment when $X_2$ is nitrogen $Z_2$ is hydrogen or oxygen. Exemplary 6 membered heterocyclic or aromatic rings defined by $X_1$, $X_2$, $X_3$, $X_4$, $X_5$, and $X_6$ include pyridone, pyrimidone, triazinone, azaquinone, pyrazinone, isoxazinone, dihydrotriazinedione, pyridine, pyrazine, pyrimidine, triazine. For each of these embodiments, $X_5$ may be optionally substituted with a halogen.

Exemplary $Z_1$ substituents include substituted or unsubstituted $C_2$ to $C_8$ alkyl, substituted or unsubstituted $C_3$ to $C_6$ cycloalkyl and substituted or unsubstituted phenyl. Exemplary preferred $Z_1$ substituents include substituted or unsubstituted cyclopropyl, isopropyl, cyclobutyl, isobutyl, sec-butyl, methyl, ethyl, and phenyl.

Exemplary $L_1$ linkages include —$X_9$NH— wherein $X_9$ is covalently bonded directly to $Z_1$ and $X_9$ is a direct bond or —$(CH_2)_m$— wherein m is 1 to 5. An exemplary preferred $L_1$ linkage is —$X_9$NH— wherein $X_9$ is covalently bonded directly to $Z_1$ and $X_9$ is a direct bond or —$(CH_2)_m$— wherein m is 1 to 2. A particularly exemplary $L_1$ linkage is —$X_9$NH— wherein $X_9$ is covalently bonded directly to $Z_1$ and is a direct bond. In a further embodiment, $L_1$ may covalently bond to $X_6$ to form a fused ring.

An exemplary $Z_4$ group is a substituted, 6 member, carbocyclic aromatic ring. In an exemplary preferred embodiment, $Z_4$ has the following structure:

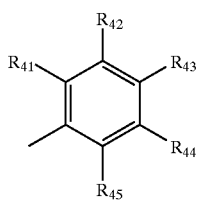

Wherein

Exemplary $R_{42}$ substituent is amino.

Exemplary $R_{44}$ substituents include hydrogen, hydrocarbyl, substituted hydrocarbyl, heterocyclo, halogen or a substituted or unsubstituted heteroatom selected from nitrogen, oxygen, sulfur and phosphorous. Exemplary preferred $R_{44}$ substituents include hydrogen, hydrocarbyl, substituted hydrocarbyl, heteroaryl, heterocyclo, halogen, acetamido, guanidino, hydroxy, nitro, amino, amidosulfonyl, acylamido, hydrocarbyloxy, substituted hydrocarbyloxy, hydrocarbylthio, substituted hydrocarbylthio, hydrocarbylsulfonyl, or substituted hydrocarbylsulfonyl. Particularly exemplary $R_{44}$ substituents include hydroxy, alkylsulfonyl, haloalkyl, carboxamidoalkyl, or carboxamidoalkylaryl.

Exemplary $R_{41}$, $R_{43}$ and $R_{45}$ substituents include hydrogen, and hydrocarbyl, substituted hydrocarbyl, halogen or an optionally substituted hetero atom selected from the group consisting of oxygen, nitrogen, and sulfur. Particularly exemplary $R_{41}$, $R_{43}$ and $R_{45}$ substituents include hydrogen and halogen.

An exemplary $L_4$ linkage is —$(CH_2)_m$— where m is 0 to 5. A more exemplary $L_4$ linkage is —$(CH_2)_m$— where m is 0 to 2. An even more exemplary $L_4$ linkage is a direct bond.

In a particularly preferred embodiment, the 5 or 6 membered heterocyclic or aromatic ring comprising $Z_3$ is substituted with a derivatized amidine which, upon hydrolysis, oxidation, reduction or elimination yields an amidine group. In yet another preferred embodiment, the 5 or 6 membered heterocyclic or aromatic ring comprising $Z_3$ is substituted with a amidine group. In a particularly preferred embodiment, $Z_3$ is benzene substituted with either an amidine group or with a derivatized amidine which, upon hydrolysis, oxidation, reduction or elimination yields an amidine group. Additionally, in any embodiment set forth, $Z_3$ may be optionally substituted at any position with a halogen, alkyl, hydroxy or any combination thereof. Exemplary substitutions include fluorine, methyl, hydroxy, $CF_3$ or any combination thereof.

Accordingly, in one embodiment $Z_3$ is —$R_{300}C(=NR_{301})$ $NR_{302}R_{303}$, wherein $R_{300}$ is a 6 membered carbocyclic aromatic ring, $R_{301}$, $R_{302}$, $R_{303}$ are independently selected from hydrogen, optionally substituted hyrocarbyl, and optionally substituted hetero atoms selected from the group consisting of oxygen, nitrogen, phosphorous and sulfur.

In yet another embodiment $Z_3$ is a benzamidine derivative which hydrolyzes under physiological conditions to form benzamidine, the benzamidine derivative having the formula

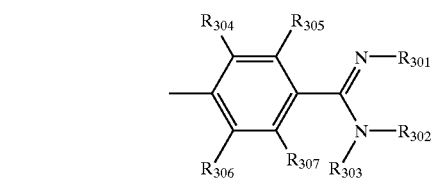

$R_{301}$, $R_{302}$, and $R_{303}$ are independently selected from the group consisting of hydrogen, $C(=O)R$, $S(=O)OR$, $S(=O)$ $SR$, $S(=O)_2OR$, $S(=O)_2SR$ and alkene, provided that the carbon atom directly bonded to the amidine is $sp^2$ hybridized, provided, however, at least one of $R_{301}$, $R_{302}$, and $R_{303}$ is other than hydrogen;

R is hydrocarbyl, substituted hydrocarbyl, or heterocycle;

$R_{304}$ is halogen, hydrogen, hydroxyl, alkyl, sulfhydryl, alkoxy, and thioalkyl;

$R_{305}$ is oxygen, sulfur, halogen, hydrogen, hydroxyl, alkyl, sulfhydryl, alkoxy, and thioalkyl;

$R_{306}$ is halogen, hydrogen, hydroxyl, alkyl, sulfhydryl, alkoxy, and thioalkyl; and $R_{307}$ is oxygen, sulfur, halogen, hydrogen, hydroxyl, alkyl, sulfhydryl, alkoxy, and thioalkyl.

In still a further embodiment, $Z_3$ is a benzamidine derivative which oxidizes under physiological conditions to form benzamidine, the benzamidine derivative having the formula

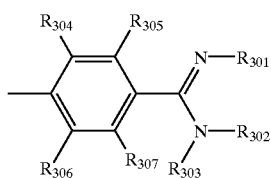

$R_{301}$, $R_{302}$, and $R_{303}$ are independently selected from the group consisting of hydrogen, optionally substituted hydrocarbyl and aryl, provided, however, (i) at least one of $R_{301}$, $R_{302}$, and $R_{303}$ is other than hydrogen and (ii) the carbon atom directly bonded to the amidine is Sp$^3$ hybridized when $R_{301}$, $R_{302}$, and $R_{303}$ is optionally substituted hydrocarbyl;

$R_{304}$ is halogen, hydrogen, hydroxyl, alkyl, sulfhydryl, alkoxy, and thioalkyl;

$R_{305}$ is oxygen, sulfur, halogen, hydrogen, hydroxyl, alkyl, sulfhydryl, alkoxy, and thioalkyl;

$R_{306}$ is halogen, hydrogen, hydroxyl, alkyl, sulfhydryl, alkoxy, and thioalkyl; and $R_{307}$ is oxygen, sulfur, halogen, hydrogen, hydroxyl, alkyl, sulfhydryl, alkoxy, and thioalkyl.

In a further embodiment, $Z_3$ is a benzamidine derivative which is reduced under physiological conditions to form benzamidine, the benzamidine derivative having the formula

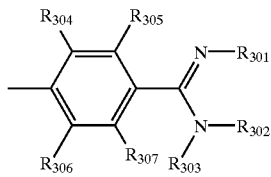

$R_{301}$, $R_{302}$, and $R_{303}$ are independently hydrogen, —OR, —SR, —NR, or —N(R)$_2$, wherein each R is independently optionally substituted hydrocarbyl, or heterocylo, provided, however, at least one of $R_{301}$, $R_{302}$, and $R_{303}$ is other than hydrogen;

$R_{304}$ is halogen, hydrogen, hydroxyl, alkyl, sulfhydryl, alkoxy, and thioalkyl;

$R_{305}$ is oxygen, sulfur, halogen, hydrogen, hydroxyl, alkyl, sulfhydryl, alkoxy, and thioalkyl;

$R^{306}$ is halogen, hydrogen, hydroxyl, alkyl, sulfhydryl, alkoxy, and thioalkyl; and $R_{307}$ is oxygen, sulfur, halogen, hydrogen, hydroxyl, alkyl, sulfhydryl, alkoxy, and thioalkyl.

In yet another embodiment, $Z_3$ is a benzamidine derivative which undergoes an elimination reaction under physiological conditions to form benzamidine, the benzamidine derivative having the formula

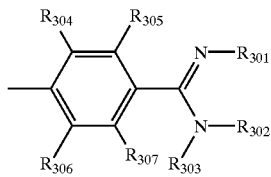

$R_{301}$, $R_{302}$, and $R_{303}$ are independently (i) hydrogen, (ii) substituted hydrocarbyl wherein the carbon bonded to the amidine group is substituted with —OCR$_a$, —SR$_a$, —NR$_a$, or —N(R$_a$)$_2$, wherein each R$_a$ is independently —C(O)R$_b$, —C(O)NR$_b$, —C(O)N(R$_b$)$_2$ and each R$_b$ is independently hydrocarbyl, substituted hydrocarbyl or heterocyclo, (iii) substituted alkyl with the carbon atom beta to the point of attachment to the amidine group being an unsaturated electron withdrawing group, provided, at least one of $R_{301}$, $R_{302}$, and $R_{303}$ is other than hydrogen;

$R_{304}$ is halogen, hydrogen, hydroxyl, alkyl, sulfhydryl, alkoxy, and thioalkyl;

$R_{305}$ is oxygen, sulfur, halogen, hydrogen, hydroxyl, alkyl, sulfhydryl, alkoxy, and thioalkyl;

$R_{306}$ is halogen, hydrogen, hydroxyl, alkyl, sulfhydryl, alkoxy, and thioalkyl; and $R_{307}$ is oxygen, sulfur, halogen, hydrogen, hydroxyl, alkyl, sulfhydryl, alkoxy, and thioalkyl.

Exemplary L$_3$ linkages include a glycine derivative, an alanine derivative, an amino derivative, and a sulfonyl derivative. A more exemplary L$_3$ linkage is a glycine derivative.

In one preferred embodiment, the compounds corresponding to formula (A) are represented by the following structure:

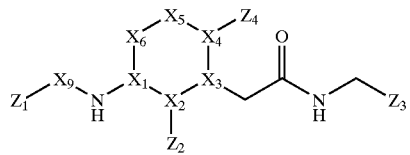

Exemplary substituents of compounds having this structure for each of $X_1$, $X_2$, $X_3$, $X_4$, $X_5$, and $X_6$ are as described for structural formula (A). Preferably, $X_9$ is a direct bond or —(CH$_2$)$_m$— where m is 1 or 2. Exemplary $Z_1$, $Z_2$, $Z_3$, and $Z_4$ groups are also as described for structural formula (A).

In yet another embodiment, compounds represented by structural formula A may form fused rings with the following structure:

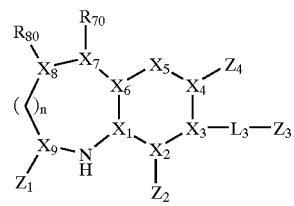

wherein

Exemplary groups for $Z_1$, $Z_2$, $Z_3$, $Z_4$, $L_3$, $X_1$, $X_2$, $X_3$, $X_4$, and $X_5$ are as defined above;

$X_6$ is independently carbon or nitrogen;

$X_7$ and $X_8$ are independently a covalent bond, carbon, nitrogen, oxygen or sulfur;

$X_9$ is carbon substituted with a methylene group or carbon substituted with an ethylene group wherein said methylene or ethylene group covalently links $X_9$ and $Z_1$;

n is 0 to 2; and $R_{70}$ and $R_{80}$ are independently selected from the group consisting of hydrogen, halogen, amino, hydrocarbyl, substituted hydrocarbyl, aryl, wherein aryl is phenyl either unsubstituted or substituted with hydroxy, amino, C1–C6 alkyl, C3–C8 cycloalkyl, or halogen provided that $R_{70}$ is not present when $X_7$ is a bond and $R_{80}$ is not present when $X_8$ is a bond; or $R_{70}$ and $R_{80}$, along with the ring atoms to which each is attached, form a 5 or 6 membered saturated ring.

Among the preferred embodiments, therefore, are compounds corresponding to formula A, wherein X. is a direct bond, $Z_4$ is a substituted, 6 member, carbocyclic aromatic ring, $Z_3$ is benzene substituted with a derivatized amidine which, upon hydrolysis, oxidation, reduction or elimination under physiological conditions yields an amidine group, and $Z_1$ is selected from the group consisting of cyclopropyl, isopropyl, methyl cyclobutyl, and phenyl. In an exemplary preferred embodiment, $Z_4$ is benzene substituted with two substituents, $R_{42}$ and $R_{44}$, and two ring atoms each of which is in the beta position relative to the ring atom of $Z_4$ through which $Z_4$ is covalently linked to $X_4$, wherein one of $R_{42}$ and $R^{44}$ is covalently bonded to one of said beta positions and the other of $R_{42}$ and $R_{44}$ is covalently bonded to the other of said beta positions. Preferred and exemplary $R_{42}$ and $R_{44}$ groups are as described above.

In yet another preferred embodiment, are compounds corresponding to formula A, wherein X, is a direct bond, $Z_4$ is a substituted, 6 member, carbocyclic aromatic ring, $Z_3$ is benzene substituted with an amidine group and $Z_1$ is selected from the group consisting of cyclopropyl, isopropyl, methyl cyclobutyl, and phenyl. In an exemplary preferred embodiment, $Z_4$ is benzene substituted with two substituents, $R_{42}$ and $R_{44}$, and two ring atoms each of which is in the beta position relative to the ring atom of $Z_4$ through which $Z_4$ is covalently linked to $X_4$, wherein one of $R_{42}$ and $R_{44}$ is covalently bonded to one of said beta positions and the other of $R_{42}$ and $R_{44}$ is covalently bonded to the other of said beta positions. Preferred and exemplary $R^{42}$ and $R_{44}$ groups are as described above.

Any prodrug compound of the present invention corresponding to structural formula A, having one or more prodrug moieties as part of the molecule, can be converted under physiological conditions to the biologically active drug by a number of chemical and biological mechanisms. In general terms, these prodrug conversion mechanisms are hydrolysis, reduction, oxidation, and elimation. For illustrative purposes, the following paragraphs detail prodrugs in which the prodrug moiety is covalently bonded to the amidine group on $Z_3$ as depicted in structural formula A above.

Conversion of the prodrug to the biologically active drug can be accomplished by hydrolysis of the prodrug moiety provided the prodrug moiety is chemically or enzymatically hydrolyzable with water. The reaction with water must further result in the removal of the prodrug moiety and the liberation of the biologically active drug. An example of a prodrug derivative at the amidine group would be a carbonyl derivative an example of which is N-acyl. Hydrolysis (the addition of water to the carbonyl of the amide nitrogen) results in freeing the amidine group of the drug by removal of the acyl as the carbon acid. Other suitable hydrolyzable derivatives of the amidine include carbonyl, thiocarbonyl, imine, enamine, and oxgenated sulfur.

Conversion of the prodrug to the biologically active drug can be additionally accomplished by reduction of the prodrug moiety provided the prodrug moiety is reducible under physiological conditions in the presence of a reducing enzymatic process. The reduction must further result in the removal of the prodrug moiety and the liberation of the biologically active drug. An example of a reducible prodrug derivative at the amidine group would be an oxygen containing group in which an oxygen is directly attached to the amidine. Reduction (the addition of hydrogen to amidino nitrogen and the oxygen) results in freeing the amidine group of the drug by removal of the oxygen as water or an alcohol. Other suitable reducible prodrug derivatives of the amidine include a nitrogen containing group, and a sulfur containing group, provided both nitrogen and sulfur are each in their most reduced state.

Conversion of the prodrug to the biologically active drug can be also be accomplished by oxidation of the prodrug moiety provided the prodrug moiety is oxidizable under physiological conditions in the presence of an oxidative enzymatic process. The oxidation must further result in the removal of the prodrug moiety and the liberation of the biologically active drug. An example of a oxidizable prodrug derivative at the amidine group would be hydrocarbyl containing unsaturation in the carbon beta to the carbon directly connected to the amidine group. Oxidation (the addition of oxygen) results in forming an oxygenated intermediate that breaks down freeing the amidine group of the drug with concurrent hydrolysis of the oxygenated hydrocarbyl residue. Other suitable oxidizable prodrug derivatives of the amidine include saturated hydrocarbyl, unsaturated substituted hydrocarbyl, aryl, and aralkyl.

Conversion of the prodrug to the biologically active drug can further be accomplished by elimination of the prodrug moiety provided the prodrug moiety is removed under physiological conditions with a chemical or biological reaction. The elimination must further result in the removal of the prodrug moiety and the liberation of the biologically active drug. An general example of an eliminateable prodrug derivative at the amidine group would be a hydrocarbyl containing an unsaturated electron withdrawing group bonded to the carbon beta to the carbon directly connected to the amidine. More specifically, for illustration purposes and exemplification, the hydrocarbyl group could have a cyano group beta to the carbon directly bonded to the amidino group. Elimination (a reaction in which a molecule fragments into two or more pieces) results in the freeing of the amidine group of the drug with concurrent removal of the unsaturated hydrocarbyl residue derived from the prodrug moiey. Other suitable eliminateable prodrug derivatives of the amidine include a hydrocarbyl substituted at the beta carbon with carbonyl, alkoxycarbonyl, amidocarbonyl, nitro, or sulfonyl or an alkyl group substituted with oxygen, nitrogen or sulfur at the carbon directly bonded to the amidine group.

Any prodrug compound of the present invention corresponding to formula A may undergo any combination of the above detailed mechanisms to convert the prodrug to the biologically active compound. For example, a particular compound may undergo hydrolysis, oxidation, elimination, and reduction to convert the prodrug to the biologically active compound. Equally, a particular compound may undergo only one these mechanisms to convert the prodrug to the biologically active compound.

In a particular preferred embodiment, the compound represented by Formula A above is selected from the group of compounds illustrated in Table 1 below.

TABLE 1

| Compound No. | Compound |
|---|---|
| 1 | (structure) |
| 2 | (structure) |
| 3 | (structure) |
| 4 | (structure) |
| 5 | (structure) |

TABLE 1-continued

| Compound No. | Compound |
|---|---|
| 6 | *(chemical structure)* |
| 7 | *(chemical structure)* |
| 8 | *(chemical structure)* |
| 9 | *(chemical structure)* |
| 10 | *(chemical structure)* |

TABLE 1-continued

| Compound No. | Compound |
|---|---|
| 11 | 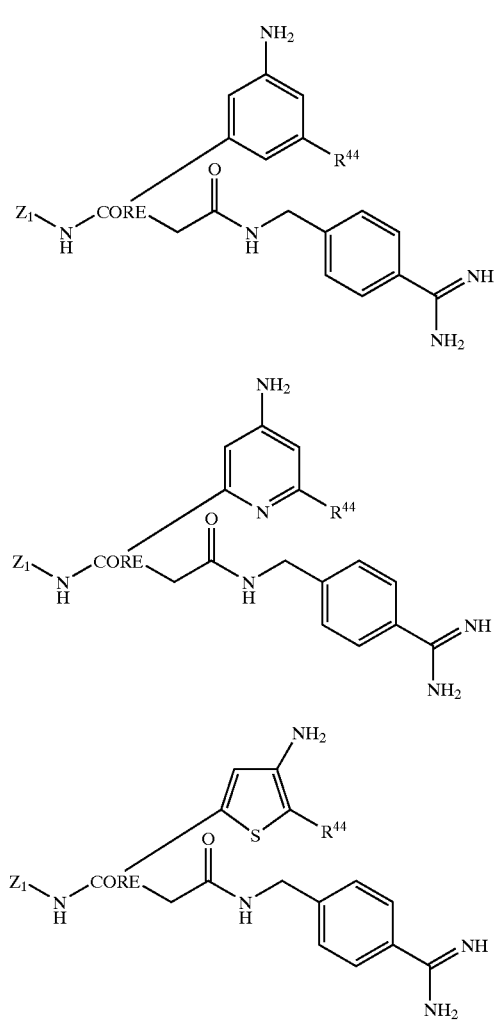 |

Following the processes described in the Schemes, Examples or elsewhere herein, the following specific compounds, as depicted in Table 2, having any one of the three structural formulas below may be prepared.

structural formula I, II, or III above and as listed in Table 2 below are specifically set forth. In addition, the cores below specifically depict the point of attachment of $Z_1$, $Z_3$ and $Z_4$ to said core.

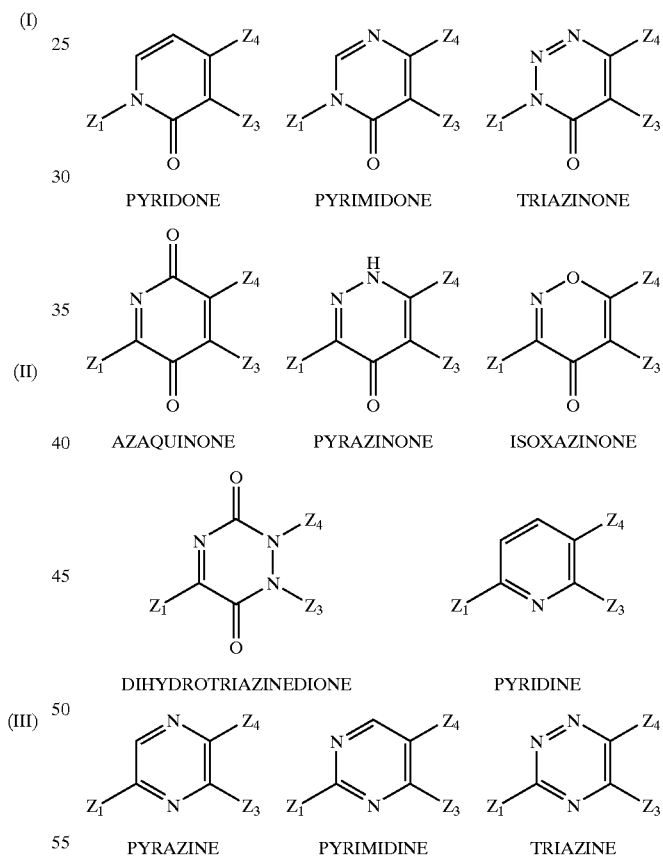

As employed herein, unless otherwise indicated, "core" refers to the 6-membered heterocyclic or aromatic ring to which $Z_1$, $Z_3$ and $Z_4$, through their respective linkages, are attached. For illustrative purposes, each core as defined by Again, for illustrative purposes, each $R^{44}$ group listed in Table 2 is set forth below

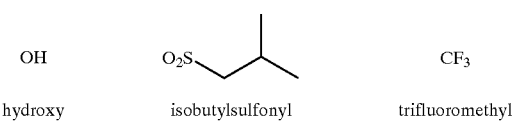

-continued

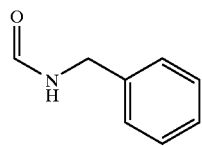
carboxamidobenzyl

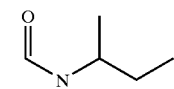
carboxamidobutyl-2-yl

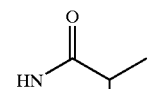
isobutyramido

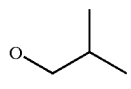
isobutoxy

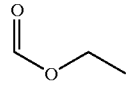
carboethoxy

CO₂H
carboxyl

NH₂
amino

TABLE 2

| Core | $Z_1$ | $R^{44}$ |
|---|---|---|
| Pyridone | methyl or ethyl or isopropyl or cyclopropyl or cyclobutyl or phenyl | hydroxy |
| Pyridone | methyl or ethyl or isopropyl or cyclopropyl or cyclobutyl or phenyl | isobutylsulfonyl |
| Pyridone | methyl or ethyl or isopropyl or cyclopropyl or cyclobutyl or phenyl | trifluoromethyl |
| Pyridone | methyl or ethyl or isopropyl or cyclopropyl or cyclobutyl or phenyl | carboxamidobenzyl |
| Pyridone | methyl or ethyl or isopropyl or cyclopropyl or cyclobutyl or phenyl | carboxamidobutyl-2-yl |
| Pyridone | methyl or ethyl or isopropyl or cyclopropyl or cyclobutyl or phenyl | isobutyramido |
| Pyridone | methyl or ethyl or isopropyl or cyclopropyl or cyclobutyl or phenyl | isobutoxy |
| Pyridone | methyl or ethyl or isopropyl or cyclopropyl or cyclobutyl or phenyl | carboethoxy |
| Pyridone | methyl or ethyl or isopropyl or cyclopropyl or cyclobutyl or phenyl | carboxyl |
| Pyridone | methyl or ethyl or isopropyl or cyclopropyl or cyclobutyl or phenyl | amino |
| Pyrimidone | methyl or ethyl or isopropyl or cyclopropyl or cyclobutyl or phenyl | hydroxy |
| Pyrimidone | methyl or ethyl or isopropyl or cyclopropyl or cyclobutyl or phenyl | isobutylsulfonyl |
| Pyrimidone | methyl or ethyl or | trifluoromethyl |

TABLE 2-continued

| Core | $Z_1$ | $R^{44}$ |
|---|---|---|
| Pyrimidone | isopropyl or cyclopropyl or cyclobutyl or phenyl methyl or ethyl or isopropyl or cyclopropyl or cyclobutyl or phenyl | carboxamidobenzyl |
| Pyrimidone | methyl or ethyl or isopropyl or cyclopropyl or cyclobutyl or phenyl | carboxamidobutyl-2-yl |
| Pyrimidone | methyl or ethyl or isopropyl or cyclopropyl or cyclobutyl or phenyl | isobutyramido |
| Pyrimidone | methyl or ethyl or isopropyl or cyclopropyl or cyclobutyl or phenyl | isobutoxy |
| Pyrimidone | methyl or ethyl or isopropyl or cyclopropyl or cyclobutyl or phenyl | carboethoxy |
| Pyrimidone | methyl or ethyl or isopropyl or cyclopropyl or cyclobutyl or phenyl | carboxyl |
| Pyrimidone | methyl or ethyl or | amino |

TABLE 2-continued

| Core | $Z_1$ | $R^{44}$ |
|---|---|---|
| Triazinone | isopropyl or cyclopropyl or cyclobutyl or phenyl methyl or ethyl or isopropyl or cyclopropyl or cyclobutyl or phenyl | hydroxy |
| Triazinone | methyl or ethyl or isopropyl or cyclopropyl or cyclobutyl or phenyl | isobutylsulfonyl |
| Triazinone | methyl or ethyl or isopropyl or cyclopropyl or cyclobutyl or phenyl | trifluoromethyl |
| Triazinone | methyl or ethyl or isopropyl or cyclopropyl or cyclobutyl or phenyl | carboxamidobenzyl |
| Triazinone | methyl or ethyl or isopropyl or cyclopropyl or cyclobutyl or phenyl | carboxamidobutyl-2-yl |
| Triazinone | methyl or ethyl or isopropyl or cyclopropyl or cyclobutyl or phenyl | isobutyramido |
| Triazinone | methyl or ethyl or | isobutoxy |

TABLE 2-continued

| Core | $Z_1$ | $R^{44}$ |
|---|---|---|
| Triazinone | isopropyl or cyclopropyl or cyclobutyl or phenyl methyl or ethyl or isopropyl or cyclopropyl or cyclobutyl or phenyl | carboethoxy |
| Triazinone | methyl or ethyl or isopropyl or cyclopropyl or cyclobutyl or phenyl | carboxyl |
| Triazinone | methyl or ethyl or isopropyl or cyclopropyl or cyclobutyl or phenyl | amino |
| Azaquinone | methyl or ethyl or isopropyl or cyclopropyl or cyclobutyl or phenyl | hydroxy |
| Azaquinone | methyl or ethyl or isopropyl or cyclopropyl or cyclobutyl or phenyl | isobutylsulfonyl |
| Azaquinone | methyl or ethyl or isopropyl or cyclopropyl or cyclobutyl or phenyl | trifluoromethyl |
| Azaquinone | methyl or ethyl or | carboxamidobenzyl |

TABLE 2-continued

| Core | $Z_1$ | $R^{44}$ |
|---|---|---|
| Azaquinone | isopropyl or cyclopropyl or cyclobutyl or phenyl methyl or ethyl or isopropyl or cyclopropyl or cyclobutyl or phenyl | carboxamidobutyl-2-yl |
| Azaquinone | methyl or ethyl or isopropyl or cyclopropyl or cyclobutyl or phenyl | isobutyramido |
| Azaquinone | methyl or ethyl or isopropyl or cyclopropyl or cyclobutyl or phenyl | isobutoxy |
| Azaquinone | methyl or ethyl or isopropyl or cyclopropyl or cyclobutyl or phenyl | carboethoxy |
| Azaquinone | methyl or ethyl or isopropyl or cyclopropyl or cyclobutyl or phenyl | carboxyl |
| Azaquinone | methyl or ethyl or isopropyl or cyclopropyl or cyclobutyl or phenyl | amino |
| Pyrazinone | methyl or ethyl or | hydroxy |

TABLE 2-continued

| Core | $Z_1$ | $R^{44}$ |
|---|---|---|
| Pyrazinone | isopropyl or cyclopropyl or cyclobutyl or phenyl methyl or ethyl or isopropyl or cyclopropyl or cyclobutyl or phenyl | isobutylsulfonyl |
| Pyrazinone | methyl or ethyl or isopropyl or cyclopropyl or cyclobutyl or phenyl | trifluoromethyl |
| Pyrazinone | methyl or ethyl or isopropyl or cyclopropyl or cyclobutyl or phenyl | carboxamidobenzyl |
| Pyrazinone | methyl or ethyl or isopropyl or cyclopropyl or cyclobutyl or phenyl | carboxamidobutyl-2-yl |
| Pyrazinone | methyl or ethyl or isopropyl or cyclopropyl or cyclobutyl or phenyl | isobutyramido |
| Pyrazinone | methyl or ethyl or isopropyl or cyclopropyl or cyclobutyl or phenyl | isobutoxy |
| Pyrazinone | methyl or ethyl or | carboethoxy |

TABLE 2-continued

| Core | $Z_1$ | $R^{44}$ |
|---|---|---|
| Pyrazinone | isopropyl or cyclopropyl or cyclobutyl or phenyl methyl or ethyl or isopropyl or cyclopropyl or cyclobutyl or phenyl | carboxyl |
| Pyrazinone | methyl or ethyl or isopropyl or cyclopropyl or cyclobutyl or phenyl | amino |
| Isoxazinone | methyl or ethyl or isopropyl or cyclopropyl or cyclobutyl or phenyl | hydroxy |
| Isoxazinone | methyl or ethyl or isopropyl or cyclopropyl or cyclobutyl or phenyl | isobutylsulfonyl |
| Isoxazinone | methyl or ethyl or isopropyl or cyclopropyl or cyclobutyl or phenyl | trifluoromethyl |
| Isoxazinone | methyl or ethyl or isopropyl or cyclopropyl or cyclobutyl or phenyl | carboxamidobenzyl |
| Isoxazinone | methyl or ethyl or | carboxamidobutyl-2-yl |

TABLE 2-continued

| Core | $Z_1$ | $R^{44}$ |
|---|---|---|
| Isoxazinone | methyl or ethyl or isopropyl or cyclopropyl or cyclobutyl or phenyl | isobutyramido |
| Isoxazinone | methyl or ethyl or isopropyl or cyclopropyl or cyclobutyl or phenyl | isobutoxy |
| Isoxazinone | methyl or ethyl or isopropyl or cyclopropyl or cyclobutyl or phenyl | carboethoxy |
| Isoxazinone | methyl or ethyl or isopropyl or cyclopropyl or cyclobutyl or phenyl | carboxyl |
| Isoxazinone | methyl or ethyl or isopropyl or cyclopropyl or cyclobutyl or phenyl | amino |
| Dihydrotriazine dione | methyl or ethyl or isopropyl or cyclopropyl or cyclobutyl or phenyl | hydroxy |
| Dihydrotriazine dione | methyl or ethyl or isopropyl or cyclopropyl or cyclobutyl or phenyl | isobutylsulfonyl |
| Dihydrotriazine dione | methyl or ethyl or isopropyl or cyclopropyl or cyclobutyl or phenyl | trifluoromethyl |
| Dihydrotriazine dione | methyl or ethyl or isopropyl or cyclopropyl or cyclobutyl or phenyl | carboxamidobenzyl |
| Dihydrotriazine dione | methyl or ethyl or isopropyl or cyclopropyl or cyclobutyl or phenyl | carboxamidobutyl-2-yl |
| Dihydrotriazine dione | methyl or ethyl or isopropyl or cyclopropyl or cyclobutyl or phenyl | isobutyramido |
| Dihydrotriazine dione | methyl or ethyl or isopropyl or cyclopropyl or cyclobutyl or phenyl | isobutoxy |
| Dihydrotriazine dione | methyl or ethyl or isopropyl or cyclopropyl or cyclobutyl or phenyl | carboethoxy |
| Dihydrotriazine dione | methyl or ethyl or isopropyl or cyclopropyl or cyclobutyl or phenyl | carboxyl |

TABLE 2-continued

| Core | $Z_1$ | $R^{44}$ |
|---|---|---|
| Dihydrotriazine dione | isopropyl or cyclopropyl or cyclobutyl or phenyl methyl or ethyl or isopropyl or cyclopropyl or cyclobutyl or phenyl | amino |
| Pyridine | methyl or ethyl or isopropyl or cyclopropyl or cyclobutyl or phenyl | hydroxy |
| Pyridine | methyl or ethyl or isopropyl or cyclopropyl or cyclobutyl or phenyl | isobutylsulfonyl |
| Pyridine | methyl or ethyl or isopropyl or cyclopropyl or cyclobutyl or phenyl | trifluoromethyl |
| Pyridine | methyl or ethyl or isopropyl or cyclopropyl or cyclobutyl or phenyl | carboxamidobenzyl |
| Pyridine | methyl or ethyl or isopropyl or cyclopropyl or cyclobutyl or phenyl | carboxamidobutyl-2-yl |
| Pyridine | methyl or ethyl or | isobutyramido |

TABLE 2-continued

| Core | $Z_1$ | $R^{44}$ |
|---|---|---|
| Pyridine | isopropyl or cyclopropyl or cyclobutyl or phenyl methyl or ethyl or isopropyl or cyclopropyl or cyclobutyl or phenyl | isobutoxy |
| Pyridine | methyl or ethyl or isopropyl or cyclopropyl or cyclobutyl or phenyl | carboethoxy |
| Pyridine | methyl or ethyl or isopropyl or cyclopropyl or cyclobutyl or phenyl | carboxyl |
| Pyridine | methyl or ethyl or isopropyl or cyclopropyl or cyclobutyl or phenyl | amino |
| Pyridine | methyl or ethyl or isopropyl or cyclopropyl or cyclobutyl or phenyl | hydroxy |
| Pyridine | methyl or ethyl or isopropyl or cyclopropyl or cyclobutyl or phenyl | isobutylsulfonyl |
| Pyridine | methyl or ethyl or | trifluoromethyl |

TABLE 2-continued

| Core | Z₁ | R⁴⁴ |
|---|---|---|
| Pyridine | isopropyl or cyclopropyl or cyclobutyl or phenyl methyl or ethyl or isopropyl or cyclopropyl or cyclobutyl or phenyl | carboxamidobenzyl |
| Pyridine | methyl or ethyl or isopropyl or cyclopropyl or cyclobutyl or phenyl | carboxamidobutyl-2-yl |
| Pyridine | methyl or ethyl or isopropyl or cyclopropyl or cyclobutyl or phenyl | isobutyramido |
| Pyridine | methyl or ethyl or isopropyl or cyclopropyl or cyclobutyl or phenyl | isobutoxy |
| Pyridine | methyl or ethyl or isopropyl or cyclopropyl or cyclobutyl or phenyl | carboethoxy |
| Pyridine | methyl or ethyl or isopropyl or cyclopropyl or cyclobutyl or phenyl | carboxyl |
| Pyridine | methyl or ethyl or | amino |

TABLE 2-continued

| Core | Z₁ | R⁴⁴ |
|---|---|---|
| Pyrazine | isopropyl or cyclopropyl or cyclobutyl or phenyl methyl or ethyl or isopropyl or cyclopropyl or cyclobutyl or phenyl | hydroxy |
| Pyrazine | methyl or ethyl or isopropyl or cyclopropyl or cyclobutyl or phenyl | isobutylsulfonyl |
| Pyrazine | methyl or ethyl or isopropyl or cyclopropyl or cyclobutyl or phenyl | trifluoromethyl |
| Pyrazine | methyl or ethyl or isopropyl or cyclopropyl or cyclobutyl or phenyl | carboxamidobenzyl |
| Pyrazine | methyl or ethyl or isopropyl or cyclopropyl or cyclobutyl or phenyl | carboxamidobutyl-2-yl |
| Pyrazine | methyl or ethyl or isopropyl or cyclopropyl or cyclobutyl or phenyl | isobutyramido |
| Pyrazine | methyl or ethyl or | isobutoxy |

TABLE 2-continued

| Core | $Z_1$ | $R^{44}$ |
|---|---|---|
| Pyrazine | isopropyl or cyclopropyl or cyclobutyl or phenyl methyl or ethyl or isopropyl or cyclopropyl or cyclobutyl or phenyl | carboethoxy |
| Pyrazine | methyl or ethyl or isopropyl or cyclopropyl or cyclobutyl or phenyl | carboxyl |
| Pyrazine | methyl or ethyl or isopropyl or cyclopropyl or cyclobutyl or phenyl | amino |
| Pyrimidine | methyl or ethyl or isopropyl or cyclopropyl or cyclobutyl or phenyl | hydroxy |
| Pyrimidine | methyl or ethyl or isopropyl or cyclopropyl or cyclobutyl or phenyl | isobutylsulfonyl |
| Pyrimidine | methyl or ethyl or isopropyl or cyclopropyl or cyclobutyl or phenyl | trifluoromethyl |
| Pyrimidine | methyl or ethyl or | carboxamidobenzyl |

TABLE 2-continued

| Core | $Z_1$ | $R^{44}$ |
|---|---|---|
| Pyrimidine | isopropyl or cyclopropyl or cyclobutyl or phenyl methyl or ethyl or isopropyl or cyclopropyl or cyclobutyl or phenyl | carboxamidobutyl-2-yl |
| Pyrimidine | methyl or ethyl or isopropyl or cyclopropyl or cyclobutyl or phenyl | isobutyramido |
| Pyrimidine | methyl or ethyl or isopropyl or cyclopropyl or cyclobutyl or phenyl | isobutoxy |
| Pyrimidine | methyl or ethyl or isopropyl or cyclopropyl or cyclobutyl or phenyl | carboethoxy |
| Pyrimidine | methyl or ethyl or isopropyl or cyclopropyl or cyclobutyl or phenyl | carboxyl |
| Pyrimidine | methyl or ethyl or isopropyl or cyclopropyl or cyclobutyl or phenyl | amino |
| Triazine | methyl or ethyl or | hydroxy |

TABLE 2-continued

| Core | $Z_1$ | $R^{44}$ |
|---|---|---|
| Triazine | isopropyl or cyclopropyl or cyclobutyl or phenyl methyl or ethyl or isopropyl or cyclopropyl or cyclobutyl or phenyl | isobutylsulfonyl |
| Triazine | methyl or ethyl or isopropyl or cyclopropyl or cyclobutyl or phenyl | trifluoromethyl |
| Triazine | methyl or ethyl or isopropyl or cyclopropyl or cyclobutyl or phenyl | carboxamidobenzyl |
| Triazine | methyl or ethyl or isopropyl or cyclopropyl or cyclobutyl or phenyl | carboxamidobutyl-2-yl |
| Triazine | methyl or ethyl or isopropyl or cyclopropyl or cyclobutyl or phenyl | isobutyramido |
| Triazine | methyl or ethyl or isopropyl or cyclopropyl or cyclobutyl or phenyl | isobutoxy |
| Triazine | methyl or ethyl or | carboethoxy |

TABLE 2-continued

| Core | $Z_1$ | $R^{44}$ |
|---|---|---|
| Triazine | isopropyl or cyclopropyl or cyclobutyl or phenyl methyl or ethyl or isopropyl or cyclopropyl or cyclobutyl or phenyl | carboxyl |
| Triazine | methyl or ethyl or isopropyl or cyclopropyl or cyclobutyl or phenyl | amino |

The generic terms described below are applicable soley for compounds based upon Formula A. Therefore, these generic terms, unless otherwise indicated or generally known in the art, should not be utilized to construe the meaning of compounds represented by general Formula I.

The terms "hydrocarbon" and "hydrocarbyl" as used herein in connection with Formula A describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein in connection with Formula A are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. Exemplary substituted hydrocarbyl moieties include, heterocyclo, alkoxyalkyl, alkenyloxyalkyl, alkynyloxyalkyl, aryloxyalkyl, hydroxyalkyl, protected hydroxyalkyl, keto, acyl, nitroalkyl, aminoalkyl, cyano, alkylthioalkyl, arylthioalkyl, ketals, acetals, amides, acids, esters and the like.

The term "heteroatom" described herein in connection with Formula A shall mean atoms other than carbon and hydrogen.

The term "physiological conditions" are those as characteristic of or approrpriate to an organisms (to a human beings) healthy or normal functioning in those organism (i.e., body) parts having its intracellular and its extracellular fluids.

Unless otherwise indicated, the alkyl groups described herein in connection with Formula A are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein in connection with Formula A are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein in connection with Formula A are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein in connection with Formula A alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein in connection with Formula A alone or as part of another group refer to chlorine, bromine, fluorine, and iodine.

The terms "heterocyclol or "heterocyclic" as used herein in connection with Formula A alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein in connection with Formula A alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "acyl," as used herein in connection with Formula A alone or as part of another group, denotes the moiety formed by removal of the hydroxyl group from the group —COOH of an organic carboxylic acid, e.g., RC(O)—, wherein R is hydrogen, $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein in connection with Formula A alone or as part of another group, denotes an acyl group as described above bonded through an oxygen linkage (—O—), e.g., RC(O)O— wherein R is as defined in connection with the term "acyl."

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention. Pharmaceutically acceptable sales of such tautomeric, geometric or stereoisomeric forms are also included within the invention.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

Some of the compounds described herein may contain one or more amide carbonyl groups or combinations thereof alone or as part of a heterocyclic ring system. Such carbonyl groups may exist in part or principally in the "keto" form and in part or principally as one or more "enol" forms of each amide group present. Compounds of the present invention having amidic carbonyl groups are meant to include both "keto" and "enol" tautomeric forms. Said amide carbonyl groups may be both oxo (C=O) and thiono (C=S) in type.

Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

The present invention also comprises a treatment and prophylaxis in anticoagulant therapy for the treatment and prevention of a variety of thrombotic conditions including coronary artery and cerebrovascular disease in a subject, comprising administering to the subject having such disorder a therapeutically-effective amount of a compound of Formula (I or A):

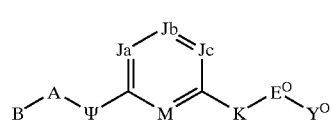

(I)

or a pharmaceutically-acceptable salt thereof.

As a further embodiment, compounds of the present invention of Formula (I or A) or a pharmaceutically-acceptable acceptable salt thereof as defined above, comprise a treatment and prophylaxis of coronary artery disease, cerebrovascular disease and other coagulation cascade related disorders in a subject, comprising administering to the subject having such disorder a therapeutically-effective amount of compounds of Formula (I or A) of the present invention or a pharmaceutically-acceptable salt thereof.

Compounds of the present invention of Formula (I or A) or a pharmaceutically-acceptable salt thereof can also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prothesis, cardiac prosthesis, and extracorporeal circulation systems.

Compounds of Formula (I or A) are capable of inhibiting activity of serine proteases related to the coagulation cascade, and thus could be used in the manufacture of a medicament, a method for the prophylactic or therapeutic treatment of diseases mediated by coagulation cascade serine proteases, such as inhibiting the formation of blood platelet aggregates, inhibiting the formation of fibrin, inhibiting thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The compounds also can be used to study the mechanism of action of coagulation cascade serine proteases to enable the design of better inhibitors and development of better assay methods. The compounds of Formula (I or A) would be also useful in prevention of cerebral vascular accident (CVA) or stroke.

Also included in the family of compounds of Formula (I or A) are the pharmaceutically-acceptable salts thereof. The term "pharmaceutically-acceptable salt" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula (I or A) may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula (I or A) include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula (I or A) by reacting, for example, the appropriate acid or base with the compound of Formula (I or A).

The present invention also comprises a pharmaceutical composition comprising a therapeutically-effective amount of a compound of Formulas (I) in association with at least one pharmaceutically-acceptable carrier, adjuvant or diluent. Pharmaceutical compositions of the present invention can comprise the active compounds of Formula (I or A) in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

The active compounds and composition may, for example, be administered orally, intravascularly, intraperitoneally, subcutaneously, intramuscularly, oculary, or topically. For treating ocular build up of fibrin, the compounds may be administered intraocularly or topically as well as orally or parenterally.

The compounds can be administered in the form of a depot injection or implant preparation which may be formulated in such a manner as to permit a sustained release of the active ingredient. The active ingredient can be compressed into pellets or small cylinders and implanted subcutaneously or intramusculary as depot injections or implants. Implants may employ inert materials such as biodegradable polymers or synthetic silicones, for example, Silastic, silicone rubber or other silicon containing polymers.

The compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or ployethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphitpathic block copolymers of hydrogels.

For oral administration, the pharmaceutical composition may be in the form of, for example, tablets, capsules (each of which includes sustained release or timed release formulations), pills, powders, granules, elixers, tinctures, suspensions, liquids including syrups, and emulsions. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of the present invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

In practicing the methods of the present invention for the treatment and prevention of a variety of thrombotic conditions including coronary artery and cerebrovascular disease, the compounds and pharmaceutical compositions of the present invention are administered alone or in combination with one another, or in combination with other therapeutics or in vivo diagnostic agents. The coagulation cascade inhibitors of the present invention can also be co-administered with suitable anti-platelet agreggation agents, including, but not limited to ticlopidine or clopidrogel, fibrinogen receptor antagonists (e.g. to treat or prevent unstable angina or to prevent reocculsion after angioplasty and restenosis), anticoagulants such as aspirin, warfarin or heparins, thrombolytic agents such as plasminogen activators or streptokinase to achieve synergistic effects in the treatment of various pathologies, lipid lowering agents including antihypercholesterolemics (e.g. HMG CoA reductase inhibitors such as mevastatin, lovastatin, simvastatin, pravastatin, and fluvastatin, HMG CoA synthatase inhibitors, etc.), anti-diabetic drugs, or other cardiovascular agents (loop diuretics, thiazide type diuretics, nitrates, aldosterone antagonistics (i.e., spironolactone and epoxymexlerenone), angiotensin converting enzyme (e.g. ACE) inhibitors, angiotensin II receptor antagonists, beta-blockers, antiarrythmics, anti-hypertension agents, and calcium channel blockers) to treat or prevent atheriosclerosis. For example, patients suffering from coronary artery disease, and patients subjected to angioplasty procedures, would benefit from coadministration of fibrinogen receptor antagonists and coagulation cascade inhibitors of the present invention. Also, coagulation cascade inhibitors could enhance the efficiency of tissue plasminogen activator-mediated thrombolytic reperfusion.

Typical doses of coagulation cascade inhibitors of the present invention with other suitable anti-platelet agents, anticoagulation agents, cardiovascular therapeutic agents, or thrombolytic agents may be the same as those doses of coagulation cascade inhibitors administered without coadministration of additional anti-platelet agents, anticoagulation agents, cardiovascular therapeutic agents, or thrombolytic agents, or may be substantially less than those doses of coagulation cascade inhibitors administered without coadministration of additional anti-platelet agents, anticoagulation agents, cardiovascular therapeutic agents, or thrombolytic agents, depending on a patient's therapeutic needs.

The present novel methods preferably employ compounds which selectively inhibit human TF-VIIA over the inhibition of both human Thrombin II and human factor Xa. Preferably, the compounds have a human TF-VIIA $IC_{50}$ of less than 0.5 mM and also have a selectivity ratio of TF-VIIA inhibition over both human Thrombin II and human factor Xa inhibition of at least 10, and more preferably at least 100. Even more preferably, the compounds have a human TF-VIIA $IC_{50}$ of less than 0.1 mM and also have a selectivity ratio of TF-VIIA inhibition over both human Thrombin II and human factor Xa inhibition of at least 1000, and most preferably at least 10,000.

All mentioned references are incorporated by reference as if here written.

Although this invention has been described with respect to specific embodiments, the details of these embodiments are not to be construed as limitations. The following examples are provided to illustrate the present invention and are not intended to limit the scope thereof. Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the schemes or the following Examples are also contemplated. Those skilled in the art will readily understand that known variations of the conditions and processes of the following preparative procedures can be used to prepare these compounds.

One skilled in the art may use these generic methods to prepare the following specific examples, which have been or may be properly characterized by $^1$H NMR, mass spectrometry, elemental composition, and similar procedures. These compounds also may be formed in vivo. The following examples contain detailed descriptions of the methods of preparation of compounds of Formula (I or A). These detailed descriptions fall within the scope and are presented for illustrative purposes only and are not intended as a restriction on the scope of the invention. All parts are by weight and temperatures are Degrees centigrade unless otherwise indicated.

The following general synthetic sequences are useful in making the present invention. Abbreviations used in the schemes and tables include: "AA" represents amino acids, "AcCN" represents acetonitrile, "AcOH" represents acetic acid, "BINAP" represents 2,2'-bis(diphenylphosphino)-1,1'-binaphthyl, "BnOH" represents benzyl alcohol, "BnCHO" represents 2-phenylethanal, "BnSO2Cl" represents benzylsulfonyl chloride, "Boc" represents tert-butyloxycarbonyl, "BOP" represents benzotriazol-1-yl-oxy-tris-(dimethylamino), "bu" represents butyl, "dba" represents dibenzylidene-acetone, "DCC" represents 1,3-dicyclohexylcarbodiimide, "DCM" represents dichloromethane or methylene chloride, "DIBAH" or "DIBAL" represents diisobutylaluminum hydride, "DMF" represents dimethylformamide, "DMSO" represents dimethylsulfoxide, "DPPA" represents diphenylphosphoryl azide", "EDC" represents 1-[3-(dimethylamino)propyl]-3-ethylcarbodiimide hydrochloride, "Ex. No." represents Example Number, "Fmoc" represents 9-fluorenylmethoxycarbonyl, "HOBt" represents hydroxybenzoltriazole", "LDA" represents lithium diisopropylamide, "MCPBA" represents meta-chloroperbenzoic acid, "MW" represents molecular weight, "NMM" represents N-methylmorpholine, "Ph" represents phenyl or aryl, "PHTH" represents a phthaloyl group, "pnZ" represents 4-nitrobenzyloxy-carbonyl, "PTC" represents a phase transfer catalyst , "py" represents pyridine, "$RNH_2$" represents a primary organic amine, "p-TsOH" represents paratoluenesulfonic acid, "TBAF" represents tetrabutylammonium fluoride, "TBTU" represents 2-(1H-benzotriozole-1-yl)-1,1,3,3-tetramethyl uronium tetrafluoroborate, "TEA" represents triethylamine, "TFA" represents trifluoroacetic acid, "THF" represents tetrahydrofuran, "TMS" represents trimethylsilyl, "TMSCN" represents trimethylsilyl cyanide, and "Cbz" or "Z" represents benzyloxycarbonyl.

GENERAL SYNTHETIC PROCEDURES AND SPECIFIC EXAMPLES

The compounds of the present invention can be synthesized, for example, according to the following procedures and Schemes given below.

A general synthetic approach to substituted pyridines is shown in Schemes 1 through 6 below. Following the procedure of Scheme 1, treatment of a 2-chloro-6-substitutedmethylpyridine with ammonia using a palladium catalyzed aryl amination procedure leads to a 2-amino-6-substitutedmethylpyridine in which the amino group is unsubstituted. Treatment of a 2-chloro-6-substitutedmethylpyridine with a nucleophilic amine using a palladium catalyzed aryl amination procedure leads to the corresponding secondary 2-aminopyridine when an primary amine is used. Alternately, the amine used could, when desired, be a secondary amine compound, a hydrazine compound, or a hydroxyamine compound. The primary 2-aminopyridine can be further reacted with a suitable aldehyde or ketone using sodium triacetoxyborohydride to prepare the corresponding substituted secondary 2-aminopyridine. Alternately, a primary or secondary 2-aminopyridne can be acylated or sulfonylated, for example, to the N-acyl derivative or N-sulfonyl derivative, respectively, using the corresponding acylating and sulfonylating agent in the presence of an equivalence of base. Following the procedure of Scheme 2, a 2-aminopyridine compound of Scheme 1 can be converted to the corresponding 2-amino-5-bromopyridine compound using bromine in acetic acid. Following the procedure of Scheme 3, a 2-amino-5-bromopyridine compound of Scheme 2 can be converted to the corresponding t-butyl 2-(6-(2-amino-5-bromopyridyl))acetate compound using di-t-butyl dicarbonate [$(Boc)_2O$] and lithium diisopropylamide in a suitable non-protic solvent such as tetrahydrofuran.

A specific synthetic process, useful in the preparation of many of the heterocyclic compounds of the present invention, is the arylation or heteroarylation of an intermediate compound characterized by having a suitable leaving group on a sp² hybridized carbon of a heterocyclic ring. In the product of the reaction, the leaving group is replace by an aryl group or a heteroaryl group. Suitable leaving groups for the reaction include chloro, bromo, iodo, methylthio, and triflates. The heterocyclic ring with the leaving group will preferably have an acetic acid group or a derivative thereof bonded to a ring atom alpha to the bromo and a substituted or unsubstituted amino group bonded to a ring atom that is both beta to the carbon having the acetic acid group and gamma to the bromo substituted ring carbon. The aryl group that is reacted at the sp² hybridized carbon is generally an aryl boronic acid or an ester of the aryl boronic acid; similarly, heteroaryl boronic acids or esters of these boronic acids can be used in the same manner as aryl boronates. The aryl and heteroaryl boronates may be substituted or unsubstituted. The aryl or heteroaryl becomes bonded to the sp² hybridized carbon at the point at which the boron was attached to the aryl or heteroaryl ring. Aryl and heteroaryl organotin compounds can also be used instead of the corresponding boronates.

Suitable reaction conditions for carrying out this transformation include:
1. Pd[P(phenyl)₃]₄, 2M Na₂CO₃, 60–75° C., dimethoxyethane (DME), H₂O, N₂;
2. Pd[P(phenyl)₃]₄, Cs₂CO₃, dioxane, 100° C.;
3. Pd[P(phenyl)₃]₄, Cu(I)-2-thiophenecarboxylate, 70–75° C., anhydrous THF, argon; and
4. Z4Sn(n-butyl)₃], Pd[P(phenyl)₃]₄, LiCl, anhydrous dioxane, 85° C., argon or N₂.

The organo-palladium (e.g., Pd[P(phenyl)₃]₄) compound is used catalytically in a ratio of 1 to 40 mole %. The carbonate base is normally used in an excess of 1.2 to 2 molar equivalents. Suitable solvents include dimethoxyethane (DME), dioxane, 1-propanol, tetrahydrofuran. The temperature of the reaction is normally in the range of from about 50 to 100° C. Cu(I)-2-thiophenecarboxylate (Cu(I)-TC) is normally used in a mole % of 110–150.

Schemes 4 through 6 and Examples 1, 3, 4, 5, 6, 7, 8, 9, 10, 11, 12, 13, and 14 show specific applications of this specific synthetic process. Procedures for preparing the intermediate heterocyclic ring compounds having a suitable leaving group on sp² hybridized carbon and useful as suitable intermediates in this specific synthetic process are given in the schemes and examples listed above.

Scheme 1
General Synthesis of Pyridines

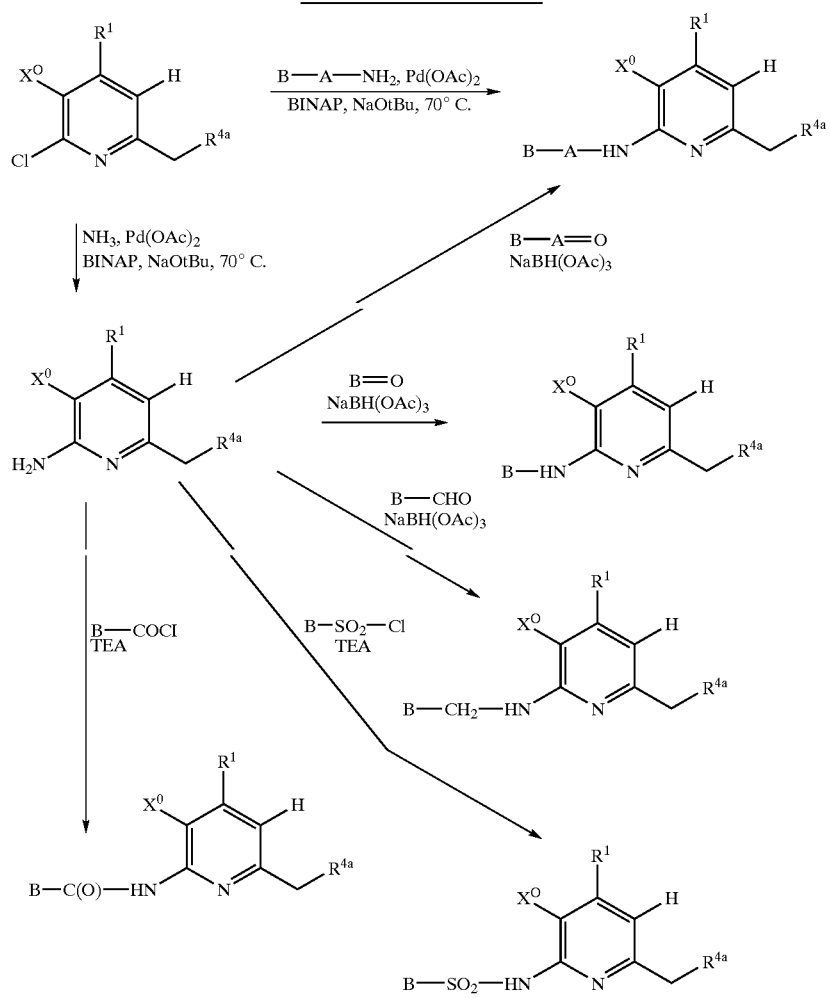

Scheme 2
General Synthesis of Pyridines
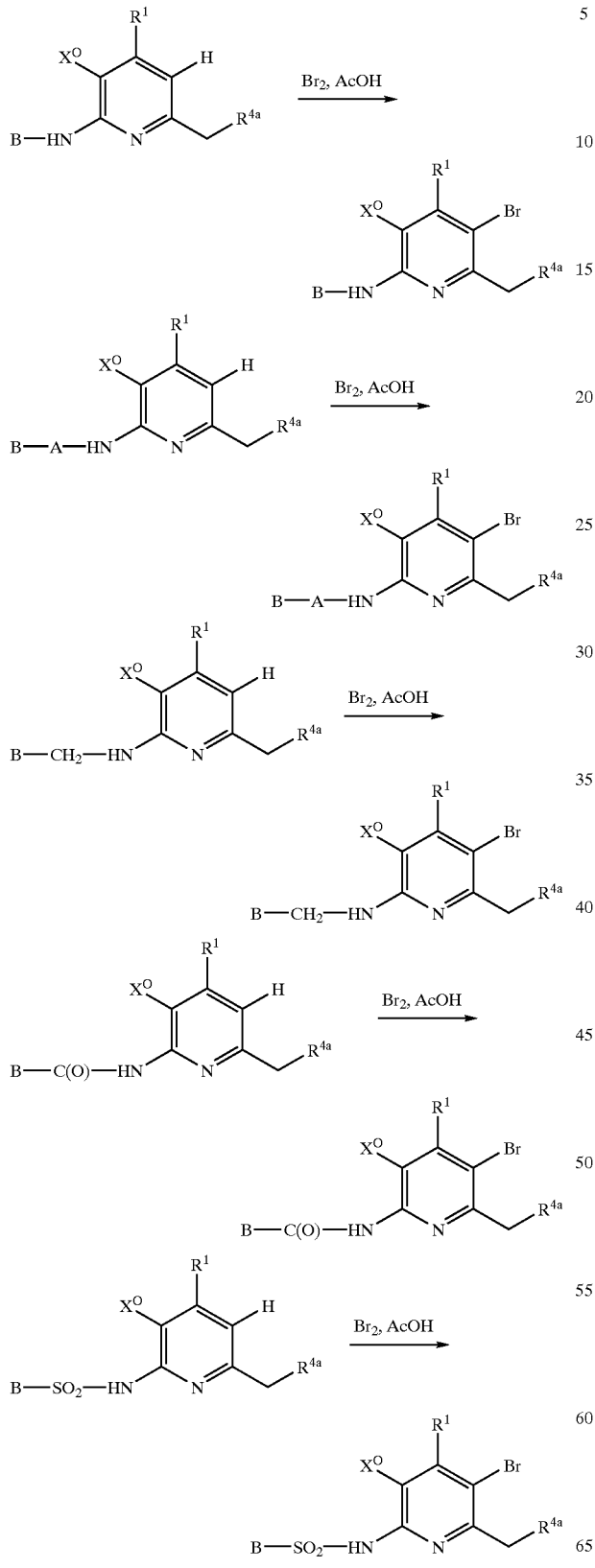
Scheme 3
General Synthesis of Pyridines
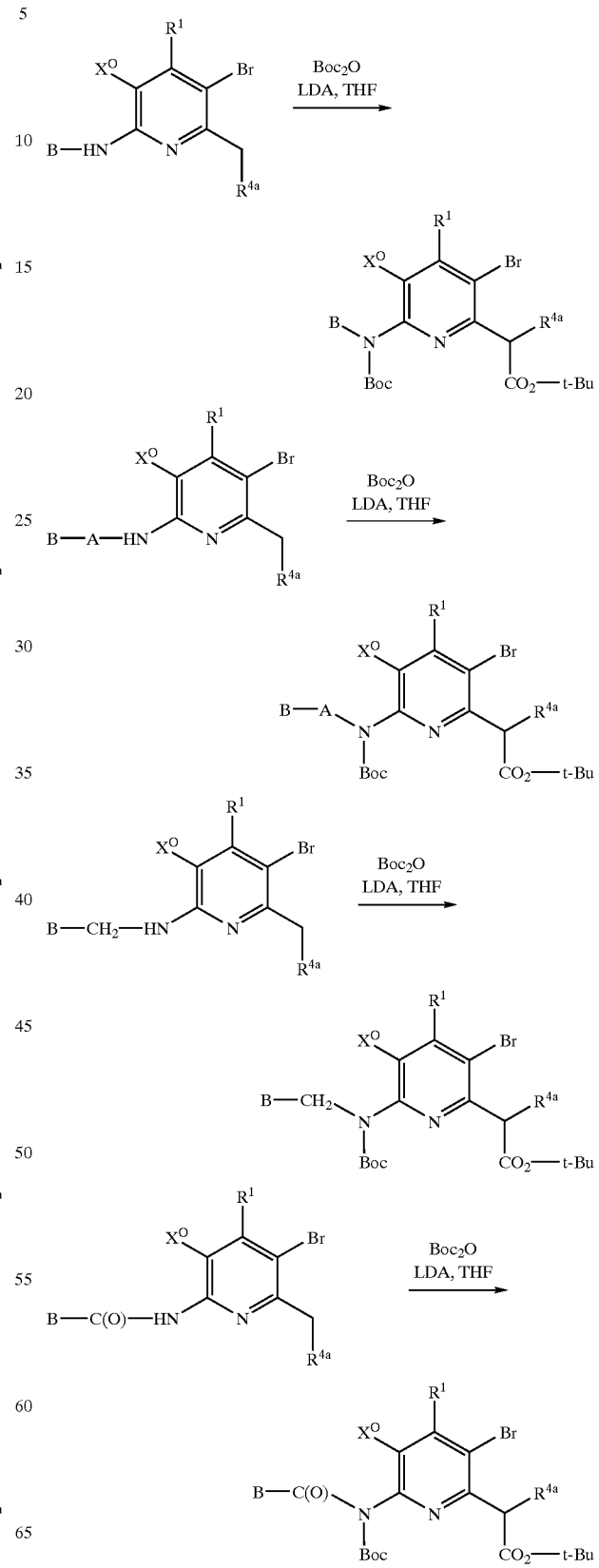

-continued

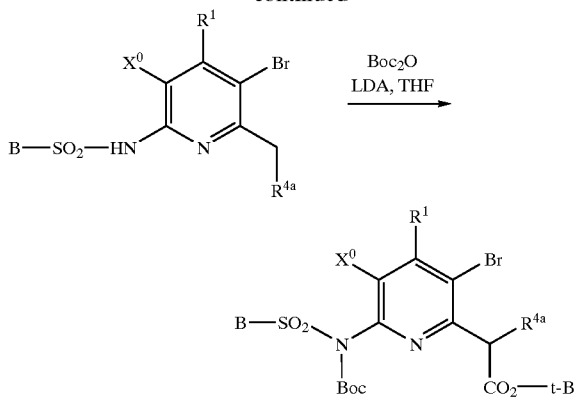

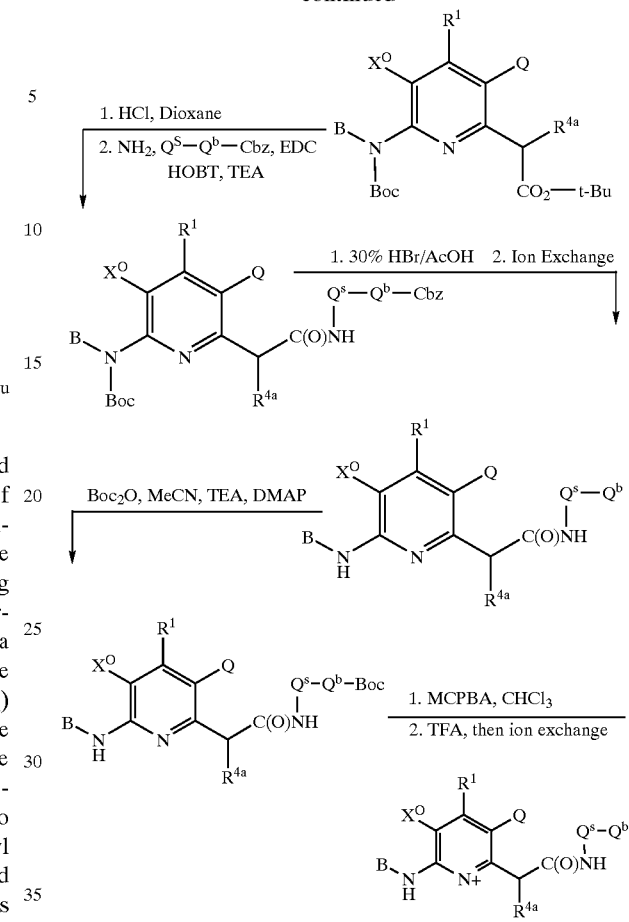

Note:
Amino, Thiol and hydroxygroups in Q and other groups will also be protected by Boc derivatives.

A t-butyl 2-(6-(2-amino-5-bromopyridyl)acetate prepared in Scheme 3 can be converted, as described in any of Schemes 4 through 6, to a compound of the present invention. A t-butyl 2-(6-(2-amino-5-bromopyridyl)acetate can be reacted with a desired arylborinate (i.e., Q-B(OH)$_2$) using palladium catalyzed coupling conditions to afford the corresponding 5-aryl t-butyl pyridylacetate. Alternately, a t-butyl 2-(6-(2-amino-5-bromopyridyl)acetate can be reacted with a desired heteroarylborinate (i.e., Q-B(OH)$_2$) using palladium catalyzed coupling conditions to afford the corresponding 5-heteroaryl t-butyl pyridylacetate. The 5-aryl or 5-heteroaryl t-butyl pyridylacetate is then deprotected with anhydrous hydrogen chloride in dioxane to remove the t-butyl ester and any other t-butoxycarbonyl protecting groups. The acid resulting can then be coupled under standard peptide coupling conditions with various amines. These amines are typically multi-functional and are introduced in a protected form. For example, a acetic acid derivative can be converted to a N-carbobenzyloxy protected pyridylacetamide. Removal of the the Cbz-group to give a desired pyridine compound of the present invention can be accomplished with hydrobromic acid in acetic acid or, alternatively, using hydrogen in the presence of a palladium on carbon catalyst. The deprotected pyridine compound can be reprotected at its amino, hydroxy and thiol groups using di-t-butyl dicarbonate. A t-butyl and t-butoxycarbonyl protected pyridinylacetamide compound can then be converted to the protected N-oxide of the pyridylacetamide using a peracid such as meta-chloroperbenzoic acid. Removal of these protecting groups in any of several ways provides the compounds. These synthetic schemes are exemplified in specific examples disclosed herein.

Scheme 4
General Synthesis of Pyridines

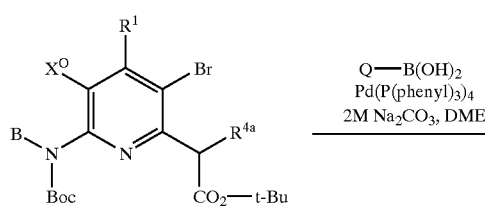

Scheme 5
General Synthesis of Pyridines

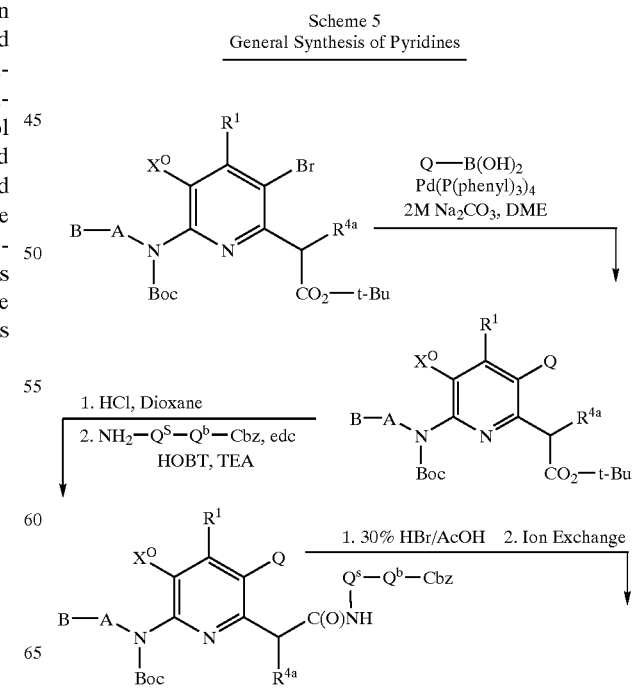

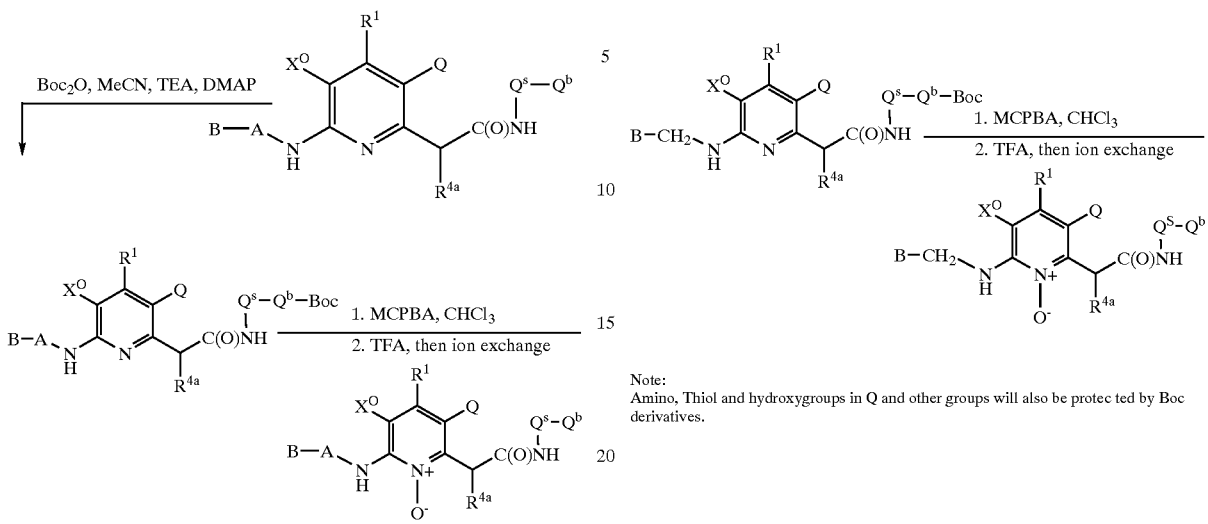
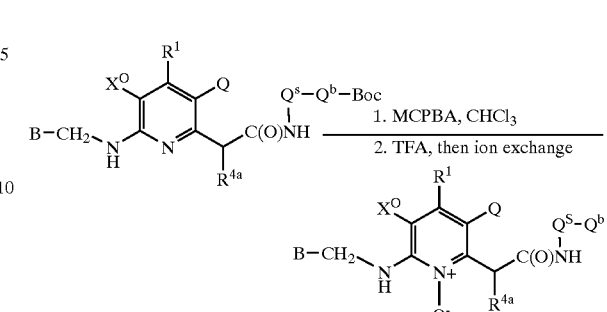
Note:
Amino, Thiol and hydroxygroups in Q and other groups will also be protected by Boc derivatives.
Scheme 6
General Synthesis of Pyridines
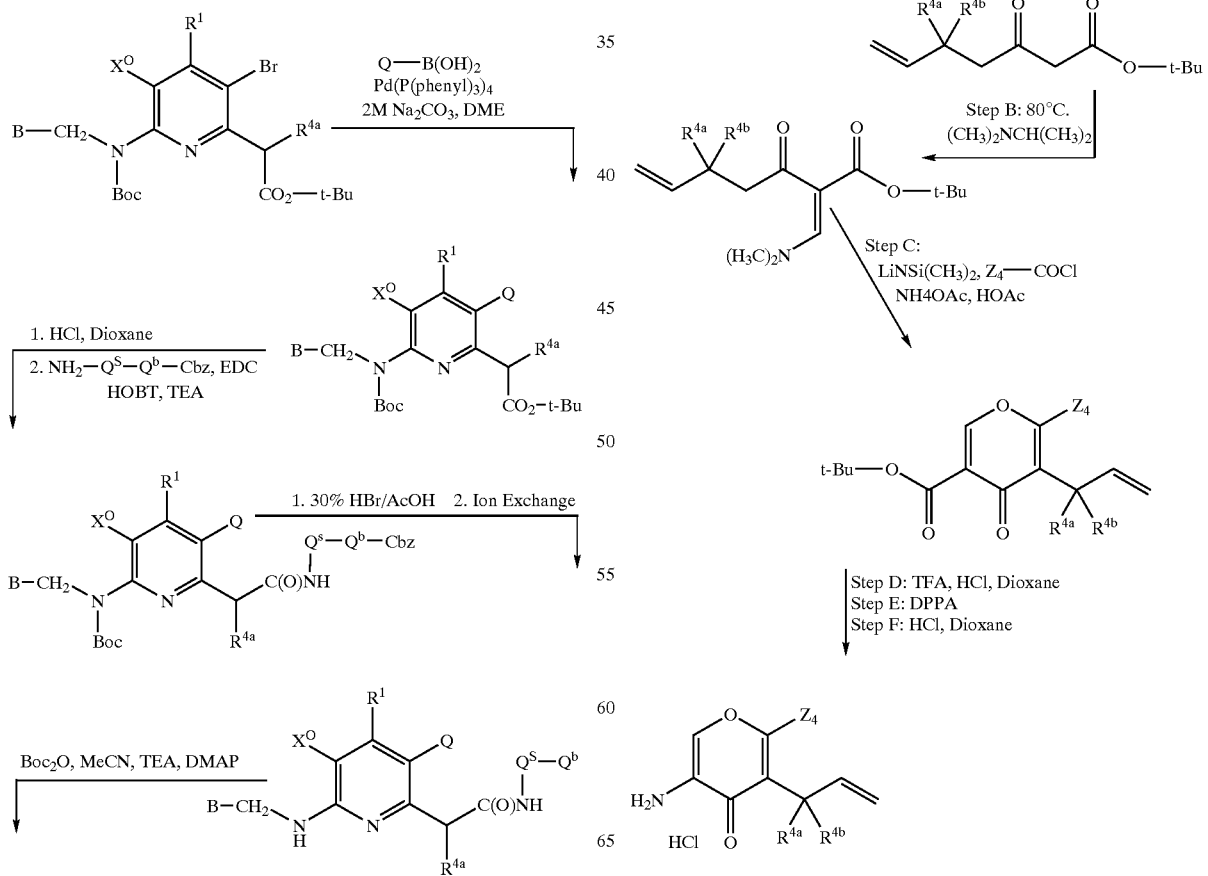
Scheme 7
Pyran
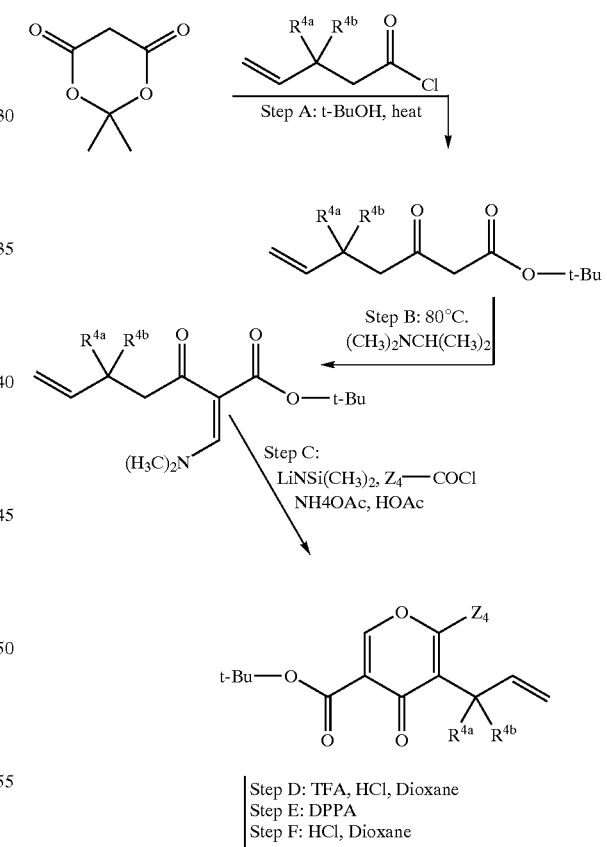

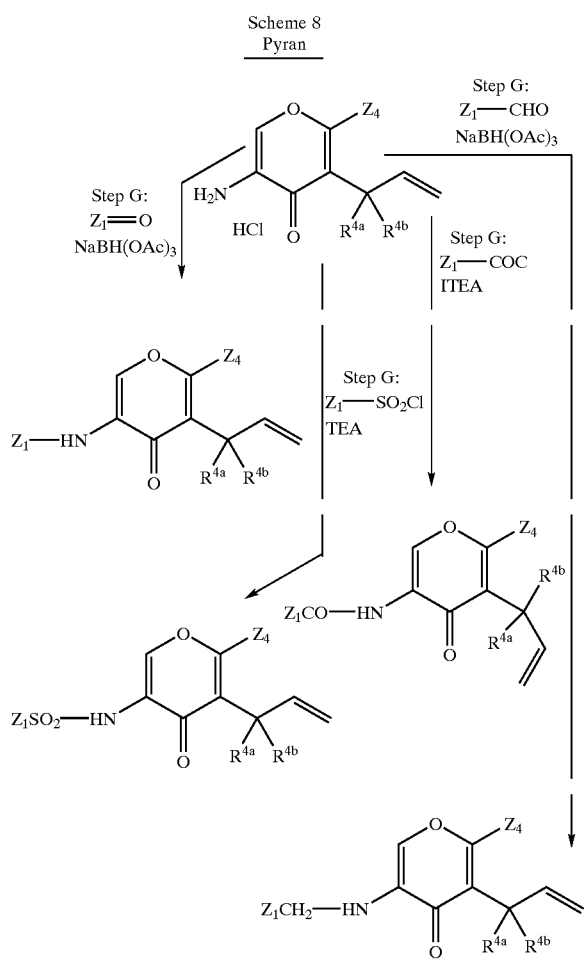
Scheme 8
Pyran
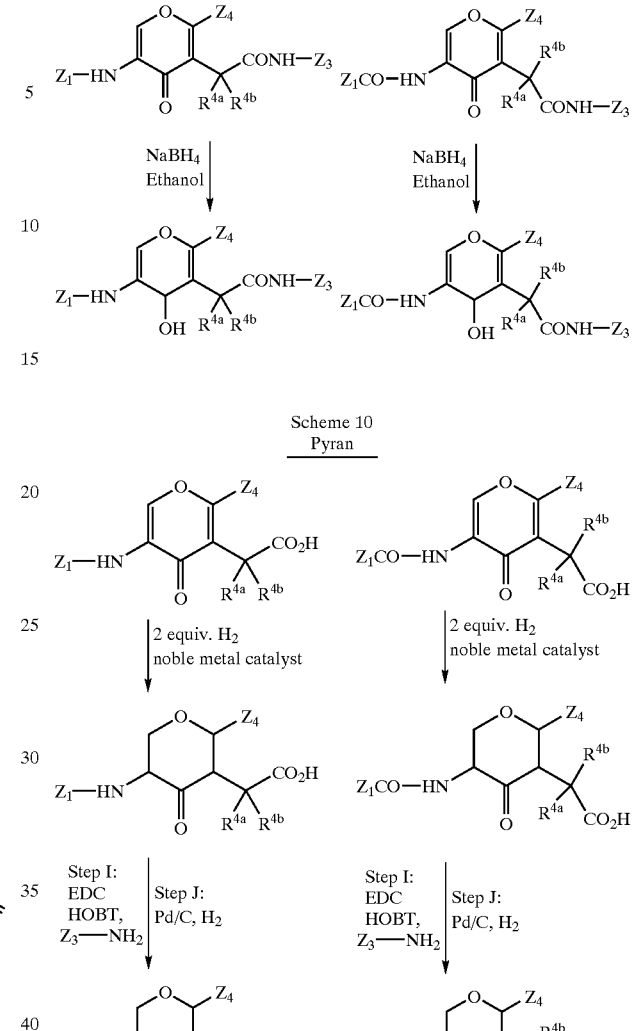
Scheme 10
Pyran
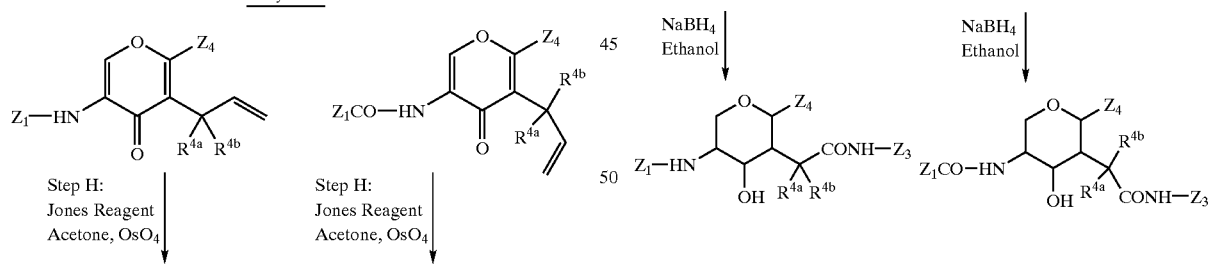
Scheme 9
Pyran
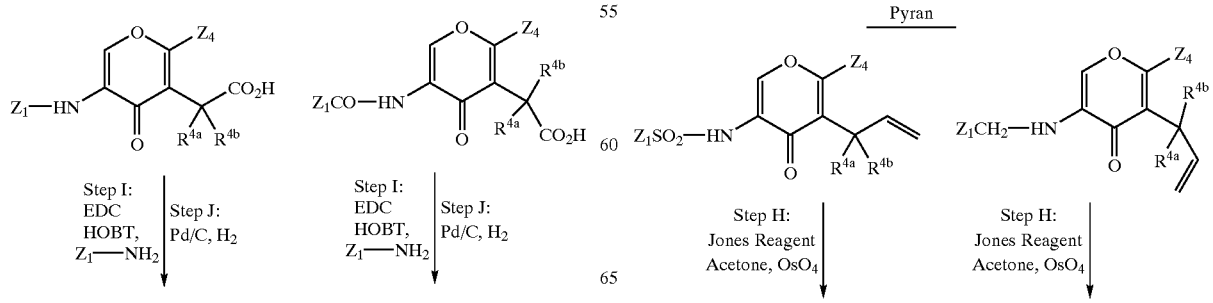
Scheme 11
Pyran

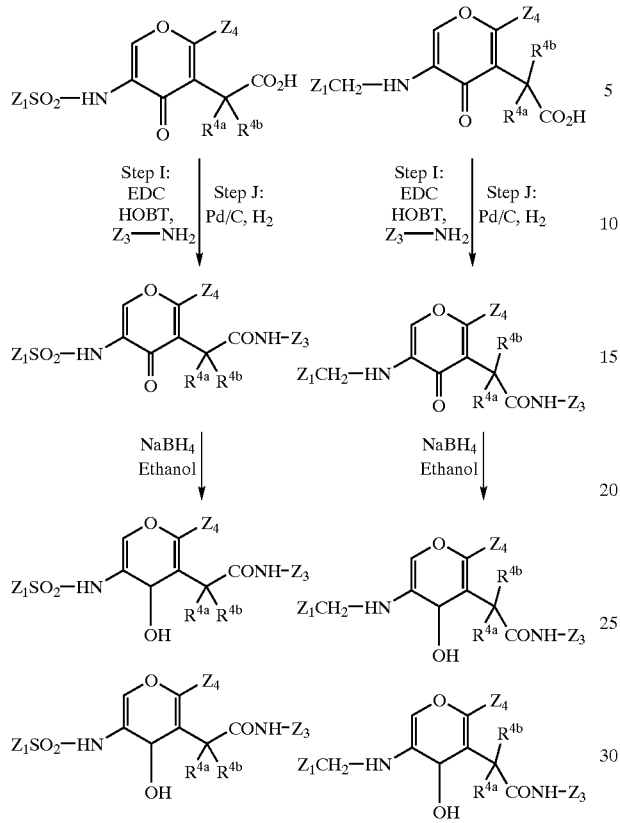

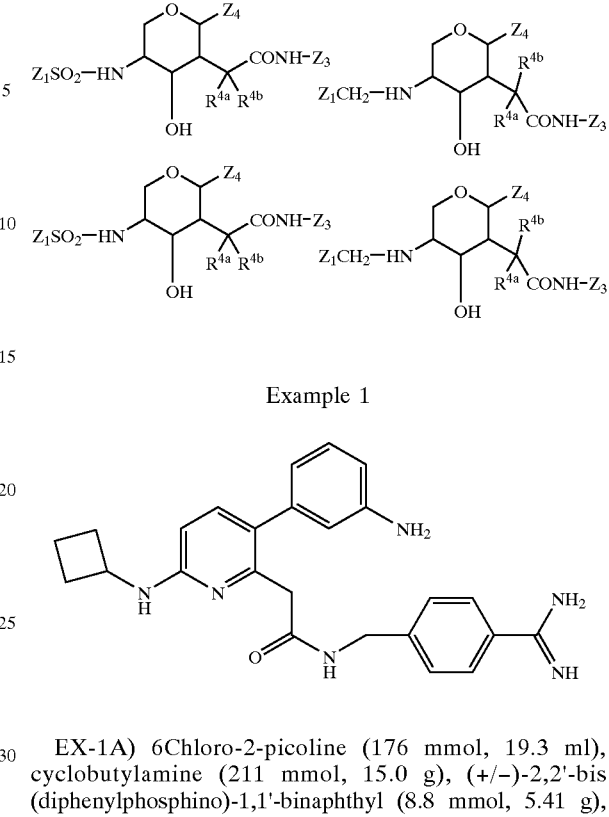

Scheme 12
Pyran

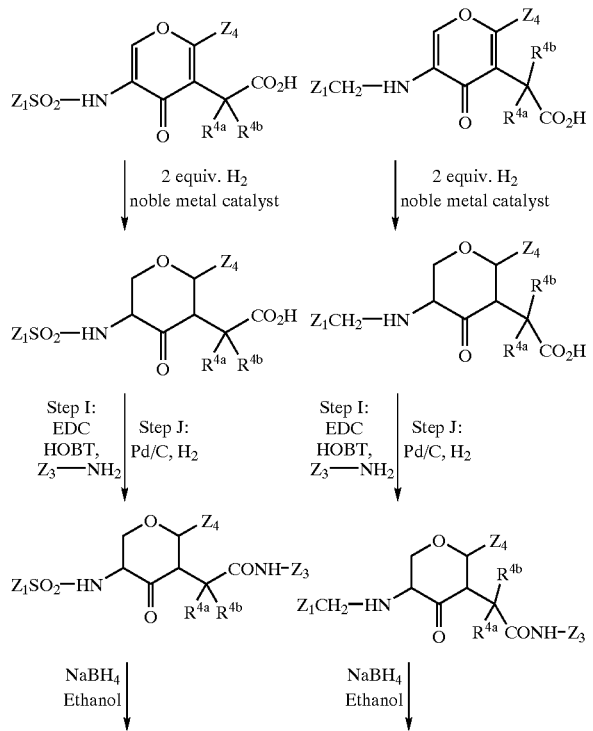

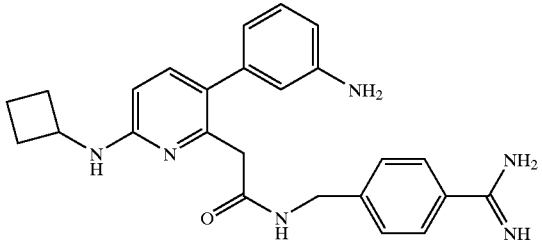

Example 1

EX-1A) 6Chloro-2-picoline (176 mmol, 19.3 ml), cyclobutylamine (211 mmol, 15.0 g), (+/−)-2,2'-bis(diphenylphosphino)-1,1'-binaphthyl (8.8 mmol, 5.41 g), palladium acetate (8.9 mmol, 2.0 g), sodium tert-butoxide (250 mmol, 24.0 g), and toluene (1500 ml) were added to an oven-dried, nitrogen purged flask and the reaction heated to 70° C. for five hours. The cooled reaction mixture was diluted with diethyl ether (700 ml), washed three times with saturated brine (400 ml), dried over $MgSO_4$, and concentrated in vacuo. Purification by silica gel chromatography (20% ethyl acetate/hexane) yielded 17.9 g (62% yield) of EX-1A as a red oil. MS (ES, m/z) 163 (M+H).

EX-1B) To a stirred solution of EX-1A (110 mmol, 17.9 g) in acetic acid (50 ml) was added a solution of bromine (110 mmol, 5.7 ml) in acetic acid (5 ml) over 30 minutes while maintaining the temperature at ~20° C. with cooling in a water bath. After 1.5 hours the reaction was mixed with water (50 ml) and neutralized with 50% sodium hydroxide while cooling in a ice bath. The mixture was extracted with three time dichloromethane (50 ml). The combined dichloromethane fractions were dried over $MgSO_4$ and concentrated in vacuo to give 25.8 g of yellow oil. Purification by silica gel chromatography (5% dichloromethane/hexane to 10% ethyl acetate/hexane) yielded 18.04 g (67% yield) of EX-1B as a pale yellow oil. MS(ES, m/z) 243 (M+H).

EX-1C) To a stirred solution of EX-1B (30 mmol, 7.25 g) and di-tert-butyldicarbonate (182 mmol, 39.75g) in tetrahydrofuran (200 ml) under nitrogen, cooled to −45° C. was added lithium diisopropylamide monotetrahydrofuran (1.5M solution in cyclohexane, 33 mmol, 22 ml). After 1 hour, additional lithium diisopropylamide monotetrahydrofuran (1.5M solution in cyclohexane, 30 mmol, 20 ml) was added and stirring continued for 30 minutes. The reaction was quenched with saturated ammonium chloride, concentrated in vacuo, mixed with ethyl acetate (200 ml), washed two times with water (50 ml) and saturated brine (50 ml), dried over $MgSO_4$, and concentrated in vacuo. Purification by silica gel chromatography (5% ethyl acetate/hexane)

yielded 3.1 g (23% yield) of EX-1C as a pale yellow oil. MS(ES, m/z) 443 (M+H).

EX-1D) To a stirred mixture of EX-1C(4.5 mmol, 2.0 g), 3-aminobenzene boronic acid monohydrate (6.9 mmol, 1.07 g), and tetrakis(triphenylphosphine)palladium(O) (2.3 mmol, 2.6 g) in ethylene glycol dimethyl ether (80 ml) under nitrogen was added 2M sodium carbonate (60 mmol, 30 ml). The reaction was heated to 60 °C for 7 hours. The cooled reaction mixture was combined with ethyl acetate (200 ml), washed with water (50 ml) and two times with saturated brine (50 ml), dried over $MgSO_4$, and concentrated in vacuo. Purification by silica gel chromatography (30–40% ethyl acetate/hexane) yielded 0.65 g (32% yield) of EX-1D as a yellow oil. MS(ES, m/z) 454 (M+H).

EX-1E) EX-1D (1.4 mmol, 0.64 g) was mixed with 4N hydrogen chloride in dioxane at ambient temperature for 48 hours. The reaction was concentrated in vacuo. The residue (0.5 g), 1-hydroxybenzotriazole hydrate (1.8 mmol, 0.24 g), and 4-(N-benzyloxycarbonylamidino)benzylamine (2.0 mmol, 0.71 g) were stirred under nitrogen in dimethylformamide with cooling in an ice bath. 1-(3-Dimethylaminopropyl)3-ethylcarbodiimide hydrochloride (1.8 mmol, 0.34 g) and triethylamine (7.0 mmol, 0.97 ml) were added, and the reaction was slowly allowed to warm to ambient temperature and stirred for 23 hours. The reaction was cooled in an ice bath and additional 1-(3-dimethylaminopropyl)-3-ethylcarbodiimide hydrochloride (0.5 mmol, 0.1 g) and triethylamine (2.4 mmol, 0.33 ml) were added. The reaction was slowly allowed to warm to ambient temperature and stir for 3 hours. The reaction mixture was combined with ethyl acetate (75 ml), washed three times with water (25 ml) and saturated brine (25 ml), dried over $MgSO_4$, and concentrated in vacuo. Purification by silica gel chromatography (ethyl acetate) yielded 0.28 g (35% yield) of EX-1E as a tan solid. MS (ES, m/z) 563 (M+H).

EX-1E (0.48 mmol, 0.27 g) was stirred with hydrogen bromide, 30 wt. % solution in acetic acid (15 ml), in a nitrogen flushed capped vial at ambient temperature for 19 hours. Diethyl ether was added, and the resulting precipitate collected and dried to give 0.28 g of pink solid. Conversion to the hydrogen chloride salt was accomplished by elution (deionized water) through a column of AG 2-X8 ion-exchange resin (chloride form) to yield 0.20 g (73% yield) of the product as a light tan solid. HRMS calc'd for $C_{25}H_{29}N_6O$ (M+H) : 429.2403. Found: 429.2390. Anal. Calc'd for $C_{25}H_{28}N_6O+3.0$ HCl, 1.5 $H_2O$: C, 53.15; H, 6.07; N, 14.88; Cl, 18.83. Found: C, 53.09; H, 5.97; N, 14.61; Cl, 18.97.

Example 2

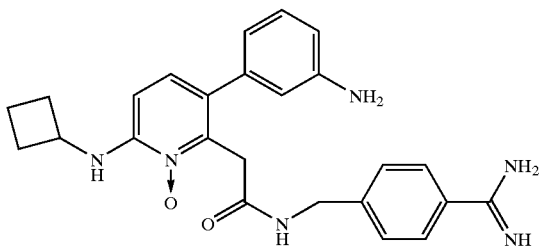

EX-2A) To a stirred suspension of the product of Example 1 (0.111 mmol, 62.8 mg) in acetonitrile (10 ml) was added triethylamine (0.359 mmol, 50 ml), di-tert-butyldicarbonate (0.261 mmol, 60 ml) and 4-dimethylaminopyridine (0.016 mmol, 2 mg). The reaction was stirred at ambient temperature for 15 hours. The reaction was concentrated in vacuo, mixed with ethyl acetate (10 ml), washed with two times water (5 ml) and saturated brine (5 ml), dried over $MgSO_4$, concentrated in vacuo and the EX-2A used without further purification.

The EX-2A residue was dissolved in chloroform (10 ml), cooled in an ice bath and 3-chloroperoxybenzoic acid 64% (0.122 mmol, 33 mg) added and stirring continued for 1 hour. Trifluoroacetic acid (10 ml) was added and stirring continued in an ice bath for 1 hour. The reaction was concentrated in vacuo. Purification by reverse phase HPLC (2–12% acetonitrile/water) and lyophilization gave the product as an off-white solid. Conversion to the hydrogen chloride salt was accomplished by elution (deionized water) through a column of AG 2-X8 ion-exchange resin (chloride form) to yield 31 mg (48% yield) of the product as an off-white solid. HRMS calc'd for $C_{25}H_{29}N_6O_2$ (M+H): 445.2352. Found: 445.2359. Anal. Calc'd for $C_{25}H_{28}N_6O_2+$ 2.35 HCl, 2.9 $H_2O$: C, 51.54; H, 6.25; N, 14.42; Cl, 14.3. Found: C, 51.55; H, 5.95; N, 14.32; Cl, 14.29.

Example 3

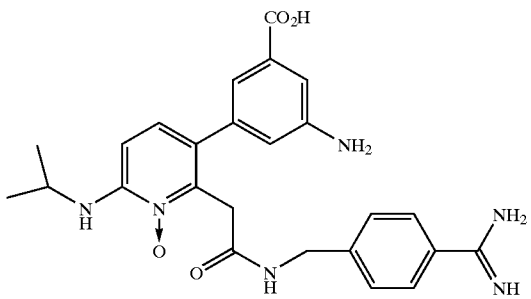

Following the procedures described in Example 1, (3-Amino-5-methoxycarbonylphenyl)boronic acid (200 mg, 0.87mmol) in MeCN (3 ml) was added to $Boc_2O$ (0.87 ml, 0.87 mmol) and $Et_3N$ (0.26 ml, 1.8 mmol) at room temperature. The reaction mixture was kept stirring at room temperature for 4 hr. Then HCl solution (pH=4, 4ml) was added, the mixture was extracted with EtOAc (3×5 ml). The combined EtOAc was then dried and concentrated to yield 260mg oil EX-3A. (Yield: 100%.) MS(ES, m/z) 296.12 (M+H).

Following procedure the procedure of Example 1 for the coupling of the a boronic acid in amino protected form EX-3A was reacted with 2-[2-[N-[[4-(N-t-butoxycarbonylamino)iminomethylphenyl]methyl]-3-bromo-6-isopropylamino-pyridinyl]]acetamide to give EX-3B without purification. MS(ES, m/z) 675.34 (M+H).

EX-3B (200 mg) in $MeOH/H_2O$ (2 ml/0.4 ml) was mixed with 2N LiOH (0.37 ml, 0.74 mmol) at 0C. The mixture was kept stirring at room temperature for 3 hr. Then additional 2N LiOH (0.2 ml, 0.4 mmol) was added to the mixture, and the mixture was stirred at room temperature for another 2 hr. Then the solution was acidified to pH 7 by 1N HCl and extracted with EtOAc (3 times with 5 ml). Solid EX-3C (80 mg) which contained the product (LC/MS checked) was also collected by filtering the solution. Combined EtOAc extracts were then dried with $Na_2SO_4$ and concentrated to yield 15mg crude solid EX-3C which was used for next reaction. MS(ES, m/z) 661.33 (M+H).

EX-3C was converted using similar procedures to those described in Example 2 to give a 19% yield of the product: HRMS calc'd for $C_{25}H_{28}N_6O_4$ (M+H): 477.2250. Found: 477.2248.

Example 4

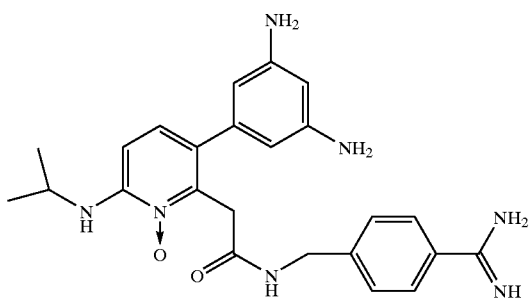

Using procedures similar to those described in Examples 1 and 3, (3-amino-5-methoxycarbonylphenyl)boronic acid was coupled with 2-[2-[N-[[4-(N-t-butoxycarbonylamino)iminomethylphenyl]methyl]-3-bromo-6-isopropylaminopyridinyl]]acetamide afford 2-[2-[N-[[4-(N-t-butoxycarbonylamino)iminomethyl-phenyl]methyl]-3-[3-amino-5-carbomethoxyphenyl)-6-isopropylaminopyridinyl]]-acetamide (EX-4A) in 70% yield: MS(ES, m/z) 575.29 (M+H).

Using procedures similar to those of Example 2, the N-oxide product was formed in 17% yield from EX-4A: HRMS calc'd for $C_{26}H_{30}N_6O_4$ (M+H) : 491.2407. Found: 491.2426. Anal. Calc'd for $C_{26}H_{30}N_6O_4$+2.15TFA, 1.5$H_2O$: C, 47.71; H, 4.64; N, 11.01. Found: C, 47.76; H, 4.71; N. 10.96.

Example 5

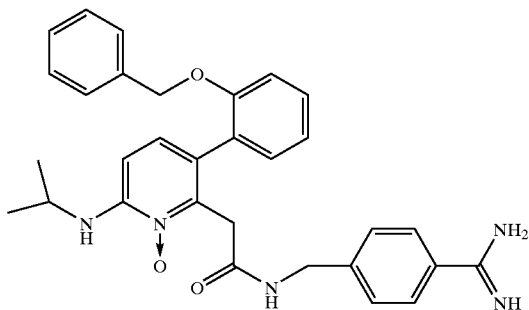

Using procedures similar to those described in Example 1, isopropylamine was used instead of cyclobutylamine and reacted with 2-chloro-6-methylpyridine to give EX-5A in an 83% yield: MS(ES, m/z) 151.12 (M+H).

Similar procedures were used to convert used instead of cyclobutylamine and reacted with 2-chloro-6-methylpyridine to give EX-5A to used instead of cyclobutylamine and reacted with 2-chloro-6-methylpyridine to give the bromopyridine EX-5B in a yield of 55%. MS(ES, P/z) 229.05 (M+H).

EX-5B (12 g, 0.06 mol) in THF (100 ml) was cooled to −45° C. and LDA (60 ml, 0.09 mol) was added. After 10 min, Boc$_2$O (12 g, 0.06 ml) in THF (50 ml) was added to the solution. After 3 hr, the solution was mixed with water (200 ml), concentrated to 200 ml, extracted with $CH_2Cl_2$ (3×150 ml). The combined $CH_2Cl_2$ extracts were then dried, concentrated and purified to yield 12g of oil EX-5C. MS (ES, m/z) 329.10 (M+H).

EX-5C (5 g, 15 mmol) in THF (50 ml) was cooled to −78° C. and LDA (15 ml, 23 mmol) was added. After 30 min, dry ice (3 g) was added to the solution. After 3 hr, the solution was added with water (200 ml), concentrated to 200 ml, basified to pH 9 with saturated aqueous $Na_2CO_3$, washed with ether (3×50 ml), then acidified to pH 5 with 1N HCl, and extracted with $CH_2Cl_2$ (3×150 ml). The combined $CH_2Cl2$ was then dried over $Na_2SO_4$ and concentrated to yield 4.5 g of white solid EX-5D. MS(ES, m/z) 373.09 (M+H).

To a stirred solution of EX-5D (6.4 mmol, 2.4 g,), 1-hydroxybenzotriazole hydrate (9.1 mmol, 1.23 g,), 4-(N-benzyloxycarbonylamidino) benzylamine hydrochloride (8.7 mmol, 3.1 g), and triethylamine (14.3 mmol, 2.0 ml,) in dimethylformamide (100 ml) under nitrogen cooled in an ice bath was added 1-(3-dimethylaminopropyl)-3-ethylcarbodiimide hydrochloride (9.1 mmol, 1.74 g) and triethylamine (57.4 mmol, 8 ml). The reaction was stirred in the bath and allowed to slowly warm to ambient temperature for 18 hours. The reaction was diluted with water (300 ml) and extracted with ethyl acetate (3×125 ml). The combined organic fractions were washed with dilute hydrochloric acid (3×50 ml), saturated sodium bicarbonate solution (2×50 ml), and brine (50 ml). The combined acid washes were neutralized with saturated sodium bicarbonate solution and extracted with ethyl acetate (2×50 ml). These new organic fractions were brine washed, combined with previous organic washes, dried over magnesium sulfate, filtered and concentrated in vacuo. Purification by silica gel chromatography (50–65% ethyl acetate/hexane) yielded 2.88 g (70% yield) of EX-5E as an off-white foam. MS(ES, m/z), 638:640 (M+H).

A solution of EX-5E (14.2 mmol, 9.09 g) in hydrobromic acid (33% in acetic acid, 150 ml) was stirred at ambient temperature for 18 hours. The reaction was diluted with diethyl ether to give a tacky precipitate. The solution was decanted, and the residue was rinsed with diethyl ether. The residue was dissolved in water (200 ml), neutralized with saturated sodium bicarbonate solution, and the pH adjusted to 12 with sodium carbonate (2N). The resulting precipitate was collected by vacuum filtration, water washed, and dried in vacuo. The filtrate was extracted with dichloromethane (3×100 ml). The combined organic fractions were washed with brine (50 ml), dried over magnesium sulfate, filtered, and concentrated in vacuo. The combined residues yielded 5.48 g (95% yield) of EX-5F as a tan solid. MS(ES, m/z), 404:406 (M+H).

To a stirred suspension of EX-5F (13.5 mmol, 4.47 g), in acetonitrile (500 ml) was added di-tert-butyldicarbonate (14.3 mmol, 3.55 g), triethylamine (13.5 mmol, 1.88 ml), and 4-dimethylaminopyridine (1.6 mmol, 0.2 g). The reaction was stirred at ambient temperature for 64 hours. The reaction was concentrated in vacuo. The residue was diluted with ethyl acetate (300 ml), washed with water (2×100 ml), brine (100 ml), dried over magnesium sulfate, filtered, and concentrated in vacuo. The residue was crystallized form ethyl acetate/hexane to yield 3.0 g (44% yield) of EX-5G as an off-white solid. MS(ES, m/z), 504:506 (M+H).

To a stirred solution of EX-5G (5.6 mmol, 2.8 g) in dichloromethane (300 ml) and chloroform (100 ml) was added 3-chloroperoxybenzoic acid (64%, 6.3 mmol, 1.71 g). Stirring was continued at ambient temperature for 30 minutes. The reaction was concentrated in vacuo, and the residue mixed with ethyl acetate (300 ml) and dichloromethane (50 ml), washed with 2M sodium carbonate (3×50 ml), and brine (50 ml). The combined aqueous fractions were extracted with chloroform (2×25 ml), and the chloroform fractions washed with brine. The combined organic fractions were cooled, and the resulting solid collected by vacuum filtration to yield 2.19 g (73% yield) of EX-5H as an orange solid. MS(ES, m/z), 520:522 (M+H). Concentration of the filtrate gave an additional 0.66 g (22%).

A solution of EX-5H (0.096 mmol, 50 mg) in dichloromethane (1 ml) and trifluoroacetic acid (1 ml) was stirred at ambient temperature for 30 minutes. The reaction was concentrated under a stream of nitrogen and the residue was crystallized from acetonitrile/diethyl ether to yield 28 mg (69% yield) of EX-5I as a pale orange solid. MS(ES, m/z), 420:422 (M+H). HRMS calc'd for $C_{18}H_{23}N_5O_2Br$ (M+H): 420.1035. Found: 420.1046. Anal. Calc'd for $C_{18}H_{22}N_5O_2Br$ +1.95 TFA, 0.15.5 $H_2O$: C, 40.48; H, 3.70; N, 10.70. Found: C, 40.75; H, 3.75; N, 10.48.

A mixture of EX-5I (0.144 mmol, 75 mg), (2-benzyloxyohenyl) boronic acid (0.43 mmol, 99 mg), cesium carbonate (0.43 mmol, 140 mg), tetrakis-triphenylphosphine palladium (0) (0.043 mmol, 50 mg), ethylene glycol dimethyl ether (4 ml) and water (0.5 ml) under nitrogen was heated at 65° C. for 16 hours. The reaction was concentrated under a nitrogen stream. The residue was mixed with ethyl acetate (4 ml), washed with water (2 ml) and brine (2 ml), and concentrated in vacuo. A solution of the residue in chloroform (2 ml) and trifluoro-acetic acid (2 ml) was stirred at ambient temperature for 30 minutes. The reaction was concentrated under a nitrogen stream and purification by reverse phase HPLC (30–70% acetonitrile/water) followed by lyophilization yielded the product as an off-white solid. HRMS calc'd for $C_{31}H_{34}N_5O_3$ (M+H): 524.2662. Found: 524.2678. Anal. Calc'd for $C_{31}H_{34}N_5O_3$+2.2 TFA, 0.6 $H_2O$: C, 54.14; H, 4.67; N, 8.91. Found: C, 54.10; H, 4.58; N, 9.07.

Example 6

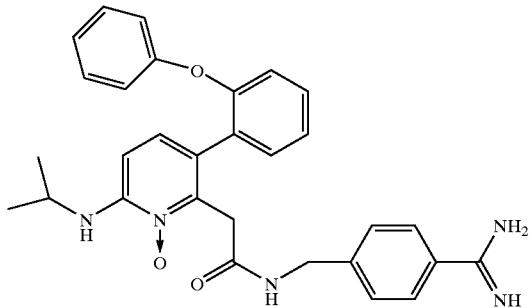

Using procedures similar to those described in Example 5 and substituting (2-phenoxyphenyl)boronic acid for (2-benzyloxyphenyl)boronic acid, the product was obtained as an off-white solid. HRMS calc d for $C_{30}H_{32}N_5O_3$ (M+H): 510.2505. Found: 510.2508.

Example 7

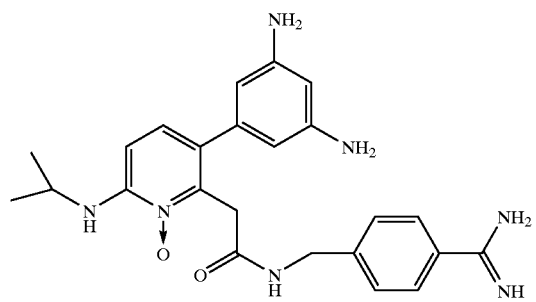

A 250 mL round bottom flask was charged with iodo-3,5-dinitrobenzene (51.4 mmol, 15.1 g), bis(pinacolato)diboron (61.6 mmol, 15.7 g), dichloro[1,1'-bis(diphenylphosphino)-ferrocene]palladium(II) dichloromethane adduct (10 mol %, 3.80 g), and potassium acetate (154 mmol, 15.1 g). The mixture was pump/purged (vacuum/argon) for 3 cycles, and DMF (200 mL) was added via cannula transfer. The reaction was stirred at 75° C. overnight. At this time, the reaction mixture was cooled and concentrated. The dark black mixture was recrystallized from acetonitrile to afford 10.7 g (71% yield) of pure boronate ester EX-7A as a tan solid: $^1$H NMR (CDC$_{13}$) δ9.06 (t, J=1.5 Hz, 1 H), 8.88 (d, J=1.5 Hz, 2 H), 1.35 (s, 12 H); LC-LRMS (ESI, negative ion mode) (M−H)⁻=211 (for boronic acid hydrolysis product).

A mixture of 3,5-dinitrophenylboronic acid, pinacol ester EX-7A (0.85 mmol, 0.25 g) and palladium on carbon (10% dry basis, wet, 0.25 g) in ethanol (75 ml) and water (1 ml) was shaken under hydrogen (40 psi) for 30 minutes. The reaction was filtered and concentrated in vacuo to yield 0.20 g (100% yield) of EX-7B as a light gray solid. MS(ES, m/z), 235 (M+H). $^1$HNMR (CDCl$_3$) δ1.22 (s, 12H), 3.88 (s, 4H), 6.16 (S, 1H), 6.48 (s, 2H).

A mixture of EX-5H (0.29 mmol, 150 mg), EX-7B (0.43 mmol, 101 mg), cesium carbonate (1.16 mmol, 377 mg), tetrakis-triphenylphosphine palladium (0) (0.058 mmol, 67 mg), ethylene glycol dimethyl ether (6 ml) and water (0.75 ml) under nitrogen was heated at 65° C. for 16 hours and at 75° C. for 20 hours. The reaction was concentrated under a nitrogen stream. The residue was eluted through a 5 ml Chemelute tube packed with celite pretreated with 2M sodium carbonate using chloroform and the eluant concentrated under a nitrogen stream. A solution of the residue in chloroform (2 ml) and trifluoroacetic acid (2 ml) was stirred for 30 minutes at ambient temperature followed by concentration under a nitrogen stream. Purification by reverse phase HPLC (10–70% acetonitrile/water) followed by lyophilization yielded 60 mg (37% yield) of product as an off-white solid. $^1$H NMR (CDCl$_3$) δ1.26 (d, J=6.3 Hz, 6H), 3.3–4.5 (br m, 6H), 3.71 (S, 2H), 4.39 (s, 2H), 6.37–6.48 (m, 2H), 6.87 (d, J=8.7 Hz, 1H), 6.94 (d, J=8.4 Hz, 1H), 7.12 (d. J=8.7 Hz, 1H), 7.55 (d, J=8.1 Hz, 2H), 7.76 (d, J=8.1 Hz, 2H), 8.81 (t, J=5.4 Hz, 1H), 9.07 (br s, 1H), 9.27 (br s, 1H) . HRMS calc'd for $C_{24}H_{30}N_7O_2$ (M+H): 448.2461. Found: 448.2472. Anal. Calc'd for $C_{24}H_{29}N_7O_2$+2.5 TFA, 1.8 $H_2O$: C, 45.53; H, 4.62; N, 12.81. Found: C, 45.53; H, 4.58; N, 12.85.

Example 8

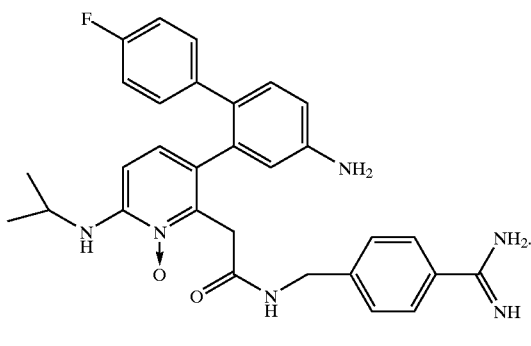

Using the procedure of Example 7 with 4'-fluoro-2-biphenyl boronic acid, the product was obtained as an off-white solid. HRMS calc'd for $C_{30}H_{31}N_5O_2F$ (M+H): 512.2462. Found: 512.2467.

Example 9

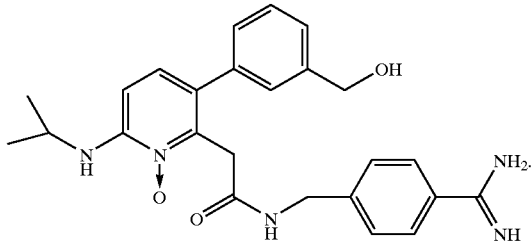

Using the procedure of Example 7 with (3-hydroxymethylphenyl)boronic acid, the product was obtained as an off-white solid. HRMS calc'd for $C_{25}H_{30}N_5O_3$ (M+H): 448.2349. Found: 448.2349.

Example 10

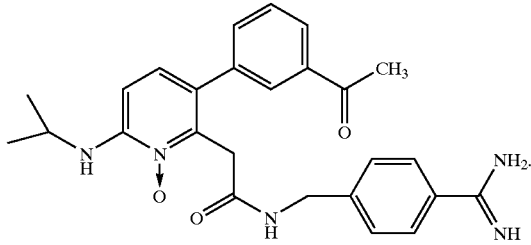

Using the procedure of Example 7 with 3-acetylphenylboronic acid, the product was obtained as an off-white solid. HRMS calc'd for $C_{26}H_{30}N_5O_3$ (M+H): 460.2349. Found: 460,2366.

Example 11

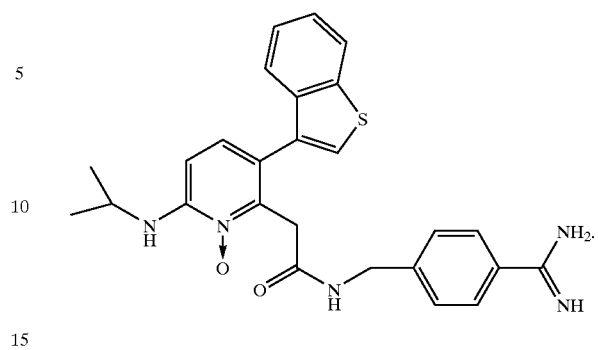

Using the procedure of Example 7 with benzothiophene-3-boronic acid, the product was obtained as an off-white solid. HRMS calc'd for $C_{26}H_{28}N_5O_2S$ (M+H): 474.1964. Found: 474.1949.

Example 12

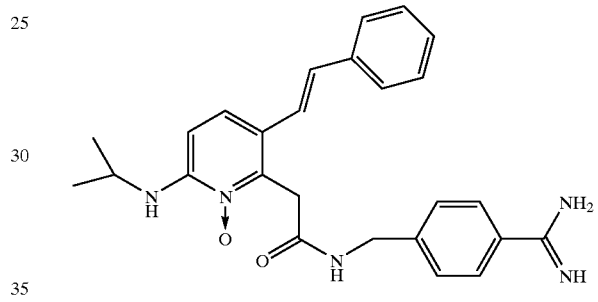

Using the procedure of Example 7 with transbiphenylethenylboronic acid, the product was obtained as an off-white solid. HRMS calc'd for $C_{26}H_{30}N_5O_2$ (M+H): 444.2400. Found: 444.2396.

Example 13

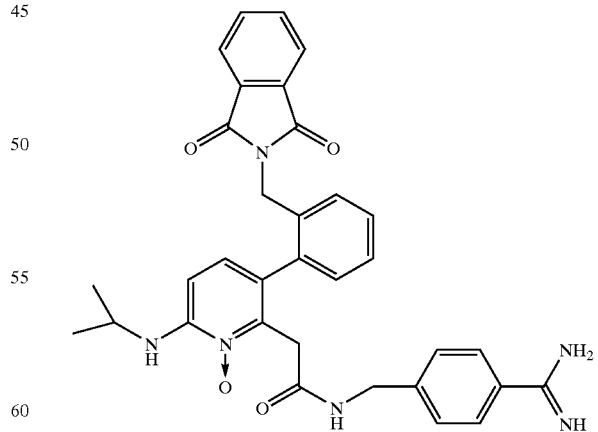

Using the procedure of Example 7 with (2-phthalimidomethylphenyl)-boronic acid, the product was obtained as an off-white solid. HRMS calc'd for $C_{33}H_{33}N_6O_4$ (M+H): 577.2563. Found: 577.2620.

Example 14

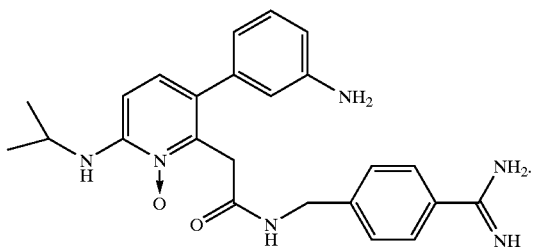

Following methods disclosed above and using EX-5H as starting material and (3-aminophenyl)boronic acid as a reagent, crude material EX-14A was obtained: (MS (ES, m/z) 533.28 (M+H). EX-14A was used directly in the next step of the procedure. The product was obtained in a yield of 45%. HRMS calc'd for $C_{24}H_{28}N_6O_2$ (M+H): 433.2352. Found: 433.2368. Anal. Calc'd for $C_{24}H_{28}N_6O_2+2.15TFA$, $1.05H_2O$: C, 48.80; H, 4.67; N, 12.06. Found: C, 48.80; H, 4.57; N, 12.11.

Using the examples and methods described herein previously, the following examples having a amidinoaralkyl or amidinoheteroaralkyl type $Y^o$ group could be prepared:

2-[2-[N-[[4-aminoiminomethylphenyl]methyl]-3-[3-aminophenyl]-6-[N,N-dimethylhydrazino]-1-oxypyridinyl]]acetamide;

2-[2-[N-[[4-aminoiminomethylphenyl]methyl]-3-[3-aminophenyl]-6-[N-ethyl-N-methylhydrazino]-1-oxypyridinyl]]acetamide;

2-[2-[N-[[4-aminoiminomethylphenyl]methyl]-3-[3-aminophenyl]-5-chloro-6-[N,N-dimethylhydrazino]-1-oxypyridinyl]]acetamide;

2-[2-[N-[[4-aminoiminomethylphenyl]methyl]-3-[3-aminophenyl]-5-chloro-6-[N-ethyl-N-methylhydrazino]-1-oxypyridinyl]]acetamide;

2-[2-[N-[[4-aminoiminomethylphenyl]methyl]-3-[3,5-diaminophenyl]-6-[N,N-dimethylhydrazino]-1-oxypyridinyl]]acetamide;

2-[2-[N-[[4-aminoiminomethylphenyl]methyl]-3-[3,5-diaminophenyl]-6-[N-ethyl-N-methylhydrazino]-1-oxypyridinyl]]acetamide;

2-[2-[N-[[4-aminoiminomethylphenyl]methyl]-3-[3,5-diaminophenyl]-5-chloro-6-[N,N-dimethylhydrazino]-1-oxypyridinyl]]acetamide;

2-[2-[N-[[4-aminoiminomethylphenyl]methyl]-3-[3,5-diaminophenyl]-5-chloro-6-[N-ethyl-N-methylhydrazino]-1-oxypyridinyl]]acetamide;

2-[2-[N-[[4-aminoiminomethylphenyl]methyl]-3-[3-amino-5-carboxyphenyl]-6-[N,N-dimethylhydrazino]-1-oxypyridinyl]]acetamide;

2-[2-[N-[[4-aminoiminomethylphenyl]methyl]-3-[3-amino-5-carboxyphenyl]-6-[N-ethyl-N-methylhydrazino]-1-oxypyridinyl]]acetamide;

2-[2-[N-[[4-aminoiminomethylphenyl]methyl]-3-[3-amino-5-carboxyphenyl]-5-chloro-6-[N,N-dimethylhydrazino]-1-oxypyridinyl]]acetamide;

2-[2-[N-[[4-aminoiminomethylphenyl]methyl]-3-[3-amino-5-carboxyphenyl]-5-chloro-6-[N-ethyl-N-methylhydrazino]-1-oxypyridinyl]]acetamide;

2-[2-[N-[[4-aminoiminomethylphenyl]methyl]-3-[3-amino-5-(N-benzylamidocarbonyl)phenyl]-6-[N,N-dimethylhydrazino]-1-oxypyridinyl]]acetamide;

2-[2-[N-[[4-aminoiminomethylphenyl]methyl]-3-[3-amino-5-(N-benzylamidocarbonyl)phenyl]-6-[N-ethyl-N-methylhydrazino]-1-oxypyridinyl]]acetamide;

2-[2-[N-[[4-aminoiminomethylphenyl]methyl]-3-[3-amino-5-(N-benzylamidocarbonyl)phenyl]-5-chloro-6-[N,N-dimethylhydrazino]-1-oxypyridinyl]]acetamide;

2-[2-[N-[[4-aminoiminomethylphenyl]methyl]-33-amino-5-(N-benzylamidocarbonyl)phenyl]-5-chloro-6-[N-ethyl-N-methylhydrazino]-1-oxypyridinyl]]acetamide.

Using the examples and methods described herein previously, the following further examples having a amidinoaralkyl or amidinoheteroaralkyl type Yo group could be prepared of the formula:

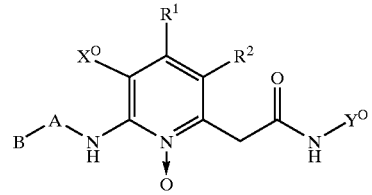

wherein;

$R^2$ is 3-aminophenyl, B is phenyl, A is $CH_2$, $Y^o$ is 4-amidinobenzyl, and $R^1$ is chloro;

$R^2$ is 3-aminophenyl, B is 3-chlorophenyl, A is $CH_2CH_2$, $Y^o$ is 4-amidinobenzyl, and $R^1$ is chloro;

$R^2$ is 3-aminophenyl, B is phenyl, A is $CH_2$, $Y^o$ is 4-amidinobenzyl, and $R^1$ is hydrido;

$R^2$ is 3-aminophenyl, B is 2-imidazoyl, A is $CH_2CH_2$, $Y^o$ is 4-amidinobenzyl, and $R^1$ is chloro;

2 is 3-amidocarbonyl-5-aminophenyl, B is 3-chlorophenyl, A is $CH_2CH_2$, $Y^o$ is 4-amidinobenzyl, and $R^1$ is chloro;

2 is 3-amino-5-(N-benzylamidocarbonyl) phenyl, B is 3-chlorophenyl, A is $CH_2CH_2$, $Y^o$ is 4-amidinobenzyl, and $R^1$ is chloro;

$R^2$ is 3-amino-5-(N-(2-chlorobenzyl)amidocarbonyl) phenyl, B is 3-chlorophenyl, A is $CH_2CH_2$, $Y^o$ is 4-amidinobenzyl, and $R^1$ is chloro;

$R^2$ is 3-amino-5-(N-(2-chlorobenzyl)amidosulfonyl) phenyl, B is 3-chlorophenyl, A is $CH_2CH_2$, $Y^o$ is 4-amidinobenzyl, and $R^1$ is chloro;

2 is 3-amino-5-(N-(2-trifluoromethylbenzyl) amidocarbonyl)-phenyl, B is 3-chlorophenyl, A is $CH_2CH_2$, $Y^o$ is 4-amidinobenzyl, and $R^1$ is chloro;

$R^2$ is 3,5-diaminophenyl, B is 3-chlorophenyl, A is $CH_2CH_2$, $Y^o$ is 4-amidinobenzyl, and $R^1$ is chloro;

$R^2$ is 3-amino-5-carboxyphenyl, B is 3-chlorophenyl, A is $CH_2CH_2$, $Y^o$ is 4-amidinobenzyl, and $R^1$ is chloro;

$R^2$ is 3-amidocarbonyl-5-aminophenyl, B is 3-chlorophenyl, A is $CH_2CH_2$, $Y^o$ is 4-amidinobenzyl, and $R^1$ is hydrido;

$R^2$ is 3-amino-5-(N-benzylamidocarbonyl)phenyl, B is 3-chlorophenyl, A is $CH_2CH_2$, $Y^o$ is 4-amidinobenzyl, and $R^1$ is hydrido;

$R^2$ is 3-amino-5-(N-(2-chlorobenzyl)amidocarbonyl) phenyl, B is 3-chlorophenyl, A is $CH_2CH_2$, $Y^o$ is 4-amidinobenzyl, and $R^1$ is hydrido;

$R^2$ is 3-amino-5-(N-(2-chlorobenzyl)amidosulfonyl) phenyl, B is 3-chlorophenyl, A is $CH_2CH_2$, $Y^o$ is 4-amidinobenzyl, and $R^1$ is hydrido;

$R^2$ is 3-amino-5-(N-(2-trifluoromethylbenzyl) amidocarbonyl)-phenyl, B is 3-chlorophenyl, A is $CH_2CH_2$, $Y^o$ is 4-amidinobenzyl, and $R^1$ is hydrido;

$R^2$ is 3,5-diaminophenyl, B is 3-chlorophenyl, A is $CH_2CH_2$, $Y^o$ is 4-amidinobenzyl, and $R^1$ is hydrido;

$R^2$ is 3-amino-5-carboxyphenyl, B is 3-chlorophenyl, A is $CH_2CH_2$, $Y^o$ is 4-amidinobenzyl, and $R^1$ is hydrido;

$R^2$ is 3-aminophenyl, B is 2,2,2-trifluoroethyl, A is a bond, $Y^o$ is 4-amidinobenzyl, and $R^1$ is chloro;

$R^2$ is 3-aminophenyl, B is (S)-2-butyl, A is a bond, $Y^o$ is 4-amidinobenzyl, and $R^1$ is chloro;

$R^2$ is 5-amino-2-fluorophenyl, B is isopropyl, A is a bond, $Y^o$ is 4-amidinobenzyl, and $R^1$ is chloro;

$R^2$ is 2-methyl-3-aminophenyl, B is isopropyl, A is a bond, $Y^o$ is 4-amidinobenzyl, and $R^1$ is chloro;

$R^2$ is 3-aminophenyl, B is ethyl, A is a bond, $Y^o$ is 4-amidinobenzyl, and $R^1$ is chloro;

$R^2$ is 3-aminophenyl, B is ethyl, A is a bond, $Y^o$ is 4-amidino-2-fluorobenzyl, and $R^1$ is chloro;

$R^2$ is 3-aminophenyl, B is 2-propenyl, A is a bond, $Y^o$ is 4-amidinobenzyl, and $R^1$ is chloro;

$R^2$ is 3-aminophenyl, B is isopropyl, A is a bond, $Y^o$ is 4-amidino-2-fluorobenzyl, and $R^1$ is chloro;

$R^2$ is 3-aminophenyl, B is isopropyl, A is a bond, $Y^o$ is 4-amidinobenzyl, and $R^1$ is chloro;

$R^2$ is 3-aminophenyl, B is 2-butyl, A is a bond, $Y^o$ is 4-amidinobenzyl, and $R^1$ is chloro;

$R^2$ is 3-aminophenyl, B is (R)-2-butyl, A is a bond, $Y^o$ is 4-amidinobenzyl, and $R^1$ is chloro;

$R^2$ is 3-aminophenyl, B is 2-propynyl, A is a bond, $Y^o$ is 4-amidinobenzyl, and $R^1$ is chloro;

$R^2$ is 3-aminophenyl, B is 3-pentyl, A is a bond, $Y^o$ is 4-amidinobenzyl, and $R^1$ is hydrido;

$R^2$ is 3-aminophenyl, B is hydrido, A is $CH_2$, $Y^o$ is 4-amidinobenzyl, and $R^1$ is chloro;

$R^2$ is 3-aminophenyl, B is ethyl, A is $CH_2$, $Y^o$ is 4-amidinobenzyl, and $R^1$ is chloro;

$R^2$ is 3-aminophenyl, B is 2-methypropyl, A is a bond, $Y^o$ is 4-amidinobenzyl, and $R^1$ is chloro;

$R^2$ is 3-aminophenyl, B is 2-propyl, A is $CH_3CH$, $Y^o$ is 4-amidinobenzyl, and $R_1$ is chloro;

$R^2$ is 3-aminophenyl, B is propyl, A is a bond, $Y^o$ is 4-amidino-2-fluorobenzyl, and $R^1$ is chloro;

$R^2$ is 3-aminophenyl, B is 6-amidocarbonylhexyl, A is a bond, $Y^o$ is 4-amidinobenzyl, and $R^1$ is chloro;

$R^2$ is 3-aminophenyl, B is tert-butyl, A is a bond, $Y^o$ is 4-amidinobenzyl, and $R^1$ is hydrido;

$R^2$ is 3-aminophenyl, B is tert-butyl, A is a bond, $Y^o$ is 4-amidinobenzyl, and $R^1$ is chloro;

$R^2$ is 3-aminophenyl, B is 3-hydroxypropyl, A is a bond, $Y^o$ is 4-amidinobenzyl, and $R^1$ is chloro;

$R^2$ is 3-aminophenyl, B is 2-methylpropyl, A is a bond, $Y^o$ is 4-amidino-2-fluorobenzyl, and $R^1$ is chloro;

$R^2$ is 3-aminophenyl, B is butyl, A is a bond, $Y^o$ is 4-amidinobenzyl, and $R^1$ is chloro;

$R^2$ is 3-aminophenyl, B is 1-methoxy-2-propyl, A is a bond, $Y^o$ is 4-amidinobenzyl, and $R^1$ is chloro;

$R^2$ is 3-aminophenyl, B is 2-methoxyethyl, A is a bond, $Y^o$ is 4-amidinobenzyl, and $R^1$ is chloro;

$R^2$ is 3-aminophenyl, B is 2-propyl, A is a bond, $Y^o$ is 5-amidino-2-thienylmethyl, and $R^1$ is chloro;

$R^2$ is 5-amino-2-methylthiophenyl, B is 2-propyl, A is a bond, $Y^o$ is 4-amidinobenzyl, and $R^1$ is chloro;

$R^2$ is 3-amino-5-carboxyphenyl, B is isopropyl, A is a bond, $Y^o$ is 4-amidinobenzyl, and $R^1$ is chloro;

$R^2$ is 3-amino-5-carbomethoxyphenyl, B is isopropyl, A is a bond, $Y^o$ is 4-amidinobenzyl, and $R^1$ is chloro;

$R^2$ is 3-aminophenyl, B is isopropyl, A is a bond, $Y^o$ is 4-amidinobenzyl, and $R^1$ is bromo;

$R^2$ is 3-amino-5-carboxamidophenyl, B is isopropyl, A is a bond, $Y^o$ is 4-amidinobenzyl, and $R^1$ is chloro;

$R^2$ is 3-amino-5-(N-benzyl-N-methylamidocarbonyl)phenyl, B is isopropyl, A is a bond, $Y^o$ is 4-amidinobenzyl, and $R^1$ is chloro;

$R^2$ is 3-amino-5-(N-(1-phenylethyl)amidocarbonyl)phenyl, B is isopropyl, A is a bond, $Y^o$ is 4-amidinobenzyl, and $R^1$ is chloro;

$R^2$ is 3-amino-5-(N-(2-phenyl-2-propyl)amidocarbonyl)phenyl, B is isopropyl, A is a bond, $Y^o$ is 4-amidinobenzyl, and $R^1$ is chloro;

$R^2$ is 3-amino-5-(N-(2,4-dichlorobenzyl)amidocarbonyl)phenyl, B is isopropyl, A is a bond, $Y^o$ is 4-amidinobenzyl, and $R^1$ is chloro;

$R^2$ is 3-amino-5-(N-(4-bromobenzyl)amidocarbonyl)phenyl, B is isopropyl, A is a bond, $Y^o$ is 4-amidinobenzyl, and $R^1$ is chloro;

$R^2$ is 3-amino-5-(N-benzylamidocarbonyl)phenyl, B is isopropyl, A is a bond, $Y^o$ is 4-amidinobenzyl, and $R^1$ is chloro;

$R^2$ is 3-amino-5-(N-(2-chlorobenzyl)amidocarbonyl)phenyl, B is isopropyl, A is a bond, $Y^o$ is 4-amidinobenzyl, and $R^1$ is chloro;

$R^2$ is 3-amino-5-(N-(2-trifluoromethylbenzyl)amidocarbonyl)phenyl, B is isopropyl, A is a bond, $Y^o$ is 4-amidinobenzyl, and $R^1$ is chloro;

$R^2$ is 3-amino-5-(N-(3-fluorobenzyl)amidocarbonyl)phenyl, B is isopropyl, A is a bond, $Y^o$ is 4-amidinobenzyl, and $R^1$ is chloro;

$R^2$ is 3-amino-5-(N-(3-trifluoromethylbenzyl)amidocarbonyl)phenyl, B is isopropyl, A is a bond, $Y^o$ is 4-amidinobenzyl, and $R^1$ is chloro;

$R^2$ is 3-amino-5-(N-isobutylamidocarbonyl)phenyl, B is isopropyl, A is a bond, $Y^o$ is 4-amidinobenzyl, and $R^1$ is chloro;

$R^2$ is 3-amino-5-(N-cyclobutylamidocarbonyl)phenyl, B is isopropyl, A is a bond, $Y^o$ is 4-amidinobenzyl, and $R^1$ is chloro;

$R^2$ is 3-amino-5-(N-cyclopentylamidocarbonyl)phenyl, B is isopropyl, A is a bond, $Y^o$ is 4-amidinobenzyl, and $R^1$ is chloro;

$R^2$ is 3-amino-5-(N-cycloheptylamidocarbonyl)phenyl, B is isopropyl, A is a bond, $Y^o$ is 4-amidinobenzyl, and $R^1$ is chloro;

$R^2$ is 3-amino-5-(N-(2-pyridylmethyl)amidocarbonyl)phenyl, B is isopropyl, A is a bond, $Y^o$ is 4-amidinobenzyl, and $R^1$ is chloro;

$R^2$ is 3-amino-5-(N-(3-pyridylmethyl)amidocarbonyl)phenyl, B is isopropyl, A is a bond, $Y^o$ is 4-amidinobenzyl, and $R^1$ is chloro;

$R^2$ is 3-amino-5-(N-(2-(4-methoxyphenyl)ethyl)amidocarbonyl)phenyl, B is isopropyl, A is a bond, $Y^o$ is 4-amidinobenzyl, and $R^1$ is chloro;

$R^2$ is 3-amino-5-(N-(3-phenylpropyl)amidocarbonyl)phenyl, B is isopropyl, A is a bond, $Y^o$ is 4-amidinobenzyl, and $R^1$ is chloro;

$R^2$ is 3-amino-5-(N-(2,2-diphenylethyl)amidocarbonyl)phenyl, B is isopropyl, A is a bond, $Y^o$ is 4-amidinobenzyl, and $R^1$ is chloro;

$R^2$ is 3-amino-5-(N-(2-naphthylmethyl)amidocarbonyl)phenyl, B is isopropyl, A is a bond, $Y^o$ is 4-amidinobenzyl, and $R^1$ is chloro;

$R^2$ is 3-amino-5-(N-(1,2,3,4-tetrahydronaphth-2-ylmethyl)amidocarbonyl)phenyl, B is isopropyl, A is a bond, $Y^o$ is 4-amidinobenzyl, and $R^1$ is chloro;

$R^2$ is 3-aminophenyl, B is 2-propyl, A is a bond, $Y^o$ is 4-amidino-3-fluorobenzyl, and $R^1$ is hydrido;

$R^2$ is 3-carboxyphenyl, B is 2-propyl, A is a bond, $Y^o$ is 4-amidinobenzyl, and $R^1$ is hydrido;

$R^2$ is 3-aminophenyl, B is 2-propyl, A is a bond, $Y^o$ is 4-amidino-3-fluorobenzyl, and $R^1$ is chloro;

$R^2$ is 3,5-diaminophenyl, B is 2,2,2-trifluoroethyl, A is a bond, $Y^o$ is 4-amidinobenzyl, and $R^1$ is chloro;

$R^2$ is 3,5-diaminophenyl, B is (S)-2-butyl, A is a bond, $Y^0$ is 4-amidinobenzyl, and $R^1$ is chloro;

$R^2$ is 3,5-diaminophenyl, B is isopropyl, A is a bond, $Y^0$ is 4-amidinobenzyl, and $R^1$ is chloro;

$R^2$ is 3,5-diaminophenyl, B is isopropyl, A is a bond, $Y^0$ is 4-amidino-2-fluorobenzylbenzyl, and $R^1$ is chloro;

$R^2$ is 3,5-diaminophenyl, B is ethyl, A is a bond, $Y^0$ is 4-amidinobenzyl, and $R^1$ is chloro;

$R^2$ is 3,5-diaminophenyl, B is ethyl, A is a bond, $Y^0$ is 4-amidino-2-fluorobenzyl, and $R^1$ is chloro;

$R^2$ is 3-amino-5-carboxyphenyl, B is 2,2,2-trifluoroethyl, A is a bond, $Y^0$ is 4-amidinobenzyl, and $R^1$ is chloro;

$R^2$ is 3-amino-5-carboxyphenyl, B is (S)-2-butyl, A is a bond, $Y^0$ is 4-amidinobenzyl, and $R^1$ is chloro;

$R^2$ is 3amino-5-carboxyphenyl, B is isopropyl, A is a bond, $Y^0$ is 4-amidino-2-fluorobenzylbenzyl, and $R^1$ is chloro;

$R^2$ is 3-amino-5-carboxyphenyl, B is ethyl, A is a bond, $Y^0$ is 4-amidinobenzyl, and $R^1$ is chloro;

$R^2$ is 3-amino-5-carboxyphenyl, B is ethyl, A is a bond, $Y^0$ is 4-amidino-2-fluorobenzyl, and $R^1$ is chloro;

$R^2$ is 3-amino-S-(N-benzylamidocarbonyl)phenyl, B is 2,2,2-trifluoroethyl, A is a bond, $Y^0$ is 4-amidinobenzyl, and $R^1$ is chloro;

$R^2$ is 3-amino-5-(N-benzylamidocarbonyl)phenyl, B is (S)-2-butyl, A is a bond, $Y^0$ is 4-amidinobenzyl, and $R^1$ is chloro;

$R^2$ is 3-amino-5-(N-benzylamidocarbonyl)phenyl, B is isopropyl, A is a bond, $Y^0$ is 4-amidino-2-fluorobenzylbenzyl, and $R^1$ is chloro;

$R^2$ is 3-amino-5-(N-benzylamidocarbonyl)phenyl, B is ethyl, A is a bond, $Y^0$ is 4-amidinobenzyl, and $R^1$ is chloro;

$R^2$ is 3-amino-5-(N-benzylamidocarbonyl)phenyl, B is ethyl, A is a bond, $Y^0$ is 4-amidino-2-fluorobenzyl, and $R^1$ is chloro;

$R^2$ is 3,5-diaminophenyl, B is isopropyl, A is a bond, $Y^0$ is 4-amidinobenzylbenzyl, and $R^1$ is hydrido;

$R^2$ is 3-aminophenyl, B is cyclopropyl, A is a bond, $Y^0$ is 4-amidinobenzyl, and $R^1$ is chloro;

$R^2$ is 3-aminophenyl, B is cyclobutyl, A is a bond, $Y^0$ is 4-amidino-2-fluorobenzyl, and $R^1$ is chloro;

$R^2$ is 3-aminophenyl, B is cyclobutyl, A is a bond, $Y^0$ is 4-amidinobenzyl, and $R^1$ is chloro;

$R^2$ is 3-aminophenyl, B is cyclopropyl, A is a bond, $Y^0$ is 4-amidino-2-fluorobenzyl, and $R^1$ is chloro;

$R^2$ is 3-aminophenyl, B is cyclobutyl, A is a bond, $Y^0$ is 4-amidinobenzyl, and $R^1$ is hydrido;

$R^2$ is 3-aminophenyl, B is cyclobutyl, A is a bond, $Y^0$ is 4-amidino-3-fluorobenzyl, and $R^1$ is chloro;

$R^2$ is 3-aminophenyl, B is cyclopentyl, A is a bond, $Y^0$ is 4-amidinobenzyl, and $R^1$ is chloro;

$R^2$ is 5-amino-2-thienyl, B is cyclobutyl, A is a bond, $Y^0$ is 4-amidinobenzyl, and $R^1$ is chloro;

$R^2$ is 3-aminophenyl, B is cyclopropyl, A is $CH_2$, $Y^0$ is 4-amidinobenzyl, and $R^1$ is chloro;

$R^2$ is 3-aminophenyl, B is 2-(2R)-bicyclo[2.2.1]-heptyl, A is a bond, $Y^0$ is 4-amidinobenzyl, and $R^1$ is chloro;

$R^2$ is 3-aminophenyl, B is cyclopentyl, A is a bond, $Y^0$ is 4-amidino-2-fluorobenzyl, and $R^1$ is chloro;

$R^2$ is 3-aminophenyl, B is cyclohexyl, A is $CH_2CH_2$, $Y^0$ is 4-amidinobenzyl, and $R^1$ is hydrido;

$R^2$ is 3-aminophenyl, B is oxalan-2-yl, A is $CH_2$, $Y^0$ is 4-amidinobenzyl, and $R^1$ is chloro;

$R^2$ is 3-aminophenyl, B is 1-piperidinyl, A is $CH_2CH_2$, $Y^0$ is 4-amidinobenzyl, and $R^1$ is chloro;

$R^2$ is 3-aminophenyl, B is 1-pyrrolidinyl, A is $CH_2CH_2$, $Y^0$ is 4-amidinobenzyl, and $R^1$ is chloro;

$R^2$ is 3-amino-5-carbomethoxyphenyl, B is cyclobutyl, A is a bond, $Y^0$ is 4-amidinobenzyl, and $R^1$ is hydrido;

$R^2$ is 3-amino-5-carboxyphenyl, B is cyclobutyl, A is a bond, $Y^0$ is 4-amidinobenzyl, and $R^1$ is hydrido;

$R^2$ is 3,5-diaminophenyl, B is cyclobutyl, A is a bond, $Y^0$ is 4-amidinobenzyl, and $R^1$ is hydrido;

$R^2$ is 2-amino-6-carboxy-4-pyridyl, B is cyclobutyl, A is a bond, $Y^0$ is 4-amidinobenzyl, and $R^1$ is hydrido;

$R^2$ is 3-amino-5-carbomethoxyphenyl, B is cyclobutyl, A is a bond, $Y^0$ is 4-amidinobenzyl, and $R^1$ is chloro;

$R^2$ is 3-amino-5-carboxyphenyl, B is cyclobutyl, A is a bond, $Y^0$ is 4-amidinobenzyl, and $R^1$ is chloro;

$R^2$ is 3,5-diaminophenyl, B is cyclopropyl, A is a bond, $Y^0$ is 4-amidinobenzyl, and $R^1$ is chloro;

$R^2$ is 3,5-diaminophenyl, B is cyclobutyl, A is a bond, $Y^0$ is 4-amidino-2-fluorobenzyl, and $R^1$ is chloro;

$R^2$ is 3,5-diaminophenyl, B is cyclopropyl, A is a bond, $Y^0$ is 4-amidino-2-fluorobenzyl, and $R^1$ is chloro;

$R^2$ is 3,5-diaminophenyl, B is cyclobutyl, A is a bond, $Y^0$ is 4-amidinobenzyl, and $R^1$ is hydrido;

$R^2$ is 3,5-diaminophenyl, B is cyclobutyl, A is a bond, $Y^0$ is 4-amidino-3-fluorobenzyl, and $R^1$ is chloro;

$R^2$ is 3,5-diaminophenyl, B is cyclopentyl, A is a bond, $Y^0$ is 4-amidinobenzyl, and $R^1$ is chloro;

$R^2$ is 3-carboxy-5-aminophenyl, B is cyclopropyl, A is a bond, $Y^0$ is 4-amidinobenzyl, and $R^1$ is chloro;

$R^2$ is 3-carboxy-5-aminophenyl, B is cyclobutyl, A is a bond, $Y^0$ is 4-amidino-2-fluorobenzyl, and $R^1$ is chloro;

$R^2$ is 3-carboxy-5-aminophenyl, B is cyclopropyl, A is a bond, $Y^0$ is 4-amidino-2-fluorobenzyl, and $R^1$ is chloro;

R is 3-carboxy-5-aminophenyl, B is cyclobutyl, A is a bond, $Y^0$ is 4-amidinobenzyl, and $R^1$ is hydrido;

$R^2$ is 3-carboxy-5-aminophenyl, B is cyclobutyl, A is a bond, $Y^0$ is 4-amidino-3-fluorobenzyl, and $R^1$ is chloro;

R is 3-carboxy-5-aminophenyl, B is cyclopentyl, A is a bond, $Y^0$ is 4-amidinobenzyl, and $R^1$ is chloro;

$R^2$ is 3-amino-5-(N-benzylamidocarbonyl)phenyl, B is cyclopropyl, A is a bond, $Y^0$ is 4-amidinobenzyl, and $R^1$ is chloro;

$R^2$ is 3-amino-5-(N-benzylamidocarbonyl)phenyl, B is cyclobutyl, A is a bond, $Y^0$ is 4-amidino-2-fluorobenzyl, and $R^1$ is chloro;

$R^2$ is 3-amino-5-(N-benzylamidocarbonyl)phenyl, B is cyclobutyl, A is a bond, $Y^0$ is 4-amidinobenzyl, and $R^1$ is chloro;

$R^2$ is 3-amino-5-(N-benzylamidocarbonyl)phenyl, B is cyclopropyl, A is a bond, $Y^0$ is 4-amidino-2-fluorobenzyl, and $R^1$ is chloro;

$R^2$ is 3-amino-5-(N-benzylamidocarbonyl)phenyl, B is cyclobutyl, A is a bond, $Y^0$ is 4-amidinobenzyl, and $R^1$ is hydrido;

$R^2$ is 3-amino-5-(N-benzylamidocarbonyl)phenyl, B is cyclobutyl, A is a bond, $Y^0$ is 4-amidino-3-fluorobenzyl, and $R^1$ is chloro;

$R^2$ is 3-amino-5-(N-benzylamidocarbonyl)phenyl, B is cyclopentyl, A is a bond, $Y^0$ is 4-amidinobenzyl, and $R^1$ is chloro;

$R^2$ is 3-amino-5-(N-(2-chlorobenzyl)amidosulfonyl)phenyl, B is cyclopropyl, A is a bond, $Y^0$ is 4-amidinobenzyl, and $R^1$ is chloro;

$R^2$ is 3-amino-5-(N-(2-chlorobenzyl)amidosulfonyl)phenyl, B is cyclobutyl, A is a bond, $Y^0$ is 4-amidino-2-fluorobenzyl, and $R^1$ is chloro;

$R^2$ is 3-amino-5-(N-(2-chlorobenzyl)amidosulfonyl)phenyl, B is cyclobutyl, A is a bond, $Y^0$ is 4-amidinobenzyl, and $R^1$ is chloro;

$R^2$ is 3-amino-5-(N-(2-chlorobenzyl)amidosulfonyl)phenyl, B is cyclopropyl, A is a bond, $Y^0$ is 4-amidino-2-fluorobenzyl, and $R^1$ is chloro;

$R^2$ is 3-amino-5-(N-(2-chlorobenzyl)amidosulfonyl)phenyl, B is cyclobutyl, A is a bond, $Y^o$ is 4-amidinobenzyl, and $R^1$ is hydrido;

$R^2$ is 3-amino-5-(N-(2-chlorobenzyl)amidosulfonyl)phenyl, B is cyclobutyl, A is a bond, $Y^o$ is 4-amidino-3-fluorobenzyl, and $R^1$ is chloro;

$R^2$ is 3-amino-5-(N-(2-chlorobenzyl)amidosulfonyl)phenyl, B is cyclopentyl, A is a bond, $Y^o$ is 4-amidinobenzyl, and $R^1$ is chloro;

$R^2$ is 3-amino-5-(N-(2-trifluoromethylbenzyl)amidocarbonyl)-phenyl, B is cyclopropyl, A is a bond, $Y^o$ is 4-amidinobenzyl, and $R^1$ is chloro;

$R^2$ is 3-amino-5-(N-(2-trifluoromethylbenzyl)amidocarbonyl)-phenyl, B is cyclobutyl, A is a bond, $Y^o$ is 4-amidino-2-fluorobenzyl, and $R^1$ is chloro;

$R^2$ is 3-amino-5-(N-(2-trifluoromethylbenzyl)amidocarbonyl)-phenyl, B is cyclobutyl, A is a bond, $Y^o$ is 4-amidinobenzyl, and $R^1$ is chloro;

$R^2$ is 3-amino-5-(N-(2-trifluoromethylbenzyl)amidocarbonyl)-phenyl, B is cyclopropyl, A is a bond, $Y^o$ is 4-amidino-2-fluorobenzyl, and $R^1$ is chloro;

$R^2$ is 3-amino-5-(N-(2-trifluoromethylbenzyl)amidocarbonyl)-phenyl, B is cyclobutyl, A is a bond, $Y^o$ is 4-amidinobenzyl, and $R^1$ is hydrido;

$R^2$ is 3-amino-5-(N-(2-trifluoromethylbenzyl)amidocarbonyl)-phenyl, B is cyclobutyl, A is a bond, $Y^o$ is 4-amidino-3-fluorobenzyl, and $R^1$ is chloro;

$R^2$ is 3-amino-5-(N-(2-trifluoromethylbenzyl)amidocarbonyl)-phenyl, B is cyclopentyl, A is a bond, $Y^o$ is 4-amidinobenzyl, and $R^1$ is chloro.

Using the examples and methods described herein previously, the following further additional examples having a guanidinoalkyl type $Y^{AT}$ group could be prepared of the formula:

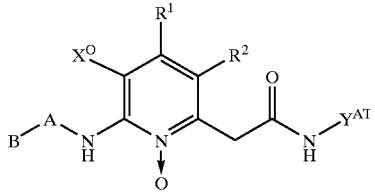

wherein;

$R^2$ is 3-aminophenyl, B is phenyl, A is $CH_2CH_2$, $Y^{AT}$ is 5-guanidino-1-oxo-1-(2-thiazolyl)-2-pentyl, $R^1$ is aminomethyl, and $X^o$ is chloro;

$R^2$ is 3,5-diaminophenyl, B is phenyl, A is $CH_2CH_2$, $Y^{AT}$ is 5-guanidino-1-oxo-1-(2-thiazolyl)-2-pentyl, $R^1$ is aminomethyl, and $X^o$ is chloro;

$R^2$ is 3-carboxy-5-aminophenyl, B is phenyl, A is $CH_2CH_2$, $Y^{AT}$ is 5-guanidino-1-oxo-1-(2-thiazolyl)-2-pentyl, $R^1$ is aminomethyl, and $X^o$ is chloro;

$R^2$ is 3-amino-5-(N-benzylamidocarbonyl)phenyl, B is phenyl, A is $CH_2CH_2$, $Y^{AT}$ is 5-guanidino-1-oxo-1-(2-thiazolyl)-2-pentyl, $R^1$ is aminomethyl, and $X^o$ is chloro;

$R^2$ is 3,5-diaminophenyl, B is isopropyl, A is single bond, $Y^{AT}$ is 5-guanidino-1-oxo-1-(2-thiazolyl)-2-pentyl, $R^1$ is aminomethyl, and $X^o$ is chloro;

$R^2$ is 3-carboxy-5-aminophenyl, B is isopropyl, A is single bond, $Y^{AT}$ is 5-guanidino-1-oxo-1-(2-thiazolyl)-2-pentyl, $R^1$ is aminomethyl, and $X^o$ is chloro;

$R^2$ is 3-amino-5-(N-benzylamidocarbonyl)phenyl, B is isopropyl, A is single bond, $Y^{AT}$ is 5-guanidino-1-oxo-1-(2-thiazolyl)-2-pentyl, $R^1$ is aminomethyl, and $X^o$ is chloro;

$R^2$ is 3,5-diaminophenyl, B is cyclobutyl, A is single bond, $Y^{AT}$ is 5-guanidino-1-oxo-1-(2-thiazolyl)-2-pentyl, $R^1$ is aminomethyl, and $X^o$ is chloro;

$R^2$ is 3-carboxy-5-aminophenyl, B is cyclobutyl, A is single bond, $Y^{AT}$ is 5-guanidino-1-oxo-1-(2-thiazolyl)-2-pentyl, $R^1$ is aminomethyl, and $X^o$ is chloro;

$R^2$ is 3-amino-S-(N-benzylamidocarbonyl)phenyl, B is cyclobutyl, A is single bond, $Y^{AT}$ is 5-guanidino-1-oxo-1-(2-thiazolyl)-2-pentyl, $R^1$ is aminomethyl, and $X^o$ is chloro;

$R^2$ is 3-aminophenyl, B is phenyl, A is $CH_2CH_2$, $Y^{AT}$ is 5-guanidino-1-oxo-1-(2-thiazolyl)-2-pentyl, $R^1$ is chloro, and $X^o$ is hydrido;

$R^2$ is 3,5-diaminophenyl, B is phenyl, A is $CH_2CH_2$, $Y^{AT}$ is 5-guanidino-1-oxo-1-(2-thiazolyl)-2-pentyl, $R^1$ is chloro, and $X^o$ is hydrido;

$R^2$ is 3-carboxy-5-aminophenyl, B is phenyl, A is $CH_2CH_2$, $Y^{AT}$ is 5-guanidino-1-oxo-1-(2-thiazolyl)-2-pentyl, $R^1$ is chloro, and $X^o$ is hydrido;

$R^2$ is 3-amino-5-(N-benzylamidocarbonyl)phenyl, B is phenyl, A is $CH_2CH_2$, $Y^{AT}$ is 5-guanidino-1-oxo-1-(2-thiazolyl)-2-pentyl, $R^1$ is chloro, and $X^o$ is hydrido;

$R^2$ is 3,5-diaminophenyl, B is isopropyl, A is single bond, $Y^{AT}$ is 5-guanidino-1-oxo-1-(2-thiazolyl)-2-pentyl, $R^1$ is chloro, and $X^o$ is hydrido;

$R^2$ is 3-carboxy-5-aminophenyl, B is isopropyl, A is single bond, $Y^{AT}$ is 5-guanidino-1-oxo-1-(2-thiazolyl)-2-pentyl, $R^1$ is chloro, and $X^o$ is hydrido;

$R^2$ is 3-amino-5-(N-benzylamidocarbonyl)phenyl, B is isopropyl, A is single bond, $Y^{AT}$ is 5-guanidino-1-oxo-1-(2-thiazolyl)-2-pentyl, $R^1$ is chloro, and $X^o$ is hydrido;

$R^2$ is 3,5-diaminophenyl, B is cyclobutyl, A is single bond, $Y^{AT}$ is 5-guanidino-1-oxo-1-(2-thiazolyl)-2-pentyl, $R^1$ is chloro, and $X^o$ is hydrido;

$R^2$ is 3-carboxy-5-aminophenyl, B is cyclobutyl, A is single bond, $Y^{AT}$ is 5-guanidino-1-oxo-1-(2-thiazolyl)-2-pentyl, $R^1$ is chloro, and $X^o$ is hydrido;

$R^2$ is 3-amino-5-(N-benzylamidocarbonyl)phenyl, B is cyclobutyl, A is single bond, $Y^{AT}$ is 5-guanidino-1-oxo-1-(2-thiazolyl)-2-pentyl, $R^1$ is chloro, and $X^o$ is hydrido.

Formula (I or A) compounds of this invention possessing hydroxyl, thiol, and amine functional groups can be converted to a wide variety derivatives. Alternatively, derivatized Formula (I or A) compounds can be obtained by first derivatizing one or more intermediates in the processes of preparation before further transforming the derivatized intermediate to compounds of Formula (I or A). A hydroxyl group in the form of an alcohol or phenol can be readily converted to esters of carboxylic, sulfonic, carbamic, phosphonic, and phosphoric acids. Acylation to form a carboxylic acid ester is readily effected using a suitable acylating reagent such as an aliphatic acid anhydride or acid chloride. The corresponding aryl and heteroaryl acid anhydrides and acid chlorides can also be used. Such reactions are generally carried out using an amine catalyst such as pyridine in an inert solvent. Similarly, carbamic acid esters (urethanes) can be obtained by reacting a hydroxyl group with isocyanates and carbamoyl chlorides. Sulfonate, phosphonate, and phosphate esters can be prepared using the corresponding acid chloride and similar reagents. Compounds of Formula (I or A) that have at least one thiol group present can be converted to the corresponding thioesters derivatives analogous to those of alcohols and phenols using the same reagents and comparable reaction conditions. Compounds of Formula (I or A) that have at least one primary or secondary amine group present can be converted to the corresponding amide derivatives. Amides of carboxylic acids can be prepared using the appropriate acid chloride or anhydrides with reaction conditions analogous to those used with alcohols and phenols. Ureas of the corresponding primary or secondary amine can be prepared using isocyanates directly and carbamoyl chlorides in the presence of an acid scavenger such as triethylamine or pyridine. Sulfonamides can be prepared from the corresponding sulfonyl chloride in the presence of aqueous sodium hydroxide or a tertiary amine. Suitable procedures and methods for preparing these derivatives can be found in House's Modern Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis, Volume 1, John Wiley & Sons. Reagents of a wide variety that can be used to derivatize hydroxyl, thiol, and amines of compounds of Formula (I or A) are available from commercial sources or the references cited above, which are incorporated herein by reference.

Formula (I or A) compounds of this invention possessing hydroxyl, thiol, and amine functional groups can be alkylated to a wide variety of derivatives. Alternatively, alkylated Formula (I or A) compounds can be obtained by first alkylating one or more intermediates in the processes of preparation before further transforming the alkylated intermediate to compounds of Formula (I or A). A hydroxyl group of compounds of Formula (I or A) can be readily converted to ethers. Alkylation to form an ether is readily effected using a suitable alkylating reagent such as an alkyl bromide, alkyl iodide or alkyl sulfonate. The corresponding aralkyl, heteroaralkyl, alkoxyalkyl, aralkyloxyalkyl, and heteroaralkyloxyalkyl bromides, iodides, and sulfonates can also be used. Such reactions are generally carried out using an alkoxide forming reagent such as sodium hydride, potassium t-butoxide, sodium amide, lithium amide, and n-butyl lithium using an inert polar solvent such as DMF, DMSO, THF, and similar, comparable solvents. amine catalyst such as pyridine in an inert solvent. Compounds of Formula (I or A) that have at least one thiol group present can be converted to the corresponding thioether derivatives analogous to those of alcohols and phenols using the same reagents and comparable reaction conditions. Compounds of Formula (I or A) that have at least one primary, secondary or tertiary amine group present can be converted to the corresponding secondary, tertiary or quaternary ammonium derivative. Quaternary ammonium derivatives can be prepared using the appropriate bromides, iodides, and sulfonates analogous to those used with alcohols and phenols. Conditions involve reaction of the amine by warming it with the alkylating reagent with a stoichiometric amount of the amine (i.e., one equivalent with a tertiary amine, two with a secondary, and three with a primary). With primary and secondary amines, two and one equivalents, respectively, of an acid scavenger are used concurrently. Secondary or tertiary amines can be prepared from the corresponding primary or secondary amine. A primary amine can be dialkylated by reductive amination using an aldehyde, such as formaldehyde, and sodium cyanoborohydride in the presence of glacial acetic acid. A primary amine can be monoalkylated by first monoprotecting the amine with a ready cleaved protecting group, such as trifluoroacetyl. An alkylating agent, such as dimethylsulfate, in the presence of a non-nucleophilic base, such as Barton's base (2-tert-butyl-1,1,3,3-tetramethylguanidine), gives the monomethylated protected amine. Removal of the protecting group using aqueous potassium hydroxide gives the desired monoalkylated amine. Additional suitable procedures and methods for preparing these derivatives can be found in House's Modern Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis published by John Wiley & Sons. Perfluoroalkyl derivatives can be prepared as described by DesMarteau in J. Chem. Soc. Chem. Commun. 2241 (1998). Reagents of a wide variety that can be used to derivatize hydroxyl, thiol, and amines of compounds of Formula (I or A) are available from commercial sources or the references cited above, which are incorporated herein by reference.

Assays for Biological Activity

TF-VIIa Assay

In this assay 100 nM recombinant soluble tissue factor and 2 nM recombinant human factor VIIa are added to a 96-well assay plate containing 0.4 mM of the substrate, N-Methylsulfonyl-D-phe-gly-arg-p-nitroaniline and either inhibitor or buffer (5 mM $CaCl_2$, 50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of TF-VIIa activity is calculated from OD405nm value from the experimental and control sample.

Xa Assay

Human factor Xa (0.3 nM) and 0.15 mM N-a-Benzyloxycarbonyl-D-arginyl-L-glycyl-L-arginine-p-nitroaniline-dihydrochloride (S-2765) are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of Xa activity is calculated from $OD_{405}$nm value from the experimental and control sample.

Thrombin Assay

Human thrombin (0.28 nM) and 0.06 mM H-D-Phenylalanyl-L-pipecolyl-L-arginine-p-nitroaniline dihydrochloride are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of thrombin activity is calculated from $OD_{405}$nm value from the experimental and control sample.

Trypsin Assay

Trypsin (5 ug/ml; type IX from porcine pancreas) and 0.375 mM N-α-Benzoyl-L-arginine-p-nitroanilide (L-BAPNA) are added to a 96-well assay plate containing either inhibitor or buffer (50 mM Tris-HCl, pH 8.0, 100 mM NaCl, 0.1% BSA). The reactions, in a final volume of 100 ul are measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of trypsin activity is calculated from OD405nm value from the experimental and control sample.

Recombinant soluble TF, consisting of amino acids 1–219 of the mature protein sequence was expressed in *E. coli* and purified using a Mono Q Sepharose FPLC. Recombinant human VIIa was purchased from American Diagnostica, Greenwich CT and chromogenic substrate N-Methylsulfonyl-D-phe-gly-arg-p-nitroaniline was prepared by American Peptide Company, Inc., Sunnyvale, Calif. Factor Xa was obtained from Enzyme Research Laboratories, South Bend IN, thrombin from Calbiochem, La Jolla, Calif. and trypsin and L-BAPNA from Sigma, St. Louis Mo. The chromogenic substrates S-2765 and S-2238 were purchased from Chromogenix, Sweden.

Using bioassay procedures described herein, the biological activity of the compounds of Example 1 through Example 14 are summarized in Table 1.

TABLE 1

Inhibitory Activity of Substituted Pyridines toward Factor Xa, TF-VIIA, Thrombin II, and Trypsin II.

| Example Number | TF-VIIA $IC_{50}$ ($\mu M$) | Factor Xa $IC_{50}$ ($\mu M$) | Thrombin II $IC_{50}$ ($\mu M$) | Trpysin II $IC_{50}$ ($\mu M$) |
|---|---|---|---|---|
| 1 | 2.46 | 27% @ 30 $\mu M$ | 0.71 | 0.06 |
| 2 | 0.07 | 26% @ 30 $\mu M$ | 7.13 | 0.02 |
| 3 | 0.72 | >100 | >100 | 0.158 |
| 4 | 0.241 | >100 | 8.8 | 0.02 |
| 5 | 2.38 | >100 | 0.37 | 0.1 |
| 6 | 6.94 | >100 | 86.5 | 0.17 |
| 7 | 0.084 | >100 | 60.7 | 0.022 |
| 8 | 18 | 75 | 48.6 | 0.47 |
| 9 | 1.72 | >100 | 6.6 | 0.21 |
| 10 | 1.7 | 40% @ 100 $\mu M$ | 3 | 0.035 |
| 11 | 5.6 | 21 | 39.5 | 0.079 |
| 12 | 23% at 100 $\mu M$ | >100 | 29 | 0.99 |
| 13 | 1.42 | >100 | 12.03 | 0.121 |
| 14 | 0.155 | >100 | 9.9 | <0.14 |

What we claim is:

1. A compound having the structure:

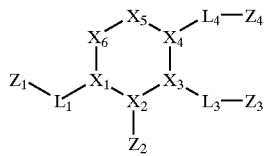

wherein $X_1$, $X_2$, $X_3$ $X_4$, $X_5$, and $X_6$ are each ring atoms defining a 6 membered heterocyclic ring;

$X_1$, $X_2$, and $X_4$ are independently carbon or nitrogen; $X_3$ is carbon;

$X_5$ and $X_6$ are independently carbon, nitrogen, oxygen or sulfur, provided at least one of $X_1$, $X_4$, and $X_6$ is other than carbon when $X_2$ is carbon;

$L_1$, $L_3$ and $L_4$ are linkages through which $Z_1$, $Z_3$, and $Z_4$, respectively, are covalently bonded to different ring atoms of the 6 membered heterocyclic ring defined by $X_1$, $X_2$, $X_3$, $X_4$, $X_5$, and $X_6$, wherein $Z_1$ is covalently bonded to $X_1$, $Z_3$ is covalently bonded to $X_3$, and $Z_4$ is covalently bonded to $X_4$, each of $L_1$, $L_3$ and $L_4$ independently being a covalent bond or comprising one or more atoms through which $Z_1$, $Z_3$, and $Z_4$ are covalently bonded to $X_1$, $X_3$ and $X_4$, respectively;

$L_1$ is —NH;

$L_3$ is —CH$_2$CONHCH$_2$;

$L_4$ is a bond;

$Z_3$ is a substituted hydrocarbyl, or a 5 or 6 membered substituted heterocyclic or aromatic ring, the substituents of the hydrocarbyl or ring comprising an amidine, guanidine, amino, or aminoalkyl group, the ring atoms of the 5 or 6 membered heterocyclic or aromatic ring of $Z_3$ being carbon, sulfur, nitrogen, or oxygen, wherein the 5 or 6 membered ring is optionally substituted at any position with halogen, hydroxy, or alkyl;

$Z_4$ comprises hydrocarbyl, substituted hydrocarbyl or a 5 or 6-membered heterocyclic ring, the ring atoms of the 5 or 6-membered heterocyclic ring being carbon, sulfur, nitrogen or oxygen;

$Z_1$ is alkyl; and $Z_2$ is a hydrogen bond acceptor covalently or datively bonded to $X_2$ or hydrogen.

2. The compound of claim 1 wherein:

$Z_3$ comprises a 5 or 6 membered heterocyclic or aromatic ring substituted with an amidine group, the ring atoms of the 5 or 6 membered heterocyclic or aromatic ring of $Z_3$ being carbon, sulfur, nitrogen, or oxygen, wherein the 5 or 6 membered ring is optionally substituted at any position with halogen, hydroxy, or alkyl; and $Z_4$ comprises a 5 or 6 membered heterocyclic or carbocyclic ring, the ring atoms of the 5 or 6 membered heterocyclic or carbocyclic ring of $Z_4$ being carbon, nitrogen, oxygen, or sulfur.

3. The compound of claim 1 wherein the 5 or 6 membered heterocyclic or carbocyclic ring comprising $Z_4$ is substituted with two substituents, $R_{42}$ and $R_{44}$, and two ring atoms each of which is in the beta position relative to the ring atom of $Z_4$ through which $Z_4$ is covalently linked to $X_4$, wherein one of $R_{42}$ and $R_{44}$ is covalently bonded to one of said beta positions and the other of $R_{42}$ and $R_{44}$ is covalently bonded to the other of said beta positions.

4. The compound of claim 3 wherein $R_{42}$ is amino and $R_{44}$ is hydrogen, hydrocarbyl, substituted hydrocarbyl, heterocyclo, halogen, or a substituted or unsubstituted heteroatom selected from nitrogen, oxygen, sulfur and phosphorous.

5. The compound of claim 2 wherein the 5 or 6 membered heterocyclic or aromatic ring comprising $Z_3$ is optionally substituted at any position with fluorine, methyl or hydroxy.

6. The compound of claim 1 or 2 wherein $L_3$ is a glycine derivative.

7. The compound of claim 3 wherein $R_{44}$ is hydrogen, hydrocarbyl, substituted hydrocarbyl, heteroaryl, heterocyclo, halogen, acetamido, guanidino, hydroxy, nitro, amino, amidosulfonyl, acylamido, hydrocarbyloxy, substituted hydrocarbyloxy, hydrocarbylthio, substituted hydrocarbylthio, hydrocarbylsulfonyl, or substituted hydrocarbylsulfonyl.

8. The compound of claim 2 having the structure:

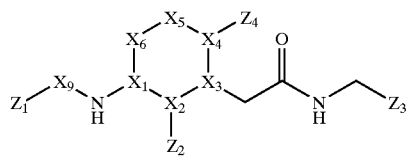

wherein $Z_1$, $Z_2$, $Z_3$, $X_1$, $X_2$, $X_3$ $X_4$, $X_5$, and $X_6$ are as defined in claim 2;

X$_9$ is a direct bond; and

Z$_4$ is covalently linked to X$_4$, wherein one of R$_{42}$ and R$_{44}$ is covalently bonded to one of said beta positions and the other of R$_{42}$ and R$_{44}$ is covalently bonded to the other of said beta positions.

9. The compound of each of claim 2, 3 or 8 wherein X$_2$ is nitrogen and Z$_2$ is hydrogen or a hydrogen bond acceptor.

10. The compound of each of claim 2, 3 or 8 wherein X$_2$ is nitrogen and Z$_2$ is hydrogen or oxygen.

11. The compound of each of claim 2, 3 or 8 wherein X$_5$ is carbon optionally substituted with a halogen.

12. The compound of each of claim 2, 3 or 8 wherein Z$_3$ is —R$_{300}$C(=NR$_{301}$)NR$_{302}$R$_{303}$, wherein R$^{300}$ is a 6 membered carbocyclic aromatic ring, R$_{301}$, R$_{302}$, R$_{303}$ are independently selected from hydrogen, optionally substituted hydrocarbyl, and optionally substituted hetero atoms selected from the group consisting of halogen, oxygen, nitrogen, phosphorous and sulfur.

13. The compound of each of claim 2, 3, or 8 wherein Z$_4$ is

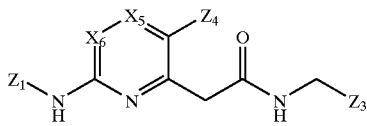

R$_{42}$ is amino;

R$_{44}$ is hydrocarbyl, substituted hydrocarbyl, halogen or an optionally substituted hetero atom selected from the group consisting of oxygen, nitrogen, and sulfur; and R$_{41}$, R$_{43}$ and R$_{45}$ are independently hydrogen, and hydrocarbyl, substituted hydrocarbyl, halogen or an optionally substituted hetero atom selected from the group consisting of oxygen, nitrogen, and sulfur.

14. The compound of claim 13 wherein R$^{44}$ is hydrocarbyl, substituted hydrocarbyl, acetamido, alkoxy, hydroxy, amino, alkylsulfonyl, haloalkyl, haloalkoxy, haloalkylthio, carboalkoxy, carboxy, carboxamidoalkyl, or carboxamidoalkylaryl.

15. The compound of claim 13 wherein each of R$_{41}$, R$_{43}$ and R$_{45}$ are hydrogen.

16. The compound of claim 8 wherein Z$_1$ is selected from the group consisting of isopropyl, isobutyl, sec-butyl, methyl, and ethyl, and Z$_3$ is benzene substituted with an amidine group.

17. The compound of each of claim 1–3 or 8 wherein X$_1$ is carbon.

18. The compound of each of claim 1–3 or 8 wherein X$_2$ is nitrogen.

19. The compound of each of claim 1–3 or 8 wherein X$_3$ is carbon.

20. The compound of each of claim 1–3 or 8 wherein X$_4$ is carbon.

21. The compound of each of claim 1–3 or 8 wherein X$_5$ is carbon.

22. The compound of each of claim 1–3 or 8 wherein X$_6$ is carbon.

23. A composition for inhibiting thrombotic conditions in blood comprising a compound of claim 1 and a pharmaceutically acceptable carrier.

24. A method for inhibiting thrombotic conditions in blood comprising adding to blood a therapeutically effective amount of the composition of claim 23.

25. A method for inhibiting formation of blood platelet aggregates in blood comprising adding to blood a therapeutically effective amount of the composition of claim 23.

26. A method for inhibiting thrombus formation in blood comprising adding to blood a therapeutically effective amount of the composition of claim 23.

27. A method for treating or preventing venuous thromboembolism and pulmonary embolism in a mammal comprising administering to the mammal a therapeutically effective amount of the composition of claim 23.

28. A method for treating or preventing deep vein thrombosis in a mammal comprising administering to the mammal a therapeutically effective amount of the composition of claim 23.

29. A method for treating or preventing cardiogenic thromboembolism in a mammal comprising administering to the mammal a therapeutically effective amount of the composition of claim 23.

30. A method for treating or preventing thromboembolic stroke in humans and other mammals comprising administering to the mammal a therapeutically effective amount of the composition of claim 23.

31. A method for treating or preventing thrombosis associated with cancer and cancer chemotherapy in humans and other mammals comprising administering to the mammal a therapeutically effective amount of the composition of claim 23.

32. A method for treating or preventing unstable angina in humans and other mammals comprising administering to the mammal a therapeutically effective amount of the composition of claim 23.

33. A method for inhibiting thrombus formation in blood comprising adding to blood a therapeutically effective amount of a compound of claim 1 with a therapeutically effective amount of fibrinogen receptor antagonist.

34. A compound having the structure
wherein:
X$_5$ is N or C—R$^1$;
X$_6$ is N or C—R$^1$;
R$^1$ is selected from the group consisting of hydrogen, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;
Z$_1$ is an optionally substituted C$_2$–C$_8$ alkyl;
Z$_3$ is a 5 or 6 membered heterocyclic or aromatic ring, the ring atoms of the 5 or 6 membered heterocyclic or aromatic ring of Z$_3$ being carbon, sulfur, nitrogen, or oxygen, wherein the 5 or 6 membered ring is optionally substituted at any position with halogen, hydroxy, or alkyl; and
Z$_4$ is phenyl or a 5 or 6 membered heteroaryl ring.

35. The compound of claim 34 wherein:
R$^1$ is selected from the group consisting of hydrogen, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;
Z$_1$ is is selected from the group consisting of ethyl, propyl, isopropyl, butyl, sec-butyl, tert-butyl, isobutyl, 2-methylbutyl, 3-methylbutyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of Z$_1$ is optionally substituted at any carbon up to and including 5 atoms from the point of attachment of Z$_1$ to N with one or more of the group consisting of $R_{32}$, $R_{33}$, $R_{34}$, $R_{35}$, and $R_{36}$;

$R_{32}$, $R_{33}$, $R_{34}$, $R_{35}$, and $R_{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, and cyano;

$Z_3$ is selected from the group consisting of:
1-$Q^b$-4-$Q^s$-2-$R^{16}$-3-$R^{17}$-5-$R^{18}$-6-$R^{19}$benzene, 2-$Q^b$-5-$Q^s$-6-$R^{17}$-4-$R^{18}$-3-$R^{19}$pyridine, 3-$Q^b$-6-$Q^s$-2-$R^{16}$-5-$R^{18}$-4-$R^{19}$pyridine, 2-$Q^b$-5-$Q^s$-3-$R^{16}$-6-$R^{18}$pyrazine, 3-$Q^b$-6-$Q^s$-2-$R^{18}$-5-$R^{18}$-4-$R^{19}$pyridazine, 2-$Q^b$-5-$Q^s$-4-$R^{17}$-6-$R^{18}$pyrimidine, 5-$Q^b$-2-$Q^s$-4-$R^{16}$-6-$R^{19}$pyrimidine, 3-$Q^b$-5-$Q^s$-4-$R^{16}$-2-$R^{19}$thiophene, 2-$Q^b$-5-$Q^s$-3-$R^{16}$-4-$R^{17}$thiophene, 3-$Q^b$-5-$Q^s$-4-$R^{16}$-2-$R^{19}$furan, 2-$Q^b$-5-$Q^s$-3-$R^{16}$-4-$R^{17}$furan, 3-$Q^b$-5-$Q^s$-4-$R^{16}$-2-$R^{19}$pyrrole, 2-$Q^b$-5-$Q^s$-3-$R^{16}$-4-$R^{17}$pyrrole, 4-$Q^b$-2-$Q^s$-5-$R^{19}$imidazole, 2-$Q^b$-4-$Q^s$-5-$R^{17}$imidazole, 3-$Q^b$-5-$Q^s$-4-$R^{16}$isoxazole, 5-$Q^b$-3-$Q^s$-4-$R^{16}$isoxazole, 2-$Q^b$-5-$Q^s$-4-$R^{16}$pyrazole, 4-$Q^b$-2-$Q^s$-5-$R^{19}$thaiazole, and 2-$Q^b$-5-$Q^s$-4-$R^{17}$thiazole;

$R^{17}$ and $R^{18}$ are independently selected from the group consisting of hydrogen, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano;

$R^{16}$ and $R^{19}$ are selected from the group consisting of:
(i) hydrogen, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano; and
(ii) $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrogen;

$Q^b$ is selected from the group consisting of $NR^{20}R^{21}$, hydrogen, $C(NR^{25})NR^{23}R^{24}$, and $N(R^{26})C(NR^{25})N(R^{23})(R^{24})$, with the proviso that no more than one of $R^{20}$, $R^{21}$, $R^{23}$, and $R^{24}$ can be hydroxy, when any two of the group consisting of $R^{20}$, $R^{21}$, $R^{23}$, and $R^{24}$ are bonded to the same atom and with the further proviso that said $Q^b$ group is bonded directly to a carbon atom;

$R^{20}$, $R^{21}$, $R^{23}$, $R^{24}$, $R^{25}$, and $R^{26}$ are independently selected from the group consisting of hydrogen, methyl, ethyl, propyl, butyl, isopropyl, and hydroxy;

$Q^s$ is selected from the group consisting of a bond, $CH_2$, and $CH_2CH_2$;

$Z_4$ is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment of said phenyl or heteroaryl ring to the $X_4$ carbon atom is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrogen, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano; and $R^{10}$ and $R^{12}$ are independently selected from the group consisting of hydrogen, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl)amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-isopropylamidocarbonyl, N-cyclobutylamidocarbonyl, N-cyclopentylamidocarbonyl, fluoro, chloro, bromo, cyano, cyclobutoxy, cyclohexoxy, cyclohexyl methoxy, 4-trifluoromethycyclohexyl methoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorobenzyloxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy.

36. The compound of claim 35 wherein $X_6$ is C—$R^1$.
37. The compound of claim 35 wherein $X_6$ is N.
38. The compound of claim 35 wherein:
$X_5$ is C—$R^1$;
$X_6$ is C—$R^1$;
$R^1$ is selected from the group consisting of hydrogen, hydroxy, amino, amidino, hydroxyamino, aminomethyl, methylamino, cyano, methyl, trifluoromethyl, methoxy, hydroxymethyl, methoxyamino, methylthio, trifluoromethoxy, fluoro, and chloro;
$Z_1$ is is selected from the group consisting of ethyl, propyl, isopropyl, butyl, sec-butyl, tert-butyl, isobutyl, 2-methyl butyl, 3-methyl butyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of $Z_1$ is optionally substituted at any carbon up to and including 5 atoms from the point of attachment of $Z_1$ to N with one or more of the group consisting of $R^{32}$, $R^{33}$, $R^{34}$, $R^{35}$, and $R^{36}$;
$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, and cyano;

$Z_3$ is selected from the group consisting of:
1-$Q^b$-4-$Q^s$-2-$R^{16}$-3-$R^{17}$-5-$R^{18}$-6-$R^{19}$benzene, 2-$Q^b$-5-$Q^s$-6-$R^{17}$-4-$R^{18}$-3-$R^{19}$pyridine, 3-$Q^b$-6-$Q^s$-2-$R^{16}$-5-$R^{18}$-4-$R^{19}$pyridine, 3-$Q^b$-5-$Q^s$-4-$R^{16}$-2-$R^{19}$thiophene, and 2-$Q^b$-5-$Q^s$-3-$R^{16}$-4-$R^{17}$thiophene;

$R^{16}$ and $R^{19}$ are independently selected from the group consisting of hydrogen, amidino, amino, aminomethyl, methoxy, methylamino, hydroxy, hydroxymethyl, fluoro, chloro, and cyano;

$R^{17}$ and $R^{18}$ are independently selected from the group consisting of hydrogen, fluoro, chloro, hydroxy, hydroxymethyl, amino, carboxy, and cyano;

$Q^b$ is C(NR$^{25}$)NR$^{23}$R$^{24}$;

$R^{23}$, $R^{24}$, and $R^{25}$ are independently selected from the group consisting of hydrogen and methyl;

$Q^s$ is OH$_2$; and $Z_4$ is selected from the group consisting of:
3-amidocarbonyl-5-aminophenyl, 3-amino-5-(N-benzylamidocarbonyl)phenyl, 3-amino-5-benzylphenyl, 3-amino-5-(2-phenylethyl)phenyl, 3-amino-5-benzylaminophenyl, 3-amino-5-(2-phenylethylamino)phenyl, 3-amino-5-benzyloxyphenyl, 3-amino-5-(2-phenylethoxy)phenyl, 3-amino-5-(N-(2-chlorobenzyl)amidocarbonyl)phenyl, 3-amino-5-(N-(3-fluorobenzyl)amidocarbonyl)phenyl, 3-amino-5-(N-(2-trifluoromethylbenzyl)amidocarbonyl)phenyl, 3-amino-5-(N-(1-phenylethyl)amidocarbonyl)phenyl, 3-amino-5-(N-(1-methyl-1-phenylethyl)amidocarbonyl)phenyl, 3-amino-5-(N-benzylamidosulfonyl)phenyl, 3-amino-5-(N-(2-chlorobenzyl)amidosulfonyl)phenyl, 3-amino-5-(N-ethylamidocarbonyl)phenyl, 3-amino-5-(N-isopropylamidocarbonyl)phenyl, 3-amino-5-(N-propylamidocarbonyl)phenyl, 3-amino-5-(N-isobutylamidocarbonyl)phenyl, 3-amino-5-(N-(2-butyl)amidocarbonyl)phenyl, 3-amino-5-(N-cyclobutylamidocarbonyl)phenyl, 3-amino-5-(N-cyclopentylamidocarbonyl)phenyl, 3-amino-5-(N-cyclohexylamidocarbonyl)phenyl, 5-amino-2-fluorophenyl, 3-amino-5-hydroxymethylphenyl, 5-amino-3-methoxycarbonylphenyl, 3-amidinophenyl, 3-amino-2-methylphenyl, 5-amino-2-methylthiophenyl, 3-aminophenyl, 3-carboxyphenyl, 3-carboxy-5-hydroxyphenyl, 3-amino-5-carboxyphenyl, 3-chlorophenyl, 2-chlorophenyl, 3-cyanophenyl, 3,5-diaminophenyl, 3-dimethylaminophenyl, 2-fluorophenyl, 3-fluorophenyl, 2-hydroxyphenyl, 3-hydroxyphenyl, 3-methanesulfonylaminophenyl, 2-methoxyphenyl, 3-methoxyphenyl, 3-methoxyaminophenyl, 3-methoxycarbonylphenyl, 2-methylaminophenyl, 3-methylaminophenyl, 2-methylphenyl, 3-methylphenyl, 4-methylphenyl, phenyl, 3-trifluoroacetamidophenyl, 3-trifluoromethylphenyl, 2-trifluoromethylphenyl, 5-amino-2-thienyl, 5-amino-3-thienyl, 3-bromo-2-thienyl, 3-pyridyl, 4-pyridyl, 2-thienyl, and 3-thienyl.

39. A compound having the structure

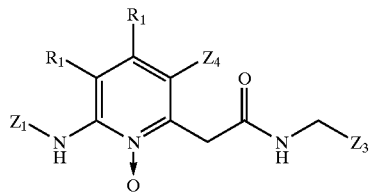

wherein:
$R^1$ is selected from the group consisting of hydrogen, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;

$Z_1$ is an optionally substituted $C_2$–$C_8$ alkyl;

$Z_3$ is a 5 or 6 membered heterocyclic or aromatic ring, the ring atoms of the 5 or 6 membered heterocyclic or aromatic ring of $Z_3$ being carbon, sulfur, nitrogen, or oxygen, wherein the 5 or 6 membered ring is optionally substituted at any position with halogen, hydroxy, or alkyl; and $Z_4$ is phenyl or a 5 or 6 membered heteroaryl ring.

40. The compound of claim 39 wherein:

$R^1$ is selected from the group consisting of hydrogen, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;

$Z_1$ is selected from the group consisting of ethyl, propyl, isopropyl, butyl, sec-butyl, tert-butyl, isobutyl, 2-methyl butyl, 3-methyl butyl, 2,2,2-trifluoroethyl, 2,2-difluoropropyl, 4-trifluoromethyl-5,5,5-trifluoropentyl, 4-trifluoromethylpentyl, 5,5,6,6,-pentafluorohexyl, and 3,3,3-trifluoropropyl, wherein each member of $Z_1$ is optionally substituted at any carbon up to and including 5 atoms from the point of attachment of $Z_1$ to N with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, and cyano;

$Z_3$ is selected from the group consisting of:
1-$Q^b$-4-$Q^s$-2-$R^{16}$-3-$R^{17}$-5-$R^{18}$-6-$R^{19}$benzene, 2-$Q^b$-5-$Q^s$-6-$R^{17}$-4-$R^{18}$-3-$R^{19}$pyridine, 3-$Q^b$-6-$Q^s$-2-$R^{16}$-5-$R^{18}$-4-$R^{19}$pyridine, 2-$Q^b$-5-$Q^s$-3-$R^{16}$-6-$R^{18}$pyrazine, 3-$Q^b$-6-$Q^s$-2-$R^{18}$-5-$R^{18}$-4-$R^{19}$pyridazine, 2-$Q^b$-5-$Q^s$-4-$R^{17}$-6-$R^{18}$pyrimidine, 5-$Q^b$-2-$Q^s$-4-$R^{16}$-6-$R^{19}$pyrimidine, 3-$Q^b$-5-$Q^s$-4-$R^{16}$-2-$R^{19}$thiophene, 2-$Q^b$-5-$Q^s$-3-$R^{16}$-4-$R^{17}$thiophene, 3-$Q^b$-5-$Q^s$-4-$R^{16}$-2-$R^{19}$furan, 2-$Q^b$-5-$Q^s$-3-$R^{16}$-4-$R^{17}$furan, 3-$Q^b$-5-$Q^s$-4-$R^{16}$-2-$R^{19}$pyrrole, 2-$Q^b$-5-$Q^s$-3-$R^{16}$-4-$R^{17}$pyrrole, 4-$Q^b$-2-$Q^s$-5-$R^{19}$imidazole, 2-$Q^b$-4-$Q^s$-5-$R^{17}$imidazole, 3-$Q^b$-5-$Q^s$-4-$R^{16}$isoxazole, 5-$Q^b$-3-$Q^s$-4-$R^{16}$isoxazole, 2-$Q^b$-5-$Q^s$-4-$R^{16}$pyrazole, 4-$Q^b$-2-$Q^s$-5-$R^{19}$thaiazole, and 2-$Q^b$-5-$Q^s$-4-$R^{17}$thiazole;

$R^{17}$ and $R^{18}$ are independently selected from the group consisting of hydrogen, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano;

$R^{16}$ and $R^{19}$ are selected from the group consisting of:
(i) hydrogen, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano; and
(ii) $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrogen; $Q^b$ is selected from the group consisting of $NR^{20}R^{21}$, hydrogen, $C(NR^{25})NR^{23}R^{24}$, and $N(R^{26})C(NR^{25})N(R^{23})(R^{24})$, with the proviso that no more than one of $R^{20}$, $R^{21}$, $R^{23}$, and $R^{24}$ can be hydroxy, when any two of the group consisting of $R^{20}$, $R^{21}$, $R^{23}$, and $R^{24}$ are bonded to the same atom and with the further proviso that said $Q^b$ group is bonded directly to a carbon atom;

$R^{20}$, $R^{21}$, $R^{23}$, $R^{24}$, $R^{25}$, and $R^{26}$ are independently selected from the group consisting of hydrogen, methyl, ethyl, propyl, butyl, isopropyl, and hydroxy;

$Q^s$ is selected from the group consisting of a bond, $CH_2$, and $CH_2CH_2$;

$Z_4$ is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment of said phenyl or heteroaryl ring to the $X_4$ carbon atom is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrogen, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano; and $R^{10}$ and $R^{12}$ are independently selected from the group consisting of hydrogen, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl) amidocarbonyl, N-(2-trifluoromethylbenzyl) amidocarbonyl, N-(1-phenylethyl)amidocarbonyl, N-(1-methyl-1-phenylethyl)amidocarbonyl, N-benzylamidosulfonyl, N-(2-chlorobenzyl) amidosulfonyl, N-isopropylamidocarbonyl, N-cyclobutylamidocarbonyl, N-cyclopentylamidocarbonyl, fluoro, chloro, bromo, cyano, cyclobutoxy, cyclohexoxy, cyclohexyl methoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorobenzyloxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy.

41. The compound of claim 39 wherein:

$R^1$ is selected from the group consisting of hydrogen, hydroxy, amino, amidino, hydroxyamino, aminomethyl, methylamino, cyano, methyl, trifluoromethyl, methoxy, hydroxymethyl, methoxyamino, methylthio, trifluoromethoxy, fluoro, and chloro;

$Z_3$ is selected from the group consisting of:
1-$Q^b$-4-$Q^s$-2-$R^{16}$-3-$R^{17}$-5-$R^{18}$-6-$R^{19}$benzene, 2-$Q^b$-5-$Q^s$-6-$R^{17}$-4-$R^{18}$-3-$R^{19}$pyridine, 3-$Q^b$-6-$Q^s$-2-$R^{16}$-5-$R^{18}$-4-$R^{19}$pyridine, 3-$Q^b$-5-$Q^s$-4-$R^{16}$-2-$R^{19}$thiophene, and 2-$Q^b$-5-$Q^s$-3-$R^{16}$-4-$R^{17}$thiophene;

$R^{16}$ and $R^{19}$ are independently selected from the group consisting of hydrogen, amidino, amino, aminomethyl, methoxy, methylamino, hydroxy, hydroxymethyl, fluoro, chloro, and cyano;

$R^{17}$ and $R^{18}$ are independently selected from the group consisting of hydrogen, fluoro, chloro, hydroxy, hydroxymethyl, amino, carboxy, and cyano;

$Q^b$ is $C(NR^{25})NR^{23}R^{24}$;

$R^{23}$, $R^{24}$, and $R^{25}$ are independently selected from the group consisting of hydrogen and methyl;

$Q^s$ is $OH_2$; and $Z_4$ is selected from the group consisting of:
3-amidocarbonyl-5-aminophenyl, 3-amino-5-(N-benzylamidocarbonyl)phenyl, 3-amino-5-benzylphenyl, 3-amino-5-(2-phenylethyl)phenyl, 3-amino-5-benzylaminophenyl, 3-amino-5-(2-phenylethylamino)phenyl, 3-amino-5-benzyloxyphenyl, 3-amino-5-(2-phenylethoxy) phenyl, 3-amino-5-(N-(2-chlorobenzyl) amidocarbonyl)phenyl, 3-amino-5-(N-(3-fluorobenzyl)amidocarbonyl)phenyl, 3-amino-5-(N-(2-trifluoromethylbenzyl)amidocarbonyl)phenyl, 3-amino-5-(N-(1-phenylethyl)amidocarbonyl) phenyl, 3-amino-5-(N-(1-methyl-1-phenylethyl)

amidocarbonyl)phenyl, 3-amino-5-(N-benzylamidosulfonyl)phenyl, 3-amino-5-(N-(2-chlorobenzyl)amidosulfonyl)phenyl, 3-amino-5-(N-ethylamidocarbonyl)phenyl, 3-amino-5-(N-isopropylamidocarbonyl)phenyl, 3-amino-5-(N-propylamidocarbonyl)phenyl, 3-amino-5-(N-isobutylamidocarbonyl)phenyl, 3-amino-5-(N-(2-butyl)amidocarbonyl)phenyl, 3-amino-5-(N-cyclobutylamidocarbonyl)phenyl, 3-amino-5-(N-cyclopentylamidocarbonyl)phenyl, 3-amino-5-(N-cyclohexylamidocarbonyl)phenyl, 5-amino-2-fluorophenyl, 3-amino-5-hydroxymethylphenyl, 5-amino-3-methoxycarbonylphenyl, 3-amidinophenyl, 3-amino-2-methylphenyl, 5-amino-2-methylthiophenyl, 3-aminophenyl, 3-carboxyphenyl, 3-carboxy-5-hydroxyphenyl, 3-amino-5-carboxyphenyl, 3-chlorophenyl, 2-chlorophenyl, 3-cyanophenyl, 3,5-diaminophenyl, 3-dimethylaminophenyl, 2-fluorophenyl, 3-fluorophenyl, 2-hydroxyphenyl, 3-hydroxyphenyl, 3-methanesulfonylaminophenyl, 2-methoxyphenyl, 3-methoxyphenyl, 3-methoxyaminophenyl, 3-methoxycarbonylphenyl, 2-methylaminophenyl, 3-methylaminophenyl, 2-methylphenyl, 3-methylphenyl, 4-methylphenyl, phenyl, 3-trifluoroacetamidophenyl, 3-trifluoromethylphenyl, 2-trifluoromethylphenyl, 5-amino-2-thienyl, 5-amino-3-thienyl, 3-bromo-2-thienyl, 3-pyridyl, 4-pyridyl, 2-thienyl, and 3-thienyl.

* * * * *